US011273217B2

(12) United States Patent
Yamada et al.

(10) Patent No.: US 11,273,217 B2
(45) Date of Patent: Mar. 15, 2022

(54) CANCER TREATMENT COMPOSITION COMBINING ANTI-CD26 ANTIBODY AND OTHER ANTICANCER AGENT

(71) Applicant: Y's AC Co., Ltd., Tokyo (JP)

(72) Inventors: Taketo Yamada, Tokyo (JP); Mutsumi Hayashi, Tokyo (JP); Kohji Yamada, Tokyo (JP); Chikao Morimoto, Tokyo (JP); Toshihiro Okamoto, Koshigaya (JP); Yutaro Kaneko, Tokyo (JP)

(73) Assignee: Y's AC Co., Ltd., Tokyo (JP)

( * ) Notice: Subject to any disclaimer, the term of this patent is extended or adjusted under 35 U.S.C. 154(b) by 416 days.

(21) Appl. No.: 15/759,170

(22) PCT Filed: Sep. 9, 2016

(86) PCT No.: PCT/JP2016/076542
§ 371 (c)(1),
(2) Date: Aug. 1, 2018

(87) PCT Pub. No.: WO2017/043613
PCT Pub. Date: Mar. 16, 2017

(65) Prior Publication Data
US 2018/0326052 A1 Nov. 15, 2018

(30) Foreign Application Priority Data

Sep. 11, 2015 (JP) .............................. JP2015-179672

(51) Int. Cl.
| *A61K 39/39* | (2006.01) |
| *A61K 39/395* | (2006.01) |
| *A61K 31/343* | (2006.01) |
| *A61K 31/519* | (2006.01) |
| *A61K 31/5377* | (2006.01) |
| *A61K 31/7068* | (2006.01) |
| *A61K 47/68* | (2017.01) |
| *G01N 33/574* | (2006.01) |
| *G01N 33/50* | (2006.01) |
| *C07K 16/40* | (2006.01) |
| *A61K 33/243* | (2019.01) |
| *A61P 35/00* | (2006.01) |
| *A61K 45/06* | (2006.01) |
| *C07K 16/28* | (2006.01) |
| *A61K 39/00* | (2006.01) |

(52) U.S. Cl.
CPC .......... *A61K 39/395* (2013.01); *A61K 31/343* (2013.01); *A61K 31/519* (2013.01); *A61K 31/5377* (2013.01); *A61K 31/7068* (2013.01); *A61K 33/243* (2019.01); *A61K 39/39558* (2013.01); *A61K 45/06* (2013.01); *A61K 47/6803* (2017.08); *A61K 47/6857* (2017.08); *A61K 47/6871* (2017.08); *A61P 35/00* (2018.01); *C07K 16/2896* (2013.01); *C07K 16/40* (2013.01); *G01N 33/5011* (2013.01); *G01N 33/57423* (2013.01); *A61K 2039/505* (2013.01); *A61K 2300/00* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| 6,294,546 B1 | 9/2001 | Rosen et al. | |
| 2003/0031665 A1* | 2/2003 | Dang ..................... | A61K 38/19 424/141.1 |
| 2007/0105771 A1 | 5/2007 | Aoyagi | |
| 2010/0135993 A1 | 6/2010 | Morimoto et al. | |
| 2012/0238529 A1* | 9/2012 | Georg .................. | A61K 31/665 514/100 |
| 2014/0004103 A1 | 1/2014 | Morimoto et al. | |

FOREIGN PATENT DOCUMENTS

| JP | 2003-508443 | 3/2003 | |
| JP | 2009-502139 A | 1/2009 | |
| JP | 2010-521418 A | 6/2010 | |
| WO | WO 2002/14462 A1 | 2/2002 | |
| WO | WO 2007/014169 * | 2/2007 | ............. C07K 16/28 |
| WO | WO 2008/114876 | 9/2008 | |
| WO | WO 2014/145303 A1 | 9/2014 | |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
Extended European Search Report received in European Patent Application No. 16844474.3 dated Apr. 5, 2019.
Written Opinion received in Singapore Patent Application No. 11201802915W dated Apr. 18, 2019.
Yamamoto, J., et al., Regulation of Somatostatin Receptor 4-Mediated Cytostatic Effects by CD26 in Malignant Pleural Mesothelioma, British Journal of Cancer 110(9): 2232-2245, Apr. 1, 2014.
Office Action issued in RU patent application No. 2018112649, dated Mar. 3, 2020.
Written Opinion issued in SG Patent Application No. 11201802915W, dated Jun. 4, 2020.

(Continued)

*Primary Examiner* — Nelson B Moseley, II
(74) *Attorney, Agent, or Firm* — Knobbe Martens Olson & Bear, LLP

(57) ABSTRACT

Mesothelioma growth inhibitory effect of standard cisplatin-pemetrexed concomitant therapy is potentiated by combination with an anti-CD26 antibody. A high therapeutic effect and excellent safety is obtained by the concomitant use of an anti-CD26 antibody and gemcitabine. By conjugating an anti-CD26 antibody (YS110) with triptolide via a divalent cross-linking agent for concomitant therapy using the anti-CD26 antibody, a novel antibody-drug conjugate (Y-TR1) very highly effective for CD26-positive malignant mesothelioma cells has been successfully obtained.

10 Claims, 31 Drawing Sheets

Specification includes a Sequence Listing.

(56) References Cited

OTHER PUBLICATIONS

Amatya et al., "Overexpression of CD26/DPPIV in Mesothelioma Tissue and Mesothelioma Cell Lines," Oncology Reports, vol. 26, pp. 1369-1375, 2011.
Boons et al., "The Value of Pemetrexed for the Treatment of Malignant Pleural Mesothelioma: A Comprehensive Review," Anticancer Research, vol. 33, pp. 3553-3562, 2013.
Camidge et al., "Sunitinib Combined with Pemetrexed and Cisplatin: Results of a Phase I Dose-Escalation and Pharmacokinetic Study in Patients with Advanced Solid Malignancies, with an Expanded Cohort in Non-Small Cell Lung Cancer and Mesothelioma," Cancer Chemother Pharmacol, vol. 71, pp. 307-319, Oct. 30, 2013.
Dowell et al., "A Multicenter Phase II Study of Cisplatin, Pemetrexed, and Bevacizumab in Patients with Advanced Malignant Mesothelioma," Lung Cancer, vol. 77, pp. 567-571, 2012.
Ellis et al., "The Use of Chemotherapy in Patients with Advanced Malignant Pleural Mesothelioma: A Systematic Review and Practice Guideline," Journal Thoracic Oncology, vol. 1, No. 6, pp. 591-601, Jul. 2006.
Hayashi et al., "A Humanized Anti-CD26 Monoclonal Antibody Inhibits Cell Growth of Malignant Mesothelioma via Retarded G2/M Cell Cycle Transition," Cancer Cell International, vol. 15, No. 35, pp. 1-10, 2016.
Huang et al., "Identification of Pregnancy-Associated Plasma Protein A as a Migration-Promoting Gene in Malignant Pleural Mesothelioma Cells: A Potential Therapeutic Target," Oncotarget, vol. 4, No. 8, pp. 1172-1184, Jul. 8, 2013.
Inamoto et al., "Humanized Anti-CD26 Monoclonal Antibody as a Treatment for Malignant Mesothelioma Tumors," Clinical Cancer Research, vol. 13, No. 14, pp. 4191-4200, Jul. 15, 2007.
International Search Report, dated Dec. 27, 2016, in International Application No. PCT/JP2016/076542.
Iwahori et al., "SOCS-1 Gene Delivery Cooperates with Cisplatin Plus Pemetrexed to Exhibit Preclinical Antitumor Activity Against Malignant Pleural Mesothelioma," International Journal of Cancer, vol. 132; pp. 459-471, 2013.
Janne et al., "Pemetrexed Alone or in Combination with Cisplatin in Previously Treated Malignant Pleural Mesothelioma: Outcomes From a Phase IIIB Expanded Access Program," Journal Thoracic Oncology, vol. 1, No. 6, pp. 506-512, Jul. 2006.
Janne, et al. "Phase II Trial of Pemetrexed and Gemcitabine in Chemotherapy-Naïve Malignant Pleural Mesothelioma," Journal of Clinical Oncology, vol. 26, No. 9., pp. 1465-1471, Mar. 20, 2008.
Kuribayashi et al., "Methotrexate and Gemcitabine Combination Chemotherapy for the Treatment of Malignant Pleural Mesothelioma," Molecular and Clinical Oncology, vol. 1, pp. 639-642, Apr. 9, 2013.
Li et al., "Interferon-β Produces Synergistic Combinatory Anti-Tumor Effects with Cisplatin or Pemetrexed on Mesothelioma Cells," PLoS ONE, vol. 8, Issue 8, pp. 1-12, Aug. 16, 2013.
Li et al., "Upregulated p53 Expression Activates Apoptotic Pathways in Wild-Type p53-Bearing Mesothelioma and Enhances Cytotoxicity of Cisplatin and Pemetrexed," Cancer Gene Therapy, vol. 19, No. 3, pp. 218-228, Mar. 2012.
Morimoto et al., "Antibody Therapy for Malignant Mesothelioma: Humanized Anti-CD26 MAB Therapy," Japanese Journal of Clinical Medicine, vol. 70, No. 12, pp. 2177-2182, 2012. (Article in Japanese; Only English Abstract provided).
Okamoto et al., "CD9 Negatively Regulates CD26 Expression and Inhibits CD26-Mediated Enhancement of Invasive Potential of Malignant Mesothelioma Cells," PLoS ONE, vol. 9, Issue 1, pp. 1-13, Jan. 2014.
Okuno et al., "A Phase 2 Study of Gemcitabine and Epirubicin for the Treatment of Pleural Mesothelioma," Cancer, vol. 112, pp. 1772-1779, Jan. 25, 2008.
Ong et al., "Chemotherapy in Malignant Pleural Mesothelioma: A Review," Journal of Clinical Oncology, vol. 14. , No. 3, pp. 1007-1017. Mar. 1996.
Palumbo et al., "Recombinant Erythropoietin Differently Affects Proliferation of Mesothelioma Cells but Not Sensitivity to Cisplatin and Pemetrexed," Cancer Chemother Pharmacol, vol. 61, pp. 893-901, 2008.
Ralli et al., "Docetaxel Plus Gemcitabine as First-Line Treatment in Malignant Pleural Mesothelioma: A Single Institution Phase II Study," Anticancer Research, vol. 29, pp. 3441-3444, 2009.
Raphael et al., "Efficacy of Phase 1 Trials in Malignant Pleural Mesothelioma: Description of a Series of Patients at a Single Institution," Lung Cancer, vol. 85, pp. 251-257, 2014.
Robinson et al., "Advances in Malignant Mesothelioma," The New England Journal of Medicine, vol. 353, Issue 15, pp. 1591-1603, Oct. 13, 2005.
Servais et al., "Mesothelin Overexpression Promotes Mesothelioma Cell Invasion and MMP-9 Secretion in an Orthotopic Mouse Model and in Epithelioid Pleural Mesothelioma Patients," Clinical Cancer Research, vol. 18, No. 9, pp. 2478-2489, May 1, 2012.
Shukuya et al., "Comparison of Cisplatin Plus Pemetrexed and Cisplatin Plus Gemcitabine for the Treatment of Malignant Pleural Mesothelioma in Japanese Patients," Respiratory Investigation, vol. 52, No. 2, pp. 101-106, Mar. 2014.
Stahel et al., "Malignant Pleural Mesothelioma: ESMO Clinical Practice Guidelines for Diagnosis, Treatment and Follow-Up," Annals of Oncology, vol. 21, Supplement 5, pp. 126-128, 2010.
Sun et al., "Pemetrexed Plus Cisplatin Versus Gemcitabine Plus Cisplatin According to Thymidylate Synthase Expression in Nonsquamous Non-Small-Cell Lung Cancer: A Biomarker-Stratified Randomized Phase II Trial," Journal of Clinical Oncology, vol. 33, No. 22, pp. 2450-2456, Aug. 1, 2015.
Toschi et al., "Role of Gemcitabine in Cancer Therapy," Future Oncology, vol. 1, No. 1, pp. 7-17, 2005.
Vandermeers, et al., "Valproate, in Combination with Pemetrexed and Cisplatin, Provides Additional Efficacy to the Treatment of Malignant Mesothelioma," Clinical Cancer Research, vol. 15, No. 8, pp. 2818-2828, Apr. 15, 2009.
Vogelzang, et al., "Phase III Study of Pemetrexed in Combination With Cisplatin Versus Cisplatin Alone in Patients with Malignant Pleural Mesothelioma," Journal of Clinical Oncology, vol. 21, No. 14, pp. 2636-2644, Jul. 15.
Written Opinion, dated Dec. 27, 2016, in International Application No. PCT/JP2016/076542.
Yamada et al., "Nuclear Localization of CD26 Induced by a Humanized Monoclonal Antibody Inhibits Tumor Cell Growth by Modulating of POLR2A Transcription," PLoS ONE, vol. 8, Issue 4, pp. 1-16, Apr. 29, 2013.
Zauderer et al., "Novel Therapies in Phase II and III Trials for Malignant Pleural Mesothelioma," Journal of National Comprehensive Cancer Network, vol. 10, No. 1, pp. 42-47, Jan. 2012.
Zauderer et al., "Vinorelbine and Gemcitabine as Second- or Third-Line Therapy for Malignant Pleural Mesothelioma," Lung Cancer, vol. 84, No. 3, pp. 271-274, Jun. 2014.
Chinese Office Action dated Jan. 5, 2021, corresponding to Chinese Patent Application No. 201680052747.9.
Hayashi, et al. "Novel antibody-drug conjugate with Anti-CD26 humanized monoclonal antibody and transcription factor IIH (TFIIH) inhibitor, triptolide, inhibits tumor growth via impairing mRNA synthesis." Cancers 11.8 (2019): 1138.
Phillips, et al. "Triptolide induces pancreatic cancer cell death via inhibition of heat shock protein 70." Cancer research 67.19 (2007): 9407-9416.
Rousalova, et al. (2013) Minnelide: A Novel Therapeutic That Promotes Apoptosis in Non-Small Cell Lung Carcinoma In Vivo. PLoS ONE 8(10): e77411. doi:10.1371/journal.pone.0077411.
Villicaña, et al. "The genetic depletion or the triptolide inhibition of TFIIH in p53-deficient cells induces a JNK-dependent cell death in Drosophila." Journal of Cell Science 126.11 (2013): 2502-2515.
Xiong, et al. "Triptolide has anticancer and chemosensitization effects by down-regulating Akt activation through the MDM2/REST pathway in human breast cancer." Oncotarget 7.17 (2016): 23933-23946.
Xu, et al. "Acute and subacute toxicity studies on triptolide and triptolide-loaded polymeric micelles following intravenous administration in rodents." Food and chemical toxicology 57 (2013): 371-379.

(56) References Cited

OTHER PUBLICATIONS

Morimoto, Chikao, and Kei Ohnuma. "Antibody therapy for malignant mesothelioma: humanized anti-cD26 mAb therapy." Nihon rinsho. Japanese journal of clinical medicine 70.12 (2012): 2177-2182.
Okamoto, Toshihiro, et al. "CD9 negatively regulates CD26 expression and inhibits CD26-mediated enhancement of invasive potential of malignant mesothelioma cells." PloS one 9.1 (2014): e86671.
Yamamoto, J., et al. "Regulation of somatostatin receptor 4-mediated cytostatic effects by CD26 in malignant pleural mesothelioma." British journal of cancer 110.9 (2014): 2232-2245.
Notice of Reasons for Refusal issued in JP 2017-538530 dated Sep. 29, 2020.
Office Action issued in the RU Application No. 2018112649, dated Jul. 30, 2020.
Notice of Reasons for Refusal issued in Japanese Application No. 2017-538530 dated Mar. 16, 2021.

* cited by examiner

| —— | control |
| --- | --- |
| ▬▬▬ | MSTO wt Y-TR1 1μg/ml |
| - - - - | MSTO clone12 Y-TR1 1μg/ml |
| -·-·- | MSTO clone12 Y-TR1 10μg/ml |
| — — — | MSTO clone12 Y-TR1 100μg/ml |

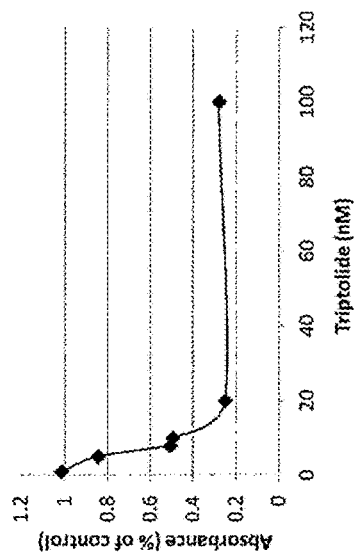
FIG. 3A
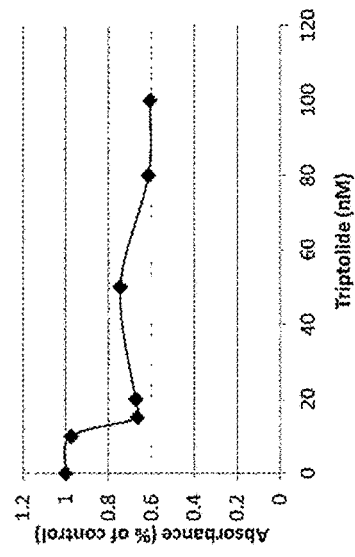
FIG. 3B
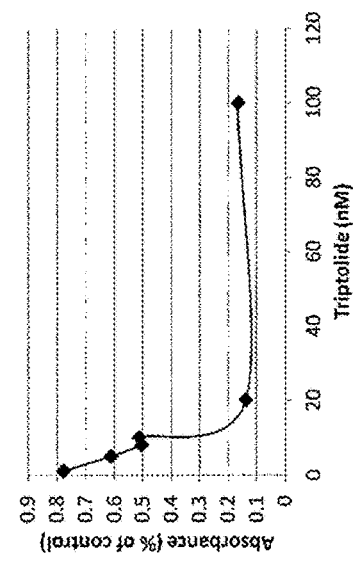
FIG. 3C
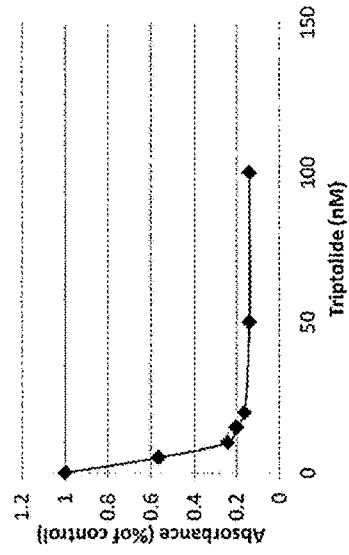
FIG. 3D
FIG. 3E

* p<0.05

Dose-response curves of cisplatin and pemetrexed

Combination effect of anti-CD26 antibody with Cis or PMT on MESO1 cell growth

Combination effect of anti-CD26 antibody with Cis or PMT on H2452 cell growth

Combination effect of anti-CD26 antibody with Cis-PMT regimen (in vitro)

Combination effect of anti-CD26 antibody with Cis or PMT on in vivo JMN growth

Combination effect of anti-CD26 antibody with Cis-PMT regimen on in vivo JMN growth

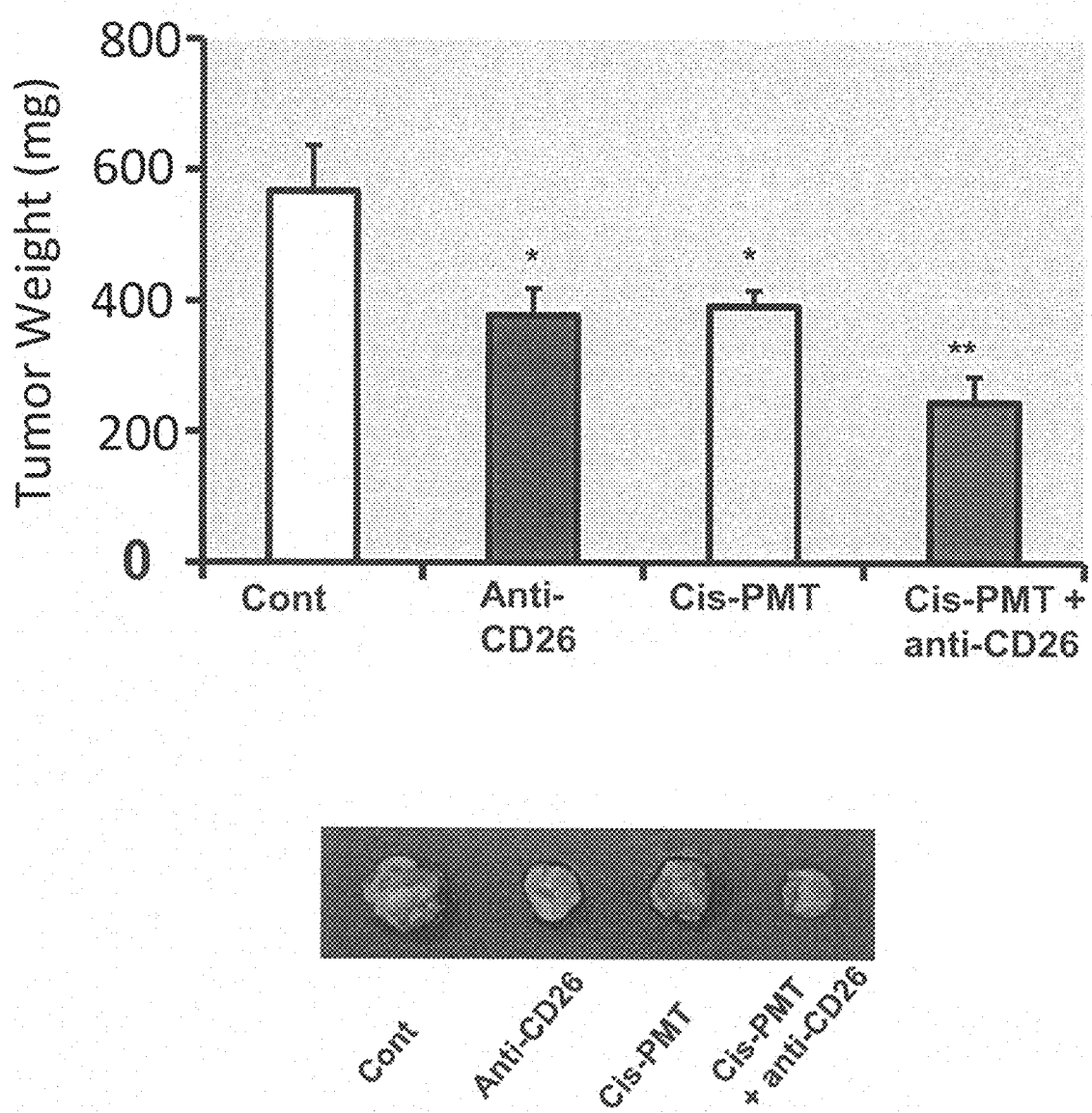

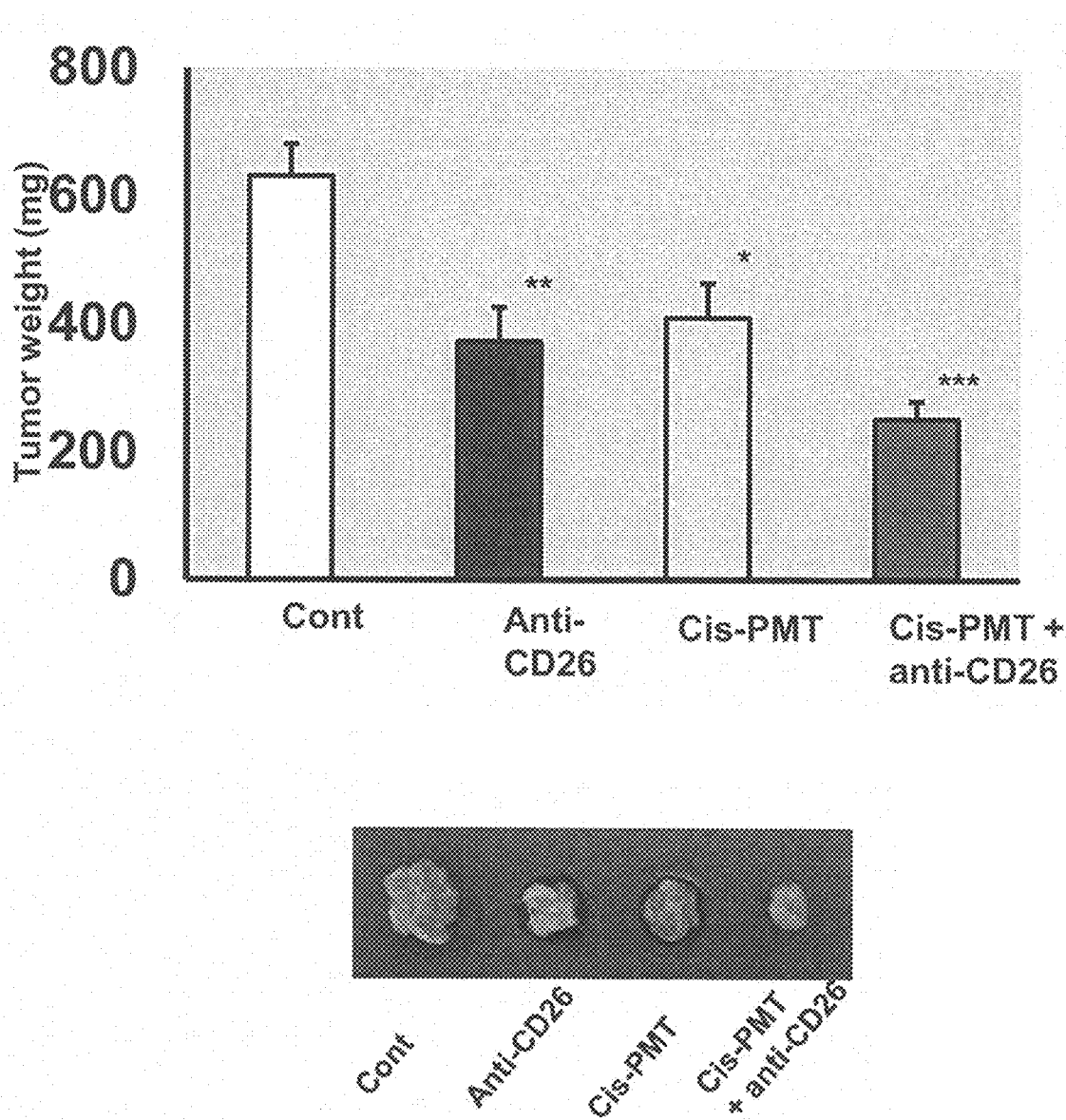

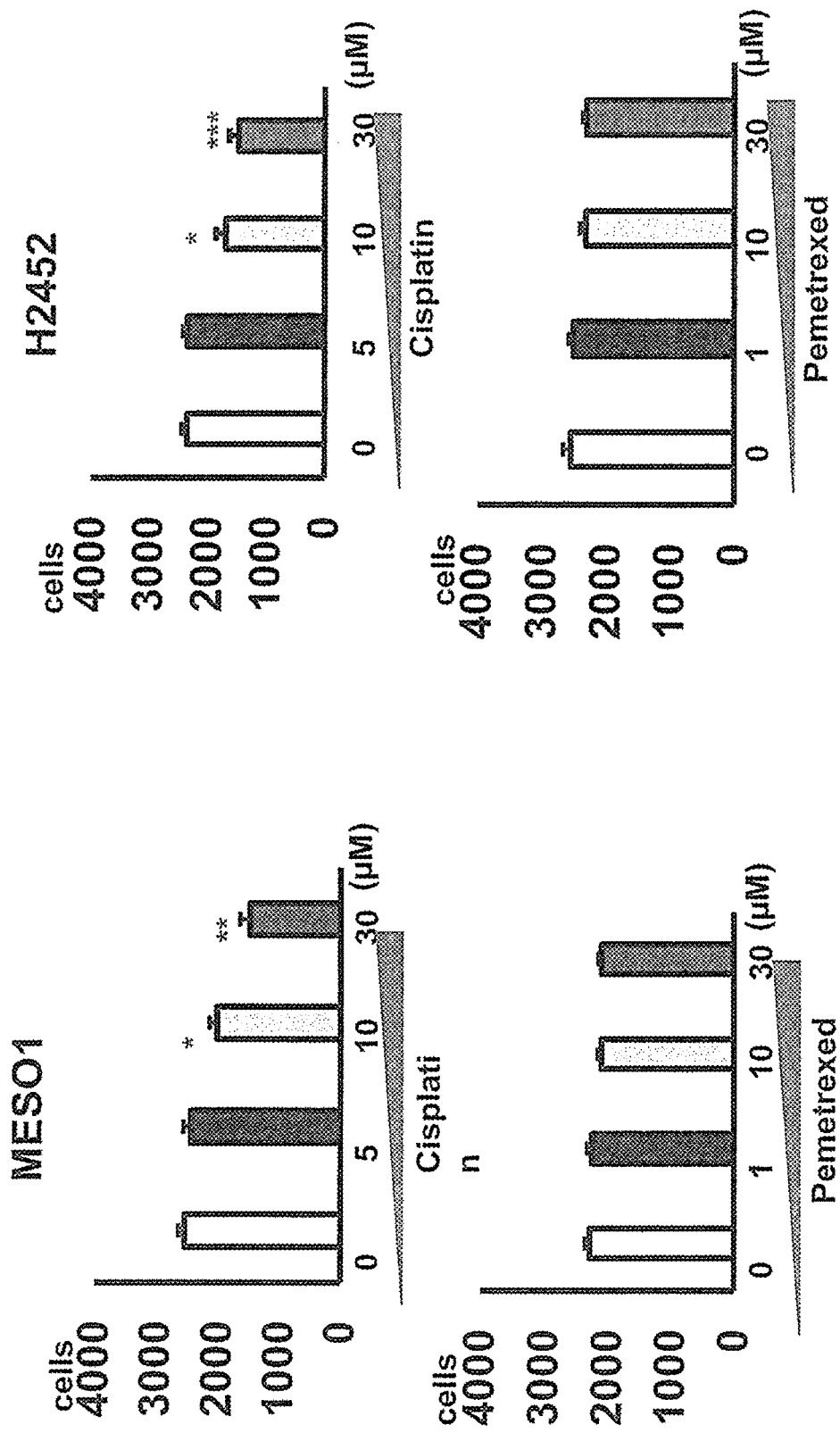

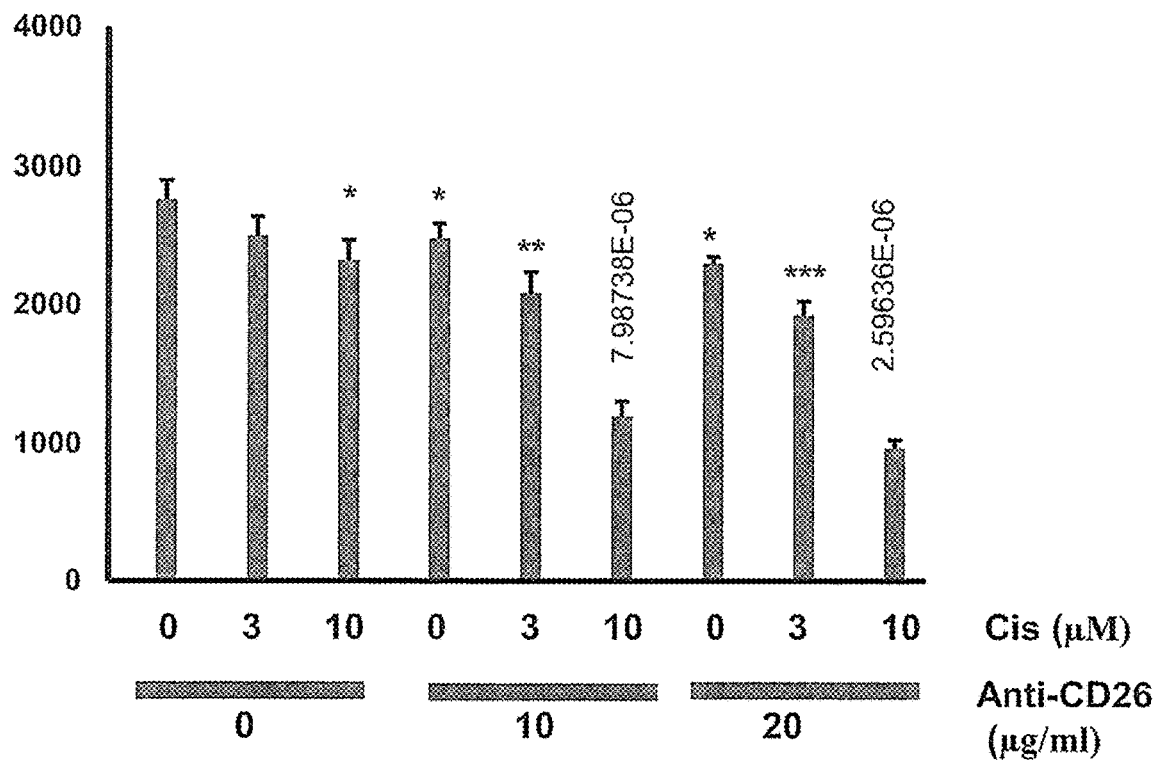

Interaction of Cis with anti-CD26

| Cis (µM) | Anti-CD26 (µg/ml) | Interaction |
|---|---|---|
| 10 | 10 | P<0.05 |
| 10 | 20 | P<0.05 |

Dose-response curve of gemcitabine for mesothelioma cell growth

| Gem (µM) | AntiCD26 (µg/ml) | Interaction |
|---|---|---|
| $10^{-8}$ | 3 | $P<0.05$ |

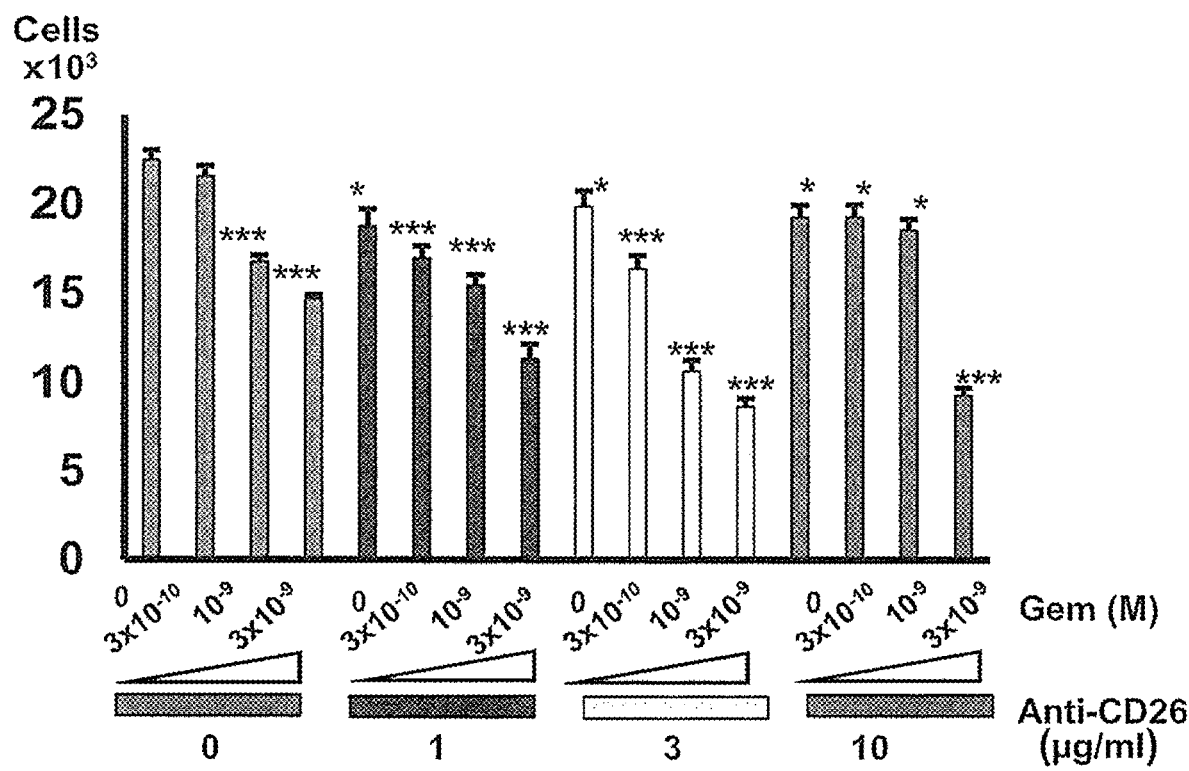

| Gem (µM) | AntiCD26 (µg/ml) | Interaction |
|---|---|---|
| $10^{-7}$ | 3 | $P<0.05$ |

| Gem (μM) | AntiCD26 (μg/ml) | Interaction |
|---|---|---|
| $10^{-8}$ | 3 | P<0.05 |
| $3 \times 10^{-8}$ | 3 | P<0.05 |
| $3 \times 10^{-9}$ | 10 | P<0.01 |

FIG. 28
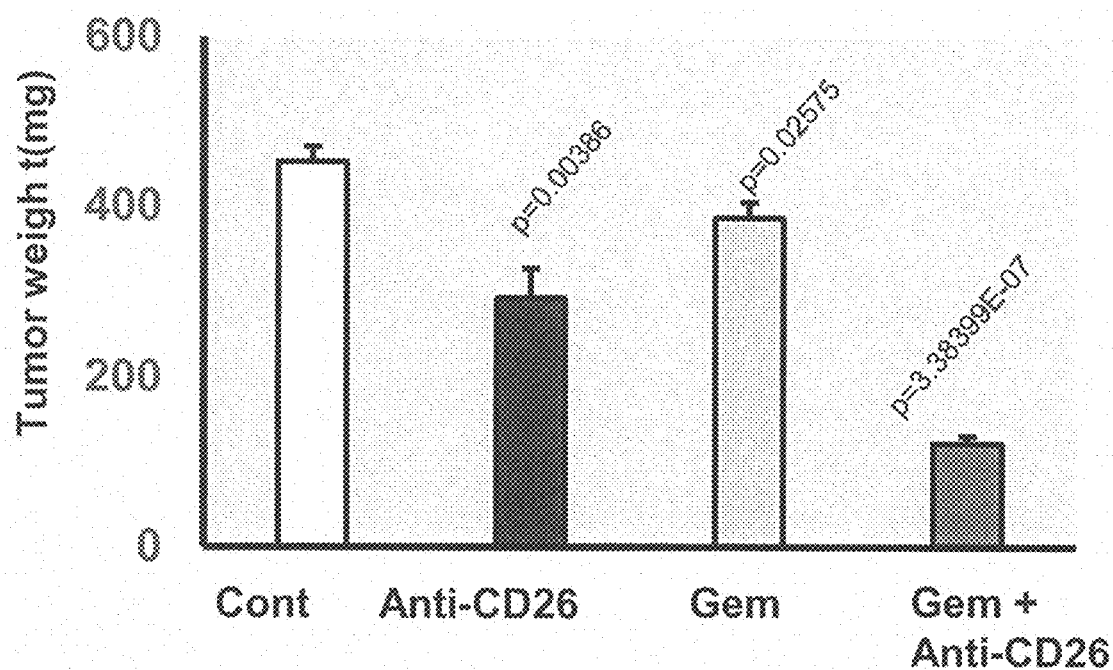
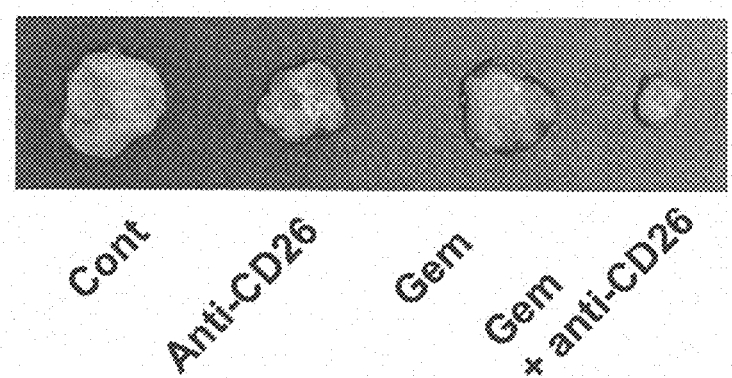

CANCER TREATMENT COMPOSITION COMBINING ANTI-CD26 ANTIBODY AND OTHER ANTICANCER AGENT

PRIORITY AND CROSS REFERENCE TO RELATED APPLICATIONS

The present application is the U.S. National Stage Application under 35 U.S.C. § 371 of International Application No. PCT/JP2016/076542, filed Sep. 9, 2016, designating the U.S. and published as WO 2017/043613 A1 on Mar. 16, 2017, which claims the priority from Patent Application No. 2015-179672 filed in Japan on 11 Sep. 2015, the whole contents of which are incorporated herein by reference in their entirety. The whole contents described in patents, patent applications and literatures cited herein are incorporated herein by reference in their entirety.

REFERENCE TO SEQUENCE LISTING

The present application includes an Electronic Sequence Listing. The Electronic Sequence Listing is provided as a file entitled NIPF003_001APC_SL, which is 31.0 KB in size, created on Jul. 17, 2021. The information in the Electronic Sequence Listing is incorporated herein by reference in its entirety.

TECHNICAL FIELD

The present invention relates to a composition for treatment of cancer, comprising an anti-CD26 antibody as an active ingredient, combined with other anticancer agents. The present invention also relates to the field of an antibody-drug conjugate (ADC).

BACKGROUND ART

It has been reported that, in the chemotherapy of mesothelioma, a single anticancer agent therapy exhibits drug responsiveness as low as 20% or less (Non Patent Literature 1). Accordingly, a plurality of drugs has been combined for more effective treatment of mesothelioma. For example, a combination use of cisplatin and pemetrexed have been reported to exert more excellent therapeutic effect than a use of each single drug alone (Non Patent Literature 2). For this reason, concomitant use of cisplatin and pemetrexed is currently applied to the standard chemotherapy of mesothelioma (Non Patent Literature 3). However, even with this concomitant therapy, the average survival period is only a little less than 12 months. Thus, it is required to develop more effective chemotherapy. Furthermore, concomitant therapy with cisplatin and pemetrexed suppress cancer cell growth by a mechanism involving cytotoxicity. There is a demand for therapy with lower adverse effect in patients, such as non-platinum-based treatment.

Gemcitabine is a nucleoside derivative of deoxycytidine, in which hydrogen at position 2' of the sugar chain is substituted with fluorine, which acts as an inhibition of DNA synthesis. This drug is excellent in safety (Non Patent Literature 4) and widely used as an anticancer agent. However, the effect of gemcitabine alone is insufficient on mesothelioma. Combination of gemcitabine with an appropriate anticancer agent is expected to lead development of more effective combination therapy. For example, since pemetrexed and gemcitabine has been already demonstrated to have an anticancer effect in single use, a combination therapy of these drugs has been attempted, but whose effect on the prolongation of an average survival period in the treatment of mesothelioma was only the same effect as single use of pemetrexed (Non Patent Literature 5). It has been further reported that, in comparing the treatment with cisplatin-pemetrexed combination to the treatment with cisplatin-gemcitabine combination, the cisplatin-pemetrexed combination treatment of mesothelioma was more excellent (Non Patent Literature 6). Also, in a combination of epirubicin and gemcitabine, the combination use hardly improved the effect (Non Patent Literature 7). Likewise, combination use of gemcitabine and a vinca alkaloid anti-malignant tumor agent vinorelbine has been reported not to improve the effect (Non Patent Literature 8). Accordingly, these previous trials on gemcitabine combination use were not succeeded in combination-derived improvement.

Concomitant use of docetaxel and gemcitabine is recognized to give a slight improvement in effect due to combination that prolongs an average survival period to 15 months (Non Patent Literature 9). Concomitant use of gemcitabine with an antifolate methotrexate has been reported to slightly prolong the average survival period to 19.4 months (Non Patent Literature 10). However, these anticancer agents combined with gemcitabine has a non-cell-selective activity and might therefore induce adverse effects.

Concomitant use has also been studied on cancers other than mesothelioma. For example, concomitant use of cisplatin-pemetrexed has an excellent effect on lung cancer (Non Patent Literature 11). An EGFR inhibitor gefitinib (Iressa) is also highly frequently used, and it is required to develop concomitant therapy using drugs other than cisplatin and gemcitabine.

Other strategy to enhance the therapeutic effect of cisplatin-pemetrexed concomitant therapy employs further combination with additional drugs. Since the standard therapy of mesothelioma causes anemia, erythropoietin may be administered, but erythropoietin does not potentiate the cytotoxic effect of combination of cisplatin-pemetrexed on mesothelioma cell lines (Non Patent Literature 12). It has been reported that a histone deacetylase (HDAC) inhibitor vorinostat does not prolong a life-extending effect, as compared with placebo, in mesothelioma patients (Non Patent Literature 13). A HDAC inhibitor valproate used as an anticonvulsant drug has been reported to potentiate the antitumor activity of cisplatin-pemetrexed concomitant use in experiments using mesothelioma cell lines (Non Patent Literature 14). However, valproate often causes adverse effects such as nausea or vomiting, and thus is considered not to be suited for administration to cancer patients who feel severe fatigue.

Combined use with genetic treatment has been attempted, and the transfection of cells with SOCS-1 gene has been reported to potentiate the cytotoxic effect of cisplatin-pemetrexed concomitant use in experiments using mesothelioma cell lines (Non Patent Literature 15). It is known that, in most of mesothelioma patients, p53 gene is normal but is inactivated due to deficiency in p14 (ARF) or p16 (INK4A). It has been reported that the p53 gene introduction into mesothelioma cell lines synergistically potentiated the cytotoxic effect of cisplatin or pemetrexed, and particularly that the introduction of p53 gene into pleura of mice which were transplanted mesothelioma intrapleurally potentiated the antitumor activity of cisplatin (Non Patent Literature 16). However, clinical treatment with gene transfer has difficulty at present and is complicated for practical use, and thus there is a demand for a more convenient and more effective method.

The expression of a vascular endothelial cell growth factor (VEGF) has been observed in most of mesothelioma biopsy, suggesting the possibility that VEGF is involved in the growth of mesothelioma. Accordingly, the effect of an anti-VEGF antibody bevacizumab on standard therapy has been studied in phase II clinical trials (Non Patent Literature 17). However, bevacizumab could not potentiate the therapeutic effect of the standard cisplatin-pemetrexed concomitant therapy. The addition of a low-molecular compound, a receptor tyrosine kinase (RTK) inhibitor, sunitinib to the standard cisplatin-pemetrexed concomitant therapy has been studied in 10 non-small cell cancer cases and 1 mesothelioma case in phase I clinical trials, but no medicinal interaction was observed (Non Patent Literature 18).

Interferon beta has been reported to synergistically enhance the cytotoxic activity of cisplatin or pemetrexed in experiments using mesothelioma cell lines (Non Patent Literature 19). This effect is probably based on p53 expression induced by interferon beta. However, in practical use, adverse effect such as fever or malaise associated with the administration of interferon beta may become a problem.

The clinical presentation of mesothelioma is characterized by pleural invasion (Non Patent Literature 20). Dyspnea is strongly manifested as a symptom due to accumulation of pleural effusion caused by pleural invasion. Although mesothelioma is characterized by invasion, activity against invasion has not been sufficiently analyzed. The aforementioned SOCS-1 gene introduction into mesothelioma cells has been reported to synergistically increase the anti-invasive activity of cisplatin-pemetrexed combination (Non Patent Literature 21). Mesothelin is a 40 kDa glycoprotein overexpressed in mesothelioma, pancreatic cancer, and ovary cancer, and has been reported to promote the invasion of mesothelioma cell lines (Non Patent Literature 22). However, there is no report on an effective drug of a low-molecular compound inhibitor of or an antibody against mesothelin. Pregnancy-associated plasma protein A (PAPPA) has also been reported to promote invasion in experiments using mesothelioma cell lines (Non Patent Literature 23). However, there is no report on an effective substance for treatment of mesothelioma targeting PAPPA.

Accordingly, there is no practically applicable treatment method that can solve the problems in the cisplatin-pemetrexed concomitant treatment of mesothelioma.

Antibody-drug conjugates are in a process of practical use as a targeting therapy, mainly for malignant tumors. Conjugation of an agent having an anticancer activity with an antibody which specifically binds to the tumor cells has advantages that the agent efficiently introduced into tumor cells as well as adverse effects due to toxicity on non-tumor cells are reduced. The antibody-drug conjugates are prepared by the following procedures: a mouse monoclonal antibody against an antigen which is specifically expressed on tumor cells is humanized by an in silico modeling technique, and a drug having a very high antitumor activity on the target tumor cells are selected, which is conjugated with the humanized antibody via a cross-linking agent. At present, two antibody-drug conjugates (indications: acute myeloid leukemia and malignant lymphoma) were approved as pharmaceuticals by United States FDA, and 35 antibody-drug conjugates are under clinical trial as of 2013. None of antibody-drug conjugate has been approved in Japan. Although the antibody-drug conjugates are promising as antitumor drugs in terms of both of potentiation of efficacy and reduction of adverse effects, only a few antibody-drug conjugates have been brought into practical use because multiple stages of investigation is required, such as (1) selection of an antigen and preparation of a monoclonal antibody having favorable specificity, (2) humanization of the antibody, (3) transfer of the antibody into tumor cells, (4) selection of a drug to be attached, (5) selection of a cross-linking agent, and (6) safety. Malignant mesothelioma is a disease with poor prognosis even by combined modality treatment and thus a development of a novel treatment method is demanded. However, no antibody-drug conjugate for malignant mesothelioma has been approved as a drug.

CD26 is a transmembrane protein and is a costimulatory molecule involved in the activation of T cells. High expression of CD26 in various malignant tumors including malignant mesothelioma has been revealed in recent years. Due to cancer specificity of CD26, antitumor effect of CD26 has been expected (Patent Literatures 1 and 2). Since CD26 is particularly overexpressed in mesothelioma (Non Patent Literature 24), an anti-CD26 antibody is considered to be highly safe. Actually, an anti-CD26 antibody suppresses the growth of mesothelioma cells (Non Patent Literature 25 and Patent Literature 3), and a humanized anti-CD26 antibody YS110 has already completed a phase I clinical trial in France, which has demonstrated its safety (Non Patent Literature 26). However, concomitant use of an anti-CD26 antibody with other drugs has not been reported.

CITATION LIST

Patent Literature

Patent Literature 1: International Publication No. WO02/14462
Patent Literature 2: International Publication No. WO2007/014169
Patent Literature 3: International Publication No. WO2008/114876

Non Patent Literature

Non Patent Literature 1: Ong T and Vogelzang N J, 1996
Non Patent Literature 2: Ellis P et al., 2006; Jaenne P A., 2006
Non Patent Literature 3: Vogelzang et al 2003, Stahel R A et al., 2010, Boons C. C. L. M., 2013
Non Patent Literature 4: Toschi L et al., 2005
Non Patent Literature 5: Janne P A et al., 2008
Non Patent Literature 6: Shukuya T et al., 2014
Non Patent Literature 7: Okuno S H et al., 2008
Non Patent Literature 8: Zauderer M G et al., 2014
Non Patent Literature 9: Ralli M et al., 2009
Non Patent Literature 10: Kuribayashi K et al., 2013
Non Patent Literature 11: Sun J M et al J Clin Oncol 33 (22) 2450 2015
Non Patent Literature 12: Palumbo C et al., 2008
Non Patent Literature 13: Zauderer and Krug, 2012
Non Patent Literature 14: Vandermeets F et al, 2009
Non Patent Literature 15: Iwahori H et al. 2013
Non Patent Literature 16: Li Q et al., 2012
Non Patent Literature 17: Dowell J E et al., 2012
Non Patent Literature 18: Camidge D R et al., 2013
Non Patent Literature 19: Li Q et al., 2013
Non Patent Literature 20: Robinson and Lake, 2005
Non Patent Literature 21: Iwamoto H et al., 2013
Non Patent Literature 22: Servais E L et al., 2012
Non Patent Literature 23: Huang J et al., 2013
Non Patent Literature 24: Amatya V J et al., 2011
Non Patent Literature 25: Inamoto T et al., 2007
Non Patent Literature 26: Angebin E et al
Non Patent Literature 27: Yamada K et al, Plos One, 2013 April 29; 8 (4): e62304

SUMMARY OF INVENTION

As described above, to solve the problems of the cisplatin-pemetrexed concomitant therapy, many studies such as combination with other drugs are currently underway on the standard chemotherapy of mesothelioma. However, their practical use faces lots of challenges. The antitumor effect of the standard cisplatin-pemetrexed concomitant therapy is based on a cytotoxic effect, and thus in adding a further drug to the standard therapy, the drug to be added is required not to be based on cytotoxicity and to be highly safe and more effective. There is a further demand for a novel highly safe treatment method that is not based on cytotoxicity, unlike the standard therapy, and is based on non-platinum therapy.

Although the pathological feature of mesothelioma is local invasion, few studies for mesothelioma drugs focused on the invasion. The inventors considered that a more effective treatment method could be provided by developing a method for treatment of mesothelioma focusing on an invasion inhibitory effect.

CD26 is overexpressed in mesothelioma and is considered to be highly safe. Actually, an anti-CD26 antibody suppresses the growth of mesothelioma cells and is therefore under phase I clinical trial on mesothelioma patients. Accordingly, the inventors have studied a treatment method using the standard cisplatin-pemetrexed concomitant therapy in combination with an anti-CD26 antibody for the growth and invasion of mesothelioma cell lines. As a result, it has been revealed that the suppression of mesothelioma growth by the standard cisplatin-pemetrexed concomitant therapy is potentiated when it is combined with the anti-CD26 antibody. The inventors have also found that the concomitant use of cisplatin and pemetrexed suppressed an invasion only slightly, whereas the combination of the anti-CD26 antibody with the cisplatin-pemetrexed concomitant use inhibited the invasion synergistically.

The inventors have further analyzed molecules involved in the enhancement of the invasion inhibitory effect using a microarray of anti-CD26 antibody-treated mesothelioma cells, and found the involvement of AAMP, ESAM, FUT8, RAC1, FYN, and RNF20.

The inventors have studied the combination effect of CD26 with various drugs, and found that a concomitant use of a humanized CD26 antibody and gemcitabine or gefitinib against the growth of mesothelioma cell lines can provide a highly effective and safe method for treating mesothelioma.

The inventors have further studied on antibody-drug conjugates using an anti-CD26 antibody. As a result, a novel antibody-drug conjugate (Y-TR1) showing very high effect on CD26-positive malignant mesothelioma cells has been successfully obtained by conjugating an anti-CD26 antibody (YS110) with triptolide which is known to have strong anti-tumor activity but has not been used as an antibody-drug conjugate, via a divalent cross-linking agent.

Accordingly, the present invention relates to a concomitant drug of an anti-CD26 antibody and an additional drug, and a conjugate comprising an anti-CD26 antibody linked to triptolide. More specifically, the present invention relates to the following aspects:

(1) A conjugate comprising an anti-CD26 antibody or a fragment thereof linked to triptolide.
(2) The conjugate of (1), wherein the anti-CD26 antibody or the fragment thereof is a humanized antibody or a fragment thereof.
(3) The conjugate of (2), wherein the humanized antibody or the fragment thereof comprises a heavy chain variable region comprising an amino acid sequence having 80% or more identity to an amino acid sequence selected from the group consisting of SEQ ID NOs: 8 to 14, and a light chain variable region comprising an amino acid sequence having 80% or more identity to an amino acid sequence selected from the group consisting of SEQ ID NOs: 1 to 7.
(4) The conjugate of (2) or (3), wherein the humanized antibody or the fragment thereof comprises a heavy chain variable region comprising an amino acid sequence having 80% or more identity to an amino acid sequence selected from the group consisting of SEQ ID NOs: 1 to 7, and a light chain variable region comprising an amino acid sequence having 80% or more identity to an amino acid sequence selected from the group consisting of SEQ ID NOs: 8 to 14.
(5) The conjugate of any one of (2) to (4), wherein the humanized antibody or the fragment thereof comprises at least one heavy chain comprising an amino acid sequence having 90% or more sequence identity to the amino acid sequence of SEQ ID NO: 17, and at least one light chain comprising an amino acid sequence having 90% or more sequence identity to the amino acid sequence of SEQ ID NO: 18.
(6) The conjugate of any one of (2) to (5), wherein the humanized antibody or the fragment thereof comprises at least one heavy chain comprising an amino acid sequence from position 20 to position 465 of the amino acid sequence of SEQ ID NO: 17, and at least one light chain comprising an amino acid sequence from position 21 to position 234 of the amino acid sequence of SEQ ID NO: 18.
(7) The conjugate of any one of (2) to (6), wherein the humanized antibody or the fragment thereof binds to one or more peptides selected from the group consisting of SEQ ID NOs: 19 to 28.
(8) The conjugate of (2), wherein the humanized antibody is produced by a strain designated as s604069.YST-pABMC148 (x411) under deposition No. PTA-7695 of the American Type Culture Collection (ATCC).
(9) The conjugate of any one of (1) to (8), wherein the fragment is selected from the group consisting of Fab, Fab', Fab'-SH, Fv, scFv, and F(ab')2.
(10) A pharmaceutical composition comprising a conjugate of any one of (1) to (9) as an active ingredient.
(11) The pharmaceutical composition of (10) for the treatment of malignant mesothelioma.
(12) A malignant mesothelioma cell growth inhibitor comprising a conjugate of any one of (1) to (9).
(13) A malignant mesothelioma cell lysing agent comprising a conjugate of any one of (1) to (9).
(14) Use of a conjugate of any one of (1) to (9) in the manufacture of a pharmaceutical composition for the treatment of malignant mesothelioma.
(15) A pharmaceutical composition comprising an anti-CD26 antibody or a fragment thereof and an additional antitumor agent.
(16) The pharmaceutical composition of (15), wherein the additional antitumor agent is one or more drugs selected from the group consisting of cisplatin, pemetrexed, gefitinib, and gemcitabine.
(17) The pharmaceutical composition of (15) or (16), wherein the anti-CD26 antibody or the fragment thereof is a humanized antibody or a fragment thereof.
(18) The pharmaceutical composition of (17), wherein the humanized antibody or the fragment thereof comprises a heavy chain variable region comprising an amino acid sequence which have 80% or more identity to an amino acid sequence selected from the group consisting of SEQ ID NOs: 8 to 14, and a light chain variable region comprising an amino acid sequence which have 80% or more identity to an amino acid sequence selected from the group consisting of SEQ ID NOs: 1 to 7.

(19) The pharmaceutical composition of (17), wherein the humanized antibody or the fragment thereof comprises a heavy chain variable region comprising an amino acid sequence which have 80% or more identity to an amino acid sequence selected from the group consisting of SEQ ID NOs: 1 to 7, and a light chain variable region comprising an amino acid sequence which have 80% or more identity to an amino acid sequence selected from the group consisting of SEQ ID NOs: 8 to 14.

(20) The pharmaceutical composition of (17), wherein the humanized antibody or the fragment thereof comprises at least one heavy chain comprising an amino acid sequence which have 90% or more identity to the amino acid sequence of SEQ ID NO: 17, and at least one light chain comprising an amino acid sequence which have 90% or more identity to the amino acid sequence of SEQ ID NO: 18.

(21) The pharmaceutical composition of (17), wherein the humanized antibody or the fragment thereof comprises at least one heavy chain comprising an amino acid sequence from position 20 to position 465 of the amino acid sequence of SEQ ID NO: 17, and at least one light chain comprising an amino acid sequence from position 21 to position 234 of the amino acid sequence of SEQ ID NO: 18.

(22) The pharmaceutical composition of any one of (17) to (21), wherein the humanized antibody or the fragment thereof binds to one or more peptides selected from the group consisting of SEQ ID NOs: 19 to 28.

(23) The pharmaceutical composition of any one of (17) to (22), wherein the humanized antibody is produced by a strain designated as s604069.YST-pABMC148 (x411) with deposition No. PTA-7695 of the American Type Culture Collection (ATCC).

(24) The pharmaceutical composition of any one of (15) to (23), wherein the fragment is selected from the group consisting of Fab, Fab', Fab'-SH, Fv, scFv, and F(ab')2.

(25) The pharmaceutical composition of any one of (15) to (24) for the treatment of malignant mesothelioma.

(26) A malignant mesothelioma cell growth inhibitor comprising a pharmaceutical composition of any one of (15) to (24).

(27) A malignant mesothelioma cell lysing agent comprising a pharmaceutical composition of any one of (15) to (24).

(28) Use of an anti-CD26 antibody and an additional antitumor agent in the manufacture of a pharmaceutical composition for the treatment of malignant mesothelioma.

(29) The use of (28), wherein the additional antitumor agent is one or more drugs selected from the group consisting of cisplatin, pemetrexed, gefitinib, and gemcitabine.

The combination of a humanized CD26 antibody with one or more drugs selected from the group consisting of cisplatin, pemetrexed, gefitinib, and gemcitabine synergistically potentiates a inhibitory effect on invasion which is the pathological feature and radical problem of mesothelioma, and/or enhances an inhibitory effect on mesothelioma cell growth, and thus, is considered to be very useful in the treatment of mesothelioma. Because concomitant use of gefitinib or gemcitabine and an anti-CD26 antibody is non-platinum therapy, can be highly safe medication therapy of mesothelioma. Moreover, the humanized anti-CD26 antibody conjugated with triptolide can effectively suppress the growth of malignant mesothelioma cells in a smaller amount of triptolide. Accordingly, a lower toxic and highly effective anti-malignant tumor agent can be provided.

BRIEF DESCRIPTION OF DRAWINGS

FIG. 1 is a graph of the intact masses of unconjugated YS110 and Y-TR1 (SMCC) measured by MALDI-TOFF mass spectrometry.

FIG. 3 is a graph of toxicity of triptolide to malignant mesothelioma and T-cell leukemia cell lines. A: wild-type MSTO (wt); B: MSTO clone 12; C: JMN; D: Jurkat CD26 (−); E: Jurkat CD26(+). The ordinate indicates fluorescence intensity (%) vs. control, and the abscissa indicates the concentration (nM) of triptolide.

FIG. 10 is a graph showing the MESO1 growth inhibitory effect of combination use of YS110 with cisplatin (Cis) or pemetrexed (PMT).

FIG. 11 is a graph of the H2452 growth inhibitory effect of combination use of YS110 with cisplatin (Cis) or pemetrexed (PMT).

FIG. 12 is a graph of the growth inhibitory combination use of cisplatin (Cis)-pemetrexed (PMT) concomitant use with YS110.

FIG. 15 is a graph and a photograph showing the effect of YS110 on inhibition of in vivo MESO1 cell growth by cisplatin-pemetrexed concomitant use. In the graph, the ordinate indicates a tumor weight (mg), and the abscissa indicates the administered drug. The photograph shows excised tumor samples. $*p<0.05$, $**p<0.01$.

FIG. 16 is a graph and a photograph showing the effect of YS110 on inhibition of in vivo H2452 cell growth by cisplatin (Cis)-pemetrexed (PMT) concomitant use. In the graph, the ordinate indicates a tumor weight (mg), and the abscissa indicates the administered drug. The photograph shows excised tumor samples. $*p<0.05$, $p<0.01$, $*p<0.001$.

FIG. 17 is a graph showing the activity of cisplatin (Cis) or pemetrexed (PMT) on cell invasion. The ordinate indicates the number of invasive cells, and the abscissa indicates the concentration (μM) of each drug. The left graphs show results of using MESO1 cells, and the right graphs show results of using H2452 cells. The upper graphs show results of cisplatin, and the lower graphs show results of pemetrexed. $*p<0.05$, $p<0.01$, $*p<0.001$.

FIG. 19A is a graph showing the MESO1 cell invasion inhibitory effect of combination use of YS110 and cisplatin (Cis). The ordinate indicates the number of invasive cells, and the abscissa indicates the concentration (μM) of each drug. $*p<0.05$, $p<0.01$, $*p<0.001$. FIG. 19B is a table of the analyzed interaction of cisplatin with YS110 for a MESO1 cell invasion inhibitory effect.

FIG. 23A is a graph of the effect of combination use of YS110 and gemcitabine (Gem) on sarcomatoid mesothelioma JMN cell growth. The ordinate indicates the number of cells ($\times 10^3$ cells), and the abscissa indicates the amount of each drug administered. $*p<0.05$, $p<0.01$, $*p<0.001$. FIG. 23B is a table of analyzed interaction of gemcitabine with YS110 for a JMN cell growth inhibitory effect.

FIG. 28 is a graph and a photograph showing the effect of combination use of YS110 with gemcitabine on the in vivo growth of sarcomatoid mesothelioma JMN cells, and a table of the interaction of gemcitabine with YS110. In the graph, the ordinate indicates a tumor weight (mg), and the abscissa indicates the administered drug. The photograph shows excised tumor samples.

FIG. 32 is a graph comparing the growth inhibitory effects of cisplatin and pemetrexed for MESO1 cells and JMN cells. The ordinate indicates the rate of growth inhibition (%), and the abscissa indicates the concentration (M) of each drug.

FIG. 33 is a graph of gemcitabine's growth inhibitory effect comparing MESO1 cells and JMN cells, and comparing H2452 cells and H226 cells.

DETAILED DESCRIPTION

1. Antibody

Figure 1A:
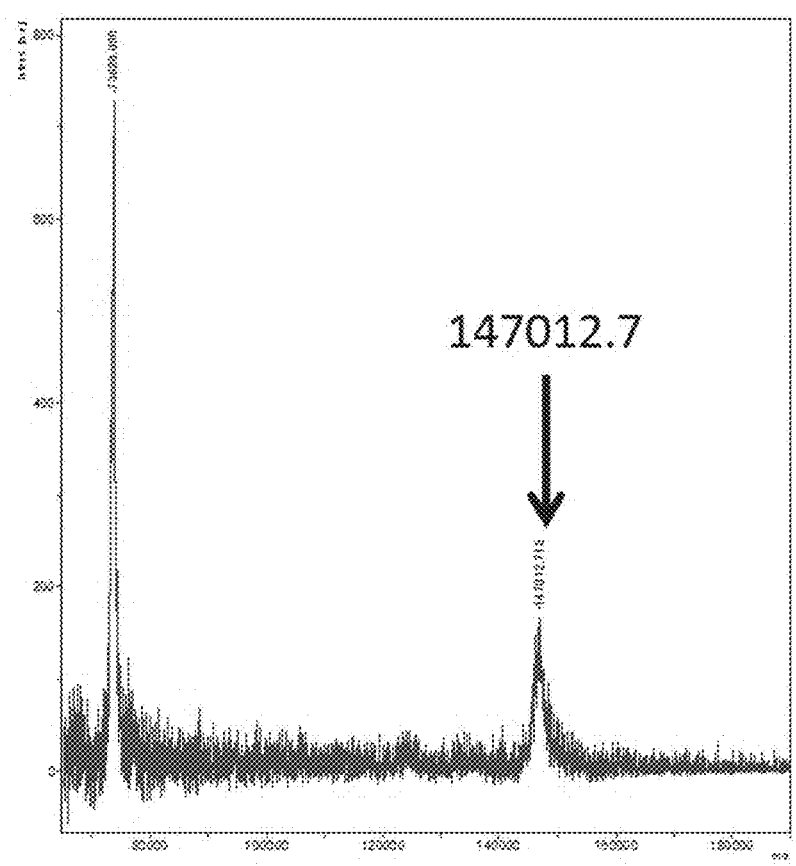
FIG. 1A shows unconjugated YS110 (measured value: 147012.7)

The term "antibody" herein is an immunoglobulin molecule capable of specifically binding to a target such as a carbohydrate, a polynucleotide, a lipid, or an antibody via at least one antigen recognition site in variable regions of the immunoglobulin molecule. The antibody used herein includes a complete polyclonal antibody or monoclonal antibody as well as a fragment thereof (Fab, Fab', F(ab')2, Fv, etc.), a single-chain variable fragment (scFv), their variants, a fusion protein containing an antibody moiety, and other modified structures of an immunoglobulin molecule containing an antigen recognition site. The antibody can be any class of antibody such as IgG, IgA, or IgM (or subclass thereof) and does not need to be of particular class. Immunoglobulins are divided into different classes according to the amino acid sequences of heavy chain constant domains of the antibody. Typical five immunoglobulin classes are IgA, IgD, IgE, IgG and IgM, some of which may be further subdivided into subclasses (isotypes), for example, IgG1, IgG2, IgG3, IgG4, IgA1 and IgA2. The corresponding heavy chain constant domains of immunoglobulins of different classes are called $\alpha$, $\delta$, $\epsilon$, $\gamma$ and $\mu$, respectively. The respective subunit structures and three-dimensional structures are well known for the immunoglobulins of different classes.

The "monoclonal antibody" described herein refers to an antibody obtained from a cell population producing substantially homogeneous antibodies. Specifically, individual antibodies contained in the cell population are identical except for natural mutants that might slightly possibly be present. The monoclonal antibody is directed to a single antigen site and is very specific. In contrast to a typical polyclonal antibody against different antigens targeting different antigenic determinants (epitopes), each monoclonal antibody targets a single antigenic determinant of an antigen. The modifier "monoclonal" refers to the properties of the antibody obtained from the cell population producing substantially homogeneous antibodies and should not be interpreted as requiring particular antibody production method. The monoclonal antibody used according to the present invention can be prepared by a recombinant DNA method as described in, for example, U.S. Pat. No. 4,816,567. The monoclonal antibody can also be isolated from a phage library prepared using a technique described in, for example, McCafferty et al., 1990, Nature, 348: 552-554.

The "humanized" antibody used herein refers to a form of a nonhuman (e.g., mouse) antibody that is a specific chimeric immunoglobulin or a fragment thereof containing an immunoglobulin chain or a nonhuman immunoglobulin-derived minimum sequence (Fv, Fab, Fab', F(ab')2, or other antigen binding partial sequences of an antibody, etc.). Some humanized antibodies are human immunoglobulins (recipient antibodies) in which complementarity determining region (CDR)-derived residues of a recipient are replaced with CDR-derived residues of a nonhuman species (donor antibody) such as a mouse, a rat or a rabbit having the desired specificity, affinity and ability. In some cases, Fv framework region (FR) residues of the human immunoglobulin are replaced with the corresponding nonhuman-derived residues. Some humanized antibodies contain at least one, usually two variable regions derived from a nonhuman species (donor antibody) such as, a mouse, a rat or a rabbit having the desired specificity, affinity and/or ability, and one or more Fv framework region residues and/or one or more Fv CDR residues are replaced with the corresponding human residues (i.e., human antibody sequence-derived residues). Most generally, at least a plurality of Fv framework region residues may be replaced in one or more variable regions of the humanized antibody. The humanized antibody may further contain a residue that is found neither in the recipient antibody nor in the grafted CDR or framework sequence and may contain a residue for further improving and optimizing antibody performance.

Some humanized antibodies contain substantially the whole of at least one, generally two variable regions. In these variable regions, all or substantially all CDRs correspond to nonhuman immunoglobulin CDRs, and all or substantially all FRs are FRs of human immunoglobulin consensus sequences. Some humanized antibodies contain substantially the whole of at least one, generally two variable regions. In these variable regions, a great majority of CDR amino acid residues are derived from non-human immunoglobulin CDRs, and one or more FR amino acid residues are derived from FRs of human immunoglobulin consensus sequences. Most preferably, the humanized antibody may contain at least a portion of a human immunoglobulin constant region (Fc) or domain (generally, a human immunoglobulin). Some humanized antibodies have a modified Fc region as described in International Publication No. WO99/58572. Some forms of the humanized antibody have one or more (e.g., 1, 2, 3, 4, 5, or 6) CDRs altered from the original antibody. These CDRs are also called one or more CDRs "derived" from one or more CDRs of the original antibody.

The "variable region" of an antibody refers to antibody light chain or heavy chain variable regions each alone or in combination. The heavy chain and light chain variable regions are each composed of four framework regions (FRs) linked by three complementarity determining regions (CDRs) also known as hypervariable regions. CDRs in each chain are kept in close proximity by FRs and contribute to the formation of an antigen binding site of the antibody, together with CDRs of the other chain. At least two techniques are used for determining CDRs: (1) an approach based on sequence variability between different species (e.g., Kabat et al., Sequences of Proteins of Immunological Interest, (5th ed., 1991, National Institutes of Health, Bethesda Md.)); and (2) an approach based on crystallographic research on antigen-antibody complexes (Al-Lazikani et al., (1997) J. Molec. Biol. 273: 927-948)). The combination of these two approaches is sometimes used in the art for determining CDRs.

The "constant region" of an antibody refers to antibody light chain or heavy chain constant regions each alone or in combination.

The term epitope "specifically binding to" an antibody is fully understood in the art, and methods for determining specific binding are also well known in the art. When a molecule reacts or mutually acts with a particular cell or substance more frequently, more rapidly, for a longer duration, and/or with larger affinity as compared with its reaction or mutual action with other cells or substances, the molecule is regarded as exhibiting "specific binding". When an antibody binds to a target with larger affinity or binding activity, more promptly, and/or for a longer duration as compared with its binding to other substances, the antibody "specifically binds to" the target. For example, an antibody specifically binding to one CD26 epitope is an antibody binding to this CD26 epitope with larger affinity or binding activity, more promptly, and/or for a longer duration as compared with its binding to other CD26 epitopes or non-CD26 epitopes. It should be understood from this definition that, for example, an antibody (or a moiety or an epitope) specifically binding to a first target may or may not specifically bind to a second target. Thus, the "specific binding" does not necessarily require (albeit can include) exclusive binding.

The "host cell" includes each individual cell or a cell culture that may serve as a recipient of a vector for the incorporation of a polynucleotide insert, or has already been the recipient. The host cell includes a progeny of a single host cell. The progeny is not necessarily required to be identical to an original parent cell (morphologically or in genomic DNA complements) due to natural, accidental or planned mutation. The host cell includes a cell transfected in vivo with the polynucleotide of the present invention.

The "isolated" antibody, antibody, polynucleotide, vector, cell, or composition is an antibody, an antibody, a polynucleotide, a vector, a cell, or a composition in a form that is not found naturally. The isolated antibody, antibody, polynucleotide, vector, cell, or composition includes that purified into a form no longer found naturally. In a certain embodiment, the isolated antibody, polynucleotide, vector, cell, or composition is substantially pure.

The "treatment" used herein is an approach for obtaining beneficial or desired clinical results. The beneficial or desired clinical results for the object of the present invention include, but are not limited to, the alleviation of one or more symptoms, decrease in the extent of a disease, a stabilized (i.e., non-aggravated) state of the disease, delay or slowdown of disease progression, recovery from or remission of the disease state, and relief (partial or whole), regardless of being detectable or not detectable. The "treatment" also means increase in the life expectancy of a patient with respect to the potential life expectancy of the patient without the treatment.

The "effective amount" is an amount sufficient for achieving beneficial or desired clinical results including clinical results. The effective amount can be administered at one or more dosages. The effective amount of an anti-CD26 antibody conjugate, an anti-CD26 antibody and an additional anticancer agent, or the like described herein for the object of the present invention is an amount sufficient for delaying the progression of a condition associated with tumor growth. As understood in the art, for example, the effective amount of the anti-CD26 antibody conjugate or the anti-CD26 antibody and the additional anticancer agent may vary according to or depend on, particularly, other factors such as the medical history of a patient and the type (and/or amount) of the anti-CD26 antibody conjugate or the additional anticancer agent used.

The "pharmaceutically acceptable carrier" or the "pharmaceutically acceptable excipient" used herein includes any material that is capable of maintaining the biological activity of an active ingredient when combined with the active ingredient, is unreactive with the immune system of a test subject when delivered, and is nontoxic to the test subject. Examples thereof include, but are not limited to, every standard pharmaceutical carrier including phosphate-buffered saline, water, emulsions such as oil/water emulsions, and various types of humectants. A preferred diluent for spray administration or parenteral administration is phosphate-buffered saline or physiological saline (0.9%). A composition containing such a carrier is formulated by a well-known conventional method (see e.g., Remington's Pharmaceutical Sciences, 18th edition, A. Gennaro ed., Mack Publishing Co., Easton, Pa., 1990; and Remington, The Science and Practice of Pharmacy 20th Ed. Mack Publishing, 2000).

Anti-CD26 Antibody

In a certain embodiment, the anti-CD26 antibody used herein specifically binds to human CD26. In a certain embodiment, the anti-CD26 antibody described herein binds to the same epitope as that for a mouse monoclonal antibody 14D10. In a certain embodiment, the anti-CD26 antibody described herein has the ability to block the binding of the mouse monoclonal antibody 14D10 to human CD26 (competes with the mouse monoclonal antibody 14D10) in competitive assay. In a certain embodiment, the anti-CD26 antibody described herein has the ability to block the binding of a mouse monoclonal antibody 1F7 to human CD26 (competes with the mouse monoclonal antibody 1F7) in competitive assay. The competitive assay can be performed by contacting a test antibody with an immobilized epitope or antigen, then washing off unbound antibodies, subsequently contacting a labeled 14D10 antibody or 1F7 antibody with the epitope or antigen, and washing off unbound antibodies, followed by the detection of the bound 14D10 antibody or 1F7 antibody. When the binding of the 14D10 antibody or the 1F7 antibody to the epitope or the antigen contacted with the test antibody is decreased as compared with the binding of the 14D10 antibody or the 1F7 antibody to a control epitope or antigen without contact with the test antibody, the test antibody can be confirmed to have the ability to block the binding of the 14D10 antibody or the 1F7 antibody (to compete with the 14D10 antibody or the 1F7 antibody) in the competitive assay.

Examples of the binding affinity of the anti-CD26 antibody used herein for human CD26 include affinity having a dissociation constant (i.e., Kd) of less than $10^{-5}$ M, less than $5 \times 10^{-5}$ M, less than $10^{-6}$ M, less than $5 \times 10^{-7}$ M, less than $10^{-7}$ M, less than $5 \times 10^{-8}$ M, less than $10^{-8}$ M, less than $5 \times 10^{-9}$ M, less than $10^{-9}$ M, less than $5 \times 10^{-10}$ M, less than $10^{-10}$ M, less than $5 \times 10^{-11}$ M or less than $10^{-11}$ M. The dissociation constant may also be $10^{-15}$ M or more, $5 \times 10^{-15}$ M or more, $10^{-14}$ M or more, $5 \times 10^{-14}$ M or more, $10^{-13}$ M or more, $5 \times 10^{-13}$ M or more, $10^{-12}$ M or more, $5 \times 10^{-12}$ M or more, $10^{-11}$ M or more, $5 \times 10^{-11}$ M or more, $10^{-10}$ M or more or $5 \times 10^{-10}$ M or more. Methods for determining affinity are known in the art. The binding affinity may be determined using, for example, a BIAcore biosensor, a KinExA biosensor, scintillation proximity assay, ELISA, ORIGEN immunoassay (IGEN International, Inc.), fluorescence quenching, fluorescence transfer, and/or yeast display. The affinity may be screened using appropriate bioassay.

One method for determining the binding affinity of an antibody against CD26 is the measurement of the affinity of a monofunctional Fab fragment of the antibody. To obtain the monofunctional Fab fragment, the antibody, for example, IgG, can be cleaved with papain or expressed by a recombination technique. The affinity of the anti-CD26 Fab fragment of a monoclonal antibody can be determined using a surface plasmon resonance (SPR) system (BIAcore 3000™, BIAcore Inc., Piscataway, N.J.). A SA (streptavidin) chip is used according to the supplier's instruction manual. Biotinylated CD26 can be diluted with HBS-EP (100 mM HEPES pH 7.4, 150 mM NaCl, 3 mM EDTA, 0.005% P20) and injected at a concentration of 0.005 mg/mL onto the chip. Two ranges of antigen density are achieved using a variable flow time across the individual chip channels: 10 to 20 response units (RU) for detailed kinetic tests and 500 to 600 RU for concentrations. A mixture of Pierce elution buffer solution and 4 M NaCl (2:1) effectively removes the bound Fab while keeping the activity of CD26 on the chip for 200 or more injections. A HBS-EP buffer solution can be used as a running buffer solution in all the BIAcore assays. Serial dilutions (0.1 to 10× estimated KD) of the purified Fab sample are injected at 100 µL/min for 2 minutes, and a dissociation time up to 30 minutes is usually acceptable. The concentration of the Fab protein can be determined by ELISA and/or SDS-PAGE electrophoresis using standard Fab having a known concentration (determined by amino acid analysis). An association rate (kon) and a dissociation rate (koff) of a reaction rate are obtained at the same time by using BIAevaluation program and fitting the data to a 1:1 Langmuir binding model (Lofas & Johnsson, 1990). An equilibrium dissociation constant (KD) value is calculated as koff/kon.

In a certain embodiment, the present invention relates to an anti-CD26 antibody-triptolide conjugate or a pharmaceutical composition containing an anti-CD26 antibody and an additional anticancer agent, which inhibits the growth of CD26 expressing cells. The present invention also encompasses an embodiment in which the conjugate or the composition is useful in the treatment of a condition (disease or disorder, etc.) associated with CD26 expression, for example, malignant mesothelioma. In a certain embodiment, the conjugate or the composition of the present invention may have one or more features from: (a) binding to CD26, (b) regulating CD26 activity, (c) arresting the cell cycle of CD26+ cells at the G1/S checkpoint, (d) inhibiting the growth of cells expressing CD26 (e.g., malignant mesothelioma cells), (e) inhibiting the binding of CD26 to extracellular matrix, and/or (f) being useful in the treatment of a condition associated with CD26 expression. In a certain embodiment, the condition associated with CD26 expression is a disease or a disorder associated with overexpression of CD26. In a certain embodiment, the condition associated with CD26 expression is mediated at least partially by CD26. In a certain embodiment, the condition associated with CD26 expression is a condition associated with the growth of cells expressing CD26. In a certain embodiment, the disease or the disorder is a cancer (e.g., malignant mesothelioma, lung cancer, kidney cancer, liver cancer or other malignant tumors involving the expression of CD26).

In a certain embodiment, the antibody contained in the conjugate or the composition of the present invention comprises both a heavy chain variable region comprising an amino acid sequence having at least approximately 80% identity to an amino acid sequence selected from the group consisting of SEQ ID NOs: 8 to 14, and a light chain variable region comprising an amino acid sequence having at least approximately 80% identity to an amino acid sequence selected from the group consisting of SEQ ID NOs: 1 to 7. In a certain embodiment, the antibody contained in the conjugate or the composition of the present invention comprises a light chain variable region comprising an amino acid sequence having at least approximately 80% identity to an amino acid sequence selected from the group consisting of SEQ ID NOs: 8 to 14, and a heavy chain variable region comprising an amino acid sequence having at least approximately 80% identity to an amino acid sequence selected from the group consisting of SEQ ID NOs: 1 to 7.

In a certain embodiment, the antibody contained in the conjugate or the composition of the present invention comprises at least 5 consecutive amino acids, at least 8 consecutive amino acids, at least approximately 10 consecutive amino acids, at least approximately 15 consecutive amino acids, at least approximately 20 consecutive amino acids, at least approximately 30 consecutive amino acids, or at least approximately 50 consecutive amino acids of an amino acid sequence of any one of SEQ ID NOs: 1 to 14.

The present invention further provides an anti-CD26 antibody-triptolide conjugate or a pharmaceutical composition containing an anti-CD26 antibody and an additional anticancer agent, which includes a fragment of the antibody sequence described herein (e.g., any one of SEQ ID NOs: 1 to 7, SEQ ID NOs: 8 to 14, SEQ ID NO: 15, and SEQ ID NO: 16). In a certain embodiment, the antibody includes a fragment of the antibody sequence described herein, having a length of at least approximately 50 amino acids, at least approximately 75 amino acids, or at least approximately 100 amino acids.

SEQ ID NO: 15
EVQLVX1SGX2X3X4X5QPGX6X7LRLX8CX9ASGX10X11LX12TYGVH

WVRQAPGKGLEWX13GVIWGX14GRTDYDX15X16FMSRVTISX17DX18

SKX19I X20YLQX21NSLRAEDTAVYYCX22RX23RHDWFDYWGQGTTVT

VSS

In the sequence described above, X1 is E or Q, X2 is A or G, X3 is G or E, X4 is L or V, X5 is V, K, or E, X6 is G or E, X7 is T or S, X8 is T or S, X9 is T or K, X10 is F or Y, X11 is S or T, X12 is T, N, or S, X13 is V or M, X14 is G or D, X15 is A or S, X16 is A or S, X17 is K or R, X18 is N or T, X19 is S or N, X20 is V or A, X21 is M or L, X22 is V, M, or T, and X23 is N or S.

SEQ ID NO: 16
XIIX2X3TQSPSSLSX4X5X6GX7RX8TIX9CX10ASQX11IRNX12LNW

YQQKPGQAPRLLIYYSSNLX13X14GVPX15RFSGSGSGTDFTLTISRLX

16X17EDX18AX19YYCQQSX20KLPX21TFGSGTKVEIK

In the sequence described above, X1 is D or E, X2 is L or E, X3 is M or L, X4 is A or V, X5 is S or T, X6 is L, P, or A, X7 is D or E, X8 is V or A, X9 is T or S, X10 is S or R, X11 is G or D, X12 is S or N, X13 is H or Q, X14 is S or T, X15 is S, D, or A, X16 is E or Q, X17 is P or A, X18 is F or V, X19 is T, A, or I, X20 is I or N, and X21 is F or L.

Table 1 shows the amino acid sequences of humanized VL variants X376 (SEQ ID NO: 1), X377 (SEQ ID NO: 2), X378 (SEQ ID NO: 3), X379 (SEQ ID NO: 4), X380 (SEQ ID NO: 5), X381 (SEQ ID NO: 6), and X394 (SEQ ID NO: 7). The schemes with Kabat numbering and sequential numbering correspond to light chain variable regions. Table 1 shows that CM03 VL comprises CDRL1 (SEQ ID NO: 33), CDRL2 (SEQ ID NO: 34) and CDRL3 (SEQ ID NO: 35), and that humanized VL variant X379 comprises CDRL1 (SEQ ID NO: 39), CDRL2 (SEQ ID NO: 40) and CDRL3 (SEQ ID NO: 41).

Table 2 show the amino acid sequences of and humanized VH variants X384 (SEQ ID NO: 8), X385 (SEQ ID NO: 9), X386 (SEQ ID NO: 10), X387 (SEQ ID NO: 11), X388 (SEQ ID NO: 12), X399 (SEQ ID NO: 13) and X420 (SEQ ID NO: 14). The table shows both sequential numbering and Kabat numbering schemes. The Kabat numbering scheme includes 82a, 82b, and 82c. Table 2 shows that CM03 VH comprises CDRH1 (SEQ ID NO: 30), CDRH2 (SEQ ID NO: 31) and CDRH3 (SEQ ID NO: 32), and that humanized VH variant X384 comprises CDRH1 (SEQ ID NO: 36), CDRH2 (SEQ ID NO: 37) and CDRH3 (SEQ ID NO: 38).

```
                                    Sequential Numbering
                     10        20        30        40        50
                     123456789012345678901234567890123456789012345678901234 56
                     <---------FR1---------><--CDR1---><-----FR2-----><CDR2->

CMD3 VL              DIQMTQSPSSLSASLGDRVTITCSASQGIRNSLNWYQQKPDGAVKLLIYYSSNLHS

X376                 DILMTQSPSSLSASPGDRVTISCRASQDIRNNLNWYQQKPGQAPRLLIYYSSNLHS

X377                 EIELTQSPSSLSVSLGDRVTISCSASQDIRNNLNWYQQKPGQAPRLLIYYSSNLQT

X378                 DIEMTQSPSSLSASAGERVTISCRASQGIRNSLNWYQQKPGQAPRLLIYYSSNLQT

X379                 DILLTQSPSSLSATPGERATITCRASQGIRNNLNWYQQKPGQAPRLLIYYSSNLQS

X380                 EIEMTQSPSSLSVSAGERATISCSASQDIRNSLNWYQQKPGQAPRLLIYYSSNLHT

X381                 EIELTQSPSSLSVSPGDRVTISCSASQGIRNSLNWYQQKPGQAPRLLIYYSSNLHT

X394                 DILMTQSPSSLSASPGDRVTISCRASQDIRNNLNWYQQKPGQAPRLLIYYSSNLQT
Kabat Numbering                           24        34                50   56
(same as sequential
numbering; no insertion)
```

```
                                    Sequential Numbering
                     60        70        80        90       100
                     7890123456789012345678901234567890123456789012345 67
                     <-------------FR3---------------><-CDR3--><---FR4--->

CMD3 VL              GVPSRFSGSGSGTDFSLTISNLRPEDIATYYCQQSIKLPFTFGSGTKLEIK

X376                 GVPDRFSGSGSGTDFTLTISRLEPEDFAAYYCQQSIKLPLTFGSGTKVEIK

X377                 GVPARFSGSGSGTDFTLTISRLEPEDVAAYYCQQSIKLPFTFGSGTKVEIK

X378                 GVPSRFSGSGSGTDFTLTISRLQAEDFATYYCQQSNKLPFTFGSGTKVEIK

X379                 GVPSRFSGSGSGTDFTLTISRLQPEDVAAYYCQQSIKLPFTFGSGTKVEIK

X380                 GVPARFSGSGSGTDFTLTISRLEPEDVAIYYCQQSNKLPLTFGSGTKVEIK

X381                 GVPARFSGSGSGTDFTLTISRLQAEDFATYYCQQSIKLPLTFGSGTKVEIK

X394                 GVPARGSGSGSGTDFTLTISRLEPEDFAAYYCQQSIKLPLTFGEGTKVEIK
Kabat Numbering                                        89        97
(same as sequential
numbering; no insertion)
```

```
                                    Sequential Numbering
                     10        20        30        40        50        60
                     123456789012345678901234567890123456789012345678901234567890123 45
                     <----------FR1----------><--CDR1--><----FR2-----><----CDR2------>

CMD3 VH              QVKLQKSGPGLVQPSQTLSITCTVSGFSLTTYGVHVWRQSPGKGLEWLGVIWGGGRTDYDAAFIS

X384                 EVQLVESGAGVKQPGGTLRLTCTASGFSLTTYGVHWVRQAPGKGLEWVGVIWGDGRTDYDAAFMS

X385                 EVQLVQSGGGVKQPGETLRLTCTASGFSLTTYGVHWVRQAPGKGLEWVGVIWGDGRTDYDAAFMS
```

| | |
|---|---|
| X386 | EVQLVESGAGVEQPGGTLRLTCTASGFSLTTYGVHWVRQAPGKGLEWMGVIWGDGRTDYDAAFMS |
| X387 | EVQLVESGAELVQPGGSLRLTCKASGFTLNTYGVHWVRQAPGKGLEWMGVIWGGGRTDYDASFMS |
| X388 | EVQLVQSGGGLKQPGETLRLSCTASGYSLTTYGVHWVRQAPGKGLEWMGVIWGDGRTDYDSSFMS |
| X399 | EVQLVQSGGGVKQPGETLRLTCTASGFSLSTYGVHWVRQAPGKGLEWVGVIWGDGRTDYDAAFMS |
| X420 | EVQLVESGGGVKQPGETLRLTCTASGFSLSTYGVHWVRQAPGKGLEWVGVIWGDGRTDYDAAFMS |
| Kabat Numbering | 26         35              50           65 |

Sequential Numbering

```
            70        80        90       100       110
        6789012345678901234567890123456789012345678901234567
        <------------FR3-------------><-CDR3--><--FR4--->
```

| | |
|---|---|
| CMD3 VH | RLSISKDNSKSQVFFKMNSLQANDTAIYYCVRNRHDWFDYWGQGTTVTVSS |
| X384 | RVTISKDTSKSTVYLQMNSLRAEDTAVYYCMRNRHDWFDYWGQGTTVTVSS |
| X385 | RVTISKDTSKSTAYLQMNSLRAEDTAVYYCMRNRHDWFDYWGQGTTVTVSS |
| X386 | RVTISRDTSKSTAYLQLNSLRAEDTAVYYCVRNRHDWFDYWGQGTTVTVSS |
| X387 | RVTISKDNSKNTAYLQLNSLRAEDTAVYYCTRSRHDWFDYWGQGTTVTVSS |
| X388 | RVTISKDTSKSTAYLQLMSLRAEDTAVYYCTRNRHDWFDYWGQGTTVTVSS |
| X399 | RVTISKDTSKSTVYLQMNSLRAEDTAVYYCMRNRHDWFDYWGQGTTVTVSS |
| X420 | RVTISKDTSKSTVYLQMNSLRAEDTAVYYCMRNRHDWFDYWGQGTTVTVSS |
| Kabat Numbering | abc3456789012345678901234567890123 |
| | 82       90       100       110 |
| | 95      102 |

The antibody may further comprise the amino acid sequence of SEQ ID NO: 17 or a fragment or a variant thereof. In a certain embodiment, the antibody comprises the amino acid sequence of SEQ ID NO: 17. In a certain embodiment, the antibody comprises the amino acid sequence of SEQ ID NO: 17 except for a signal sequence (those skilled in the art will readily understand that in a certain embodiment, the signal sequence of the antibody is cleaved off from the antibody). In a certain embodiment, the antibody comprises a variable region in the amino acid sequence of SEQ ID NO: 17. In a certain embodiment, the antibody includes an antibody (or a fragment thereof) having at least approximately 80%, at least approximately 85%, at least approximately 90%, at least approximately 95%, or at least approximately 98% identity to the amino acid sequence of SEQ ID NO: 17. In a certain embodiment, the antibody includes a fragment of the amino acid sequence of SEQ ID NO: 17, having a length of at least approximately 10 amino acids, at least approximately 25 amino acids, at least approximately 50 amino acids, at least approximately 75 amino acids, or at least approximately 100 amino acids. In a certain embodiment, the antibody binds to human CD26.

Heavy chain
(SEQ ID NO: 17)
MEWSWVFLFFLSVTTGVHSEVQLVESGAGVKQPGGTLRLTCTASGFSLTT

YGVHWVRQAPGKGLEWVGVIWGDGRTDYDAAFMSRVTISKDTSKSTVYLQ

MNSLRAEDTAVYYCMRNRHDWFDYWGQGTTVTVSSASTKGPSVFPLAPSS

KSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAP

-continued

ELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEAL

HNHYTQKSLSLSPGK

The antibody further comprises the amino acid sequence of SEQ ID NO: 18 or a fragment or a variant thereof. In a certain embodiment, the antibody comprises the amino acid sequence of SEQ ID NO: 18. In a certain embodiment, the antibody comprises the amino acid sequence of SEQ ID NO: 18 except for a signal sequence (those skilled in the art will readily understand that in a certain embodiment, the signal sequence of the antibody is cleaved off from the antibody). In a certain embodiment, the antibody comprises a variable region in the amino acid sequence of SEQ ID NO: 18. In a certain embodiment, the antibody includes an antibody (or a fragment thereof) having at least approximately 80%, at least approximately 85%, at least approximately 90%, at least approximately 95%, or at least approximately 98% identity to the amino acid sequence of SEQ ID NO: 18. In a certain embodiment, the antibody includes a fragment of the amino acid sequence of SEQ ID NO: 18, having a length of at least approximately 10 amino acids, at least approximately 25 amino acids, at least approximately 50 amino acids, at least approximately 75 amino acids, or at least approximately 100 amino acids. In a certain embodiment, the antibody further comprises the amino acid sequence of SEQ ID NO: 18 or a fragment or a variant thereof. In a certain embodiment, the antibody binds to human CD26. In a certain embodiment, the antibody is, for example, an antibody comprising at least one heavy chain (e.g., two heavy chains each) comprising the amino acid sequence of SEQ ID NO: 17 except for a signal sequence, and at least one light chain (e.g., two light chains each) comprising the amino acid sequence of SEQ ID NO: 18 except for a signal sequence.

Light chain
(SEQ ID NO: 18)
MSVPTQVLGLLLLWLTDARCDILLTQSPSSLSATPGERATITCRASQGIR

NNLNWYQQKPGQAPRLLIYYSSNLQSGVPSRFSGSGSGTDFTLTISRLQP

EDVAAYYCQQSIKLPFTFGSGTKVEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC

The humanized anti-CD26 antibody "YS110" described herein means an antibody whose heavy chain constant region consists of an amino acid sequence described in SEQ ID NO: 17, and light chain constant region consists of an amino acid sequence described in SEQ ID NO: 18. Upon binding to CD26 on a malignant tumor cell membrane, YS110 has been reported to be taken up into the cell and further transferred into the nucleus (Yamada K et al., Plos One, 2013 Apr. 29; 8 (4): e62304). More specifically, YS110 is considered to be taken up into the cytoplasm by caveolin-dependent endocytosis and transported into the nucleus by early endocytic vesicles. Accordingly, in one aspect, the antitumor effect (e.g., therapeutic effect on mesothelioma) of a YS110-triptolide conjugate may be based on such action of YS110. Specifically, the anti-CD26 antibody of the present invention may be an antibody that is, upon binding to CD26 on a malignant tumor cell membrane, taken up into the cell and further transferred into the nucleus. Whether or not the antibody is, upon binding to CD26 on a malignant tumor cell membrane, taken up into the cell and further transferred into the nucleus can be determined by contacting a labeled antibody with cells, then detecting a position of the antibody based on the label under a microscope or the like, and determining the positional relationship between the position and intracellular organization.

In another aspect, the antibody binds to one or more peptides selected from the group consisting of YSLRWISDHEYLY (SEQ ID NO: 19; peptide 6), LEYNYVKQWRHSY (SEQ ID NO: 20; peptide 35), TWSPVGHKLAYVW (SEQ ID NO: 21; peptide 55), LWWSPNGTFLAYA (SEQ ID NO: 22; peptide 84), RISLQWLRRIQNY (SEQ ID NO: 23; peptide 132), YVKQWRHSYTASY (SEQ ID NO: 24; peptide 37), EEEVFSAYSALWW (SEQ ID NO: 25; peptide 79), DYSISPDGQFILL (SEQ ID NO: 26; peptide 29), SISPDGQFILLEY (SEQ ID NO: 27; peptide 30), and IYVKIEPNLPSYR (SEQ ID NO: 28; peptide 63). In a certain embodiment, the antibody specifically binds to one or more of the peptides described above. These peptides are regions of human CD26. In a certain embodiment, the antibody specifically binds to one or more peptides selected from the group consisting of YSLRWISDHEYLY (SEQ ID NO: 19; peptide 6), LEYNYVKQWRHSY (SEQ ID NO: 20; peptide 35), TWSPVGHKLAYVW (SEQ ID NO: 21; peptide 55), LWWSPNGTFLAYA (SEQ ID NO: 22; peptide 84), RISLQWLRRIQNY (SEQ ID NO: 23; peptide 132), YVKQWRHSYTASY (SEQ ID NO: 24; peptide 37), EEEVFSAYSALWW (SEQ ID NO: 25; peptide 79), DYSISPDGQFILL (SEQ ID NO: 26; peptide 29), SISPDGQFILLEY (SEQ ID NO: 27; peptide 30), and IYVKIEPNLPSYR (SEQ ID NO: 28; peptide 63) as compared with one or more peptides corresponding to other regions of human CD26.

In a certain embodiment, the antibody binds to each of the following peptides: YSLRWISDHEYLY (SEQ ID NO: 19; peptide 6); LEYNYVKQWRHSY (SEQ ID NO: 20; peptide 35); TWSPVGHKLAYVW (SEQ ID NO: 21; peptide 55); LWWSPNGTFLAYA (SEQ ID NO: 22; peptide 84); and RISLQWLRRIQNY (SEQ ID NO: 23; peptide 132). In a certain alternative embodiment, the antibody binds to each of the following peptides: YSLRWISDHEYLY (SEQ ID NO: 19; peptide 6); TWSPVGHKLAYVW (SEQ ID NO: 21; peptide 55); RISLQWLRRIQNY (SEQ ID NO: 23; peptide 132); YVKQWRHSYTASY (SEQ ID NO: 24; peptide 37); and EEEVFSAYSALWW (SEQ ID NO: 25; peptide 79). In a certain embodiment, the antibody binds to each of the following peptides: DYSISPDGQFILL (SEQ ID NO: 26; peptide 29); SISPDGQFILLEY (SEQ ID NO: 27; peptide 30); and TWSPVGHKLAYVW (SEQ ID NO: 21; peptide 55). In a certain alternative embodiment, the antibody binds to each of the following peptides: DYSISPDGQFILL (SEQ ID NO: 26; peptide 29); SISPDGQFILLEY (SEQ ID NO: 27; peptide 30); TWSPVGHKLAYVW (SEQ ID NO: 21; peptide 55); and IYVKIEPNLPSYR (SEQ ID NO: 28; peptide 63).

Whether two antibodies bind to the same epitope by recognizing identical or sterically overlapping epitopes can be determined by competitive assay. Usually, an antigen is immobilized on a multiwell plate, and the blocking performance of an unlabeled antibody against the binding of a labeled antibody is measured. A general label for such competitive assay is a radiolabel or an enzyme label. The epitope to which the antibody binds can be determined by an epitope mapping technique known to those skilled in the art.

In a certain embodiment, the antibody comprises one or more constant regions. In a certain embodiment, the antibody comprises a human constant region. In a certain embodiment, the constant region is a heavy chain constant region. In an alternative embodiment, the constant region is a light chain constant region. In a certain embodiment, the antibody comprises a constant region having at least approximately 80%, at least approximately 85%, at least approximately 90%, at least approximately 95%, at least approximately 98%, or 100% identity to a human constant region. In a certain embodiment, the antibody comprises a Fc region. In a certain embodiment, the antibody comprises a human Fc region. In a certain embodiment, the antibody comprises a Fc region having at least approximately 80%, at least approximately 85%, at least approximately 90%, at least approximately 95%, at least approximately 98%, or 100% identity to a human Fc region.

In a certain embodiment, the antibody is an IgG antibody. In a certain embodiment, the antibody is an IgG1 antibody. In an alternative embodiment, the antibody is an IgG2 antibody. In a certain embodiment, the antibody is a human IgG antibody.

The antibody may be an antibody in monomeric, dimeric, and multimeric forms. For example, a bispecific antibody or a monoclonal antibody having binding specificity for at least two different antigens can be prepared using the antibody disclosed herein (see e.g., Suresh et al., Methods in Enzymology, 1986, 121, 210). Heretofore, the recombinant production of the bispecific antibody has been based on the coexpression of two immunoglobulin heavy chain-light chain pairs comprising two heavy chains differing in specificity (Millstein, Cuello, Nature, 1983, 305, 537-539).

According to one approach for preparing the bispecific antibody, antibody variable regions (antigen binding sites of the antibody) having the desired binding specificity are fused with immunoglobulin constant regions. Preferably, the fusion sites involve an immunoglobulin heavy chain constant region including at least moieties of a hinge and CH2 and CH3 regions. At least one fusion site preferably has the first heavy chain constant region (CH1) containing a site essential for the binding of a light chain. DNAs encoding the immunoglobulin heavy chain fusions and, if desired, DNA encoding an immunoglobulin light chain are inserted to separate expression vectors, with which an appropriate host organism is then cotransfected. In an embodiment in which unequal ratios of the three antibody chains used in the construction provide the optimum yield, it is possible to adjust the mutual proportions of these three antibody chains with high flexibility. If the expression of at least two antibody chains at equal ratios results in high yields or if the ratios are not particularly important, the coding sequences for two or all three antibody chains may be inserted to one expression vector.

One example of the approach includes a bispecific antibody constituted by a hybrid immunoglobulin heavy chain having first binding specificity in one of the arms, and a hybrid heavy chain-light chain pair (having second binding specificity) in the other arm. This asymmetric structure (having an immunoglobulin light chain only in one half-antibody moiety of the bispecific antibody molecule) facilitates separating the desired bispecific compound from undesired immunoglobulin chain combinations. This approach is described in International Publication No. WO94/04690 published on Mar. 3, 1994.

A heteroconjugate antibody comprising two covalently attached antibodies is also included in the scope of the antibody. Such an antibody is used for targeting cells of the immune system to unnecessary cells (U.S. Pat. No. 4,676,980) or for treating HIV infection (International Publication Nos. WO91/00360 and WO92/200373, and European Patent No. 03089). The heteroconjugate antibody may be prepared using any convenient cross-linking method. Appropriate cross-linking agents and cross-linking techniques are well known in the art and are described in U.S. Pat. No. 4,676,980.

In a particular embodiment, the antibody is an antibody fragment. In a certain embodiment, the antibody is selected from the group consisting of, for example, Fab, Fab', Fab'-SH, Fv, scFv, and F(ab')2. In a certain embodiment, the antibody is Fab. Various techniques have been developed for antibody fragment production. These fragments can be obtained via the protein digestion of a complete antibody (see e.g., Morimoto et al., 1992, J. Biochem. Biophys. Methods 24: 107-117; and Brennan et al., 1985, Science 229: 81), or can also be produced directly from recombinant host cells. For example, Fab'-SH fragments can be recovered directly from E. coli and chemically bound to form a F(ab')2 fragment (Carter et al., 1992, Bio/Technology 10: 163-167). In an alternative embodiment, F(ab')2 is formed using leucine zipper GCN4 which promotes the assembly of F(ab')2 molecules. According to an alternative approach, the Fv, Fab, or F(ab')2 fragment is isolated directly from recombinant host cell culture.

In a certain embodiment, the antibody is a single-chain variable fragment (scFv) thereof, a variant, a fusion protein containing an antibody moiety, a humanized antibody, a chimeric antibody, a diabody, a linear antibody, a single-chain antibody, or any other immunoglobulin molecule having a modified configuration.

The single-chain variable fragment is prepared by linking light chain and/or heavy chain variable regions using a short linker peptide (Bird et al., (1988) Science 242: 423-426). The linker peptide is, for example, (GGGGS)3 (SEQ ID NO: 29) which cross-links approximately 3.5 nm between the carboxy terminus of one of the variable regions and the amino terminus of the other variable region. Linkers having other sequences are also designed and used (Bird et al., (1988)). The linker can then be modified for additional functions such as immobilization of a drug or immobilization on a solid carrier. The single-chain variant can be produced by any recombination technique or synthesis technique. In the scFv production by a synthesis technique, an automatic synthesizer can be used. In the scFv production by a recombination technique, an appropriate plasmid containing a polynucleotide encoding scFv can be transferred to appropriate host cells either eukaryotic (e.g., yeast cells, plant cells, insect cells or mammalian cells) or prokaryotic (E. coli). The polynucleotide encoding the scFv of interest can be prepared by a routine operation such as polynucleotide ligation. The resulting scFv can be isolated using a standard protein purification technique known in the art.

Other forms of single-chain antibodies, such as a diabody, are also encompassed in the antibody. The diabody is a bivalent bispecific antibody whose VH and VL domains are expressed on a single antibody chain but forced to pair with complementary domains of another chain using a linker too short to pair these VH and VL domains on the same chain, thereby creating two antigen binding sites (see e.g., Holliger, P. et al., (1993) Proc. Natl. Acad. Sci. USA 90: 6444-6448; and Poljak, R. J. et al., (1994) Structure 2: 1121-1123).

The antibody encompasses a modified form of the antibody described herein. Examples of such a modified form include functionally equivalent antibodies without markedly affecting the properties of the antibody, and variants having potentiated or attenuated activity. The antibody modification is a routine operation in the art and needs not be described in detail herein. Examples of the modified antibody include antibodies involving the conservative substitution of amino acid residues, the deletion or addition of one or more amino acids without markedly deteriorating functional activity, or use of chemical analogs.

Insertion or addition to an amino acid sequence includes amino- and/or carboxyl-terminal fusion ranging in length from 1 residue to an antibody containing 100 or more residues, and the intrasequence insertion of single or multiple amino acid residues. Examples of terminal insertion variants include an antibody having a N-terminal methionyl residue or an antibody fused with an epitope tag. Other insertion variants of the antibody molecule include an antibody N- or C-terminally fused with an enzyme or an antibody increasing the serum half-life of the antibody.

The substitution variant has a different residue inserted in place of at least one amino acid residue removed from the antibody sequence. CDRs are included in sites that get the most out of substitution mutagenesis, though FR alterations are also contemplated. The conservative substitution is shown in Table 3 under the heading of "conservative substitution". Such substitution that changes biological activity is designated as "exemplary substitution" in Table 3, or more substantial change, as further described below about amino acid classes, may be introduced and products may be screened.

TABLE 3

Amino acid substitution

| Original residue | Conservative substitution | Exemplary substitution |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modification in the biological properties of the antibody is achieved by selecting a substitution that significantly changes the effect of the modification on the maintenance of (a) the structure of the antibody backbone at a substitution region, for example, a sheet or helical conformation, (b) the charge or hydrophobicity of the molecule at the target site, or (c) the bulk of the side chain. Naturally occurring residues are classified into the following groups based on general side chain properties:
(1) hydrophobic: norleucine, Met, Ala, Val, Leu, and Ile;
(2) neural hydrophilic: Cys, Ser, and Thr;
(3) acidic: Asp and Glu;
(4) basic: Asn, Gln, His, Lys, and Arg;
(5) residues influencing chain orientation: Gly and Pro; and
(6) aromatic: Trp, Tyr, and Phe.

Non-conservative substitution is accomplished by exchanging a member of one of these classes for a member of another class. More conservative substitution includes exchange of one member of a certain class for another member of this class.

Any cysteine residue that is not involved in the maintenance of the appropriate conformation of the antibody can be substituted, usually by serine, to thereby improve the oxidative stability of the molecule and prevent abnormal cross-linking. Particularly, when the antibody is an antibody fragment such as a Fv fragment, a cysteine bond can be added to the antibody to thereby improve the stability of the antibody.

The amino acid modification ranges from change or modification in one or more amino acids to the complete redesign of a region such as a variable region. Change in a variable region can change binding affinity and/or specificity. In a certain embodiment, 1 to 5 or less amino acids are conservatively substituted within a CDR domain. In an alternative embodiment, 1 to 3 or less amino acids are conservatively substituted within a CDR3 domain. In a further alternative embodiment, the CDR domain is CDRH3 and/or CDRL3.

The modified antibody also includes glycosylated and nonglycosylated antibodies and antibodies having other posttranslational modifications, for example, glycosylation with different sugars, acetylation, and phosphorylation.

Antibodies are glycosylated at conserved positions in their constant regions (Jefferis and Lund, 1997, Chem. Immunol. 65: 111-128; and Wright and Morrison, 1997, TibTECH 15: 26-32). The oligosaccharide side chains of immunoglobulins influence protein functions (Boyd et al., 1996, Mol. Immunol. 32: 1311-1318; and Wittwe and Howard, 1990, Biochem. 29: 4175-4180) and the intramolecular mutual action between moieties of a glycoprotein, which may influence the conformation and presented three-dimensional surface structure of the glycoprotein (Hefferis and Lund, supra; and Wyss and Wagner, 1996, Current Opin. Biotech. 7: 409-416). Given glycoproteins may target certain molecules based on specific recognition structures via oligosaccharides. Antibody glycosylation has also been reported to influence antibody-dependent cellular cytotoxicity (ADCC). Particularly, CHO cells expressing β(1,4)-N-acetylglucosaminyltransferase III (GnTIII), a glycosyltransferase catalyzing the formation of bisecting GlcNAc, under the control of tetracycline have been reported to exhibit improved ADCC activity (Umana et al., 1999, Nature Biotech. 17:176-180).

The antibody glycosylation is usually either N-linked or O-linked. The N-linked glycosylation means the attachment of a carbohydrate moiety to the side chain of an asparagine residue. Tripeptide sequences asparagine-X-serine, asparagine-X-threonine, and asparagine-X-cysteine (wherein X is any amino acid other than proline) are recognition sequences for enzymatically adding a carbohydrate moiety to the asparagine side chain. Thus, any of these tripeptide sequences present in the antibody creates a potential glycosylation site. The O-linked glycosylation means the attachment of one of the carbohydrates N-acetylgalactosamine, galactose, and xylose to a hydroxyamino acid, most generally serine or threonine, though 5-hydroxyproline or 5-hydroxylysine may be used.

The addition of the glycosylation site to the antibody is conveniently achieved by altering the amino acid sequence such that the antibody contains one or more of the tripeptide sequences described above (for a N-linked glycosylation site). The alteration may also be accomplished by the addition of or substitution by one or more serine or threonine residues to the sequence of the original antibody (for an O-linked glycosylation site).

The glycosylation pattern of the antibody may also be altered without altering the fundamental nucleotide sequence. The glycosylation depends largely on host cells used for expressing the antibody. Since the type of cells used for expression of a recombinant glycoprotein, for example, an antibody, is rarely natural cells because of a possible treatment method, the diverse glycosylation patterns of the antibody can be predicted (see, e.g. Hse et al., 1997, J. Biol. Chem. 272: 9062-9070).

In addition to the selection of host cells, factors that influence glycosylation during the recombinant production of the antibody include the mode of growth, medium formulation, culture density, oxygenation, pH, purification schemes, etc. Various methods have been proposed to alter the glycosylation pattern achieved in particular host organisms and involve introducing or overexpressing particular enzymes involved in oligosaccharide production (U.S. Pat. Nos. 5,047,335, 5,510,261, and 5,278,299). The glycosylation or a particular type of glycosylation can be removed from the glycoprotein using an enzyme, for example, endoglycosidase H (EndoH). Recombinant host cells can be genetically altered to be defective in the processing of a particular type of polysaccharide. These and similar techniques are well known in the art.

Other methods for the modification include use of a coupling technique known in the art. Examples of such a technique include, but are not limited to, enzymatic approaches, oxidative substitution and chelation. For example, a label for immunoassay can be added to the antibody using the modification. The modified antibody is prepared using procedures established in the art and can be screened using standard assay known in the art. Some methods therefor are described below and in Examples.

Other modified antibodies include antibodies modified as described in International Publication No. WO99/58572 published on Nov. 18, 1999. These antibodies comprise a binding domain directed to the target molecule as well as an effector domain having an amino acid sequence substantially homologous to the whole or a portion of human immunoglobulin heavy chain constant domains. These antibodies have the ability to bind to the target molecule without causing marked complement-dependent lysis or cell-mediated destruction of the target. In a certain embodiment, the effector domain can specifically bind to FcRn and/or FcγRIIb. These are usually based on chimeric domains derived from two or more human immunoglobulin heavy chain CH2 domains. The antibodies thus modified are particularly suitable for use in chronic antibody therapy and avoid inflammatory and other harmful reactions to conventional antibody therapy.

The antibody includes an affinity-matured form. The affinity-matured antibody can be produced by, for example, a method known in the art (Marks et al., 1992, Bio/Technology, 10: 779-783; Barbas et al., 1994, Proc Nat. Acad. Sci, USA 91: 3809-3813; Schier et al., 1995, Gene, 169: 147-155; Yelton et al., 1995, J. Immunol., 155: 1994-2004; Jackson et al., 1995, J. Immunol., 154 (7): 3310-9; Hawkins et al., 1992, J. Mol. Biol., 226:889-896; and International Publication No. WO2004/058184). An affinity-matured antibody candidate can be screened for or selected based on improved and/or altered binding affinity by any method known in the art including any selection method known in the art including a screening method using BIAcore surface plasmon resonance analysis, phage display, yeast display, and ribosome display.

The monoclonal antibody may be prepared by a hybridoma method as described in Kohler and Milstein, 1975, Nature 256: 495. In the hybridoma method, mice, hamsters, or other appropriate host animals are usually immunized with an immunizing agent to thereby induce lymphocytes producing or capable of producing antibodies specifically binding to the immunizing agent. Alternatively, lymphocytes may be immunized in vitro.

The monoclonal antibody (and other antibodies) may also be prepared by a recombinant DNA method as described in U.S. Pat. No. 4,816,567. DNA encoding the monoclonal antibody is isolated and sequenced by conventional methods such as use of an oligonucleotide probe that can specifically bind to a gene encoding the heavy chain or the light chain of the monoclonal antibody. The DNA thus isolated is inserted to an expression vector, with which host cells such as E. coli cells, simian COS cells, Chinese hamster ovary (CHO) cells, or myeloma cells which do not produce immunoglobulin proteins without the transfer of the expression vector are then transfected to thereby achieve monoclonal antibody synthesis in the recombinant host cells.

In a certain embodiment, the antibody is expressed in any organism including, but is not limited to, bacteria, yeasts, plants, insects, and mammals, or cells derived from any organism. The particular type of the cells includes, but is not limited to, Drosophila melanogaster cells, cells of Saccharomyces cerevisiae and other yeasts, E. coli cells, Bacillus subtilis cells, SF9 cells, HEK-293 cells, cells of Neurospora, BHK cells, CHO cells, COS cells, Hela cells, fibroblasts, schwannoma cell lines, immortalized mammalian myeloid and lymphoid cell lines, Jurkat cells, mast cells and other endocrine and exocrine cells, and neuronal cells.

Various protein expression systems, vectors, and cell media useful in antibody production are known to those skilled in the art. See, for example, International Publication Nos. WO03/054172, WO04/009823, and WO03/064630, all of which are incorporated herein by reference in their entirety. In a certain embodiment, a glutamine synthetase (GS) expression system is used in the expression of the antibody.

Preferably, the antibody thus expressed is purified or isolated according to a method known to those skilled in the art. Examples of the purification method include electrophoretic, molecular biological, immunological and chromatographic approaches. Examples of such approaches include ion-exchange, hydrophobic affinity, reverse-phase HPLC chromatography, and isoelectric focusing. The necessary degree of purification may vary depending on the purpose of the antibody. Depending on embodiments, purification is unnecessary.

The DNA may be modified, for example, by covalently linking the whole or a portion of the coding sequence of a non-immunoglobulin antibody to the immunoglobulin coding sequence. In this way, a "chimeric" or "hybrid" antibody having the binding specificity of the monoclonal antibody disclosed herein is prepared. Usually, such a non-immunoglobulin antibody is substituted by the constant domains of the antibody of the present invention or substituted by the variable domains of one antigen binding site of the antibody of the present invention to thereby create a chimeric bivalent antibody comprising one antigen binding site having specificity for one surface epitope on CD26 and another antigen binding site having specificity for a different antigen or CD26 epitope.

The antibody also encompasses a humanized antibody. Therapeutic antibodies often induce adverse reactions, partly because of inducing immune response to the administered antibodies. This may result in reduction in drug efficacy, decrease in the number of cells having the target antigen, and undesirable inflammatory reaction. To circumvent these problems, a recombinant anti-CD26 humanized antibody may be prepared. The general principles of antibody humanization involve maintaining the basic sequence of the antigen binding moiety of the antibody, while swapping at least a portion of the nonhuman remainder of the antibody with a human antibody sequence. Four general conventional steps for monoclonal antibody humanization include, but are not limited to: (1) determining nucleotide sequences encoding the light chain and heavy chain variable domains of a starting antibody, and their putative amino acid sequences, (2) designing a humanized antibody, i.e., determining antibody framework regions or residues and/or CDR residues to be used in the humanization process, (3) an actual humanization methodology/technique, and (4) transfection and expression of the humanized antibody. The constant regions of the antibody for use in clinical trials and treatment in humans can also be rendered more analogous to human constant regions by a recombination technique to avoid immune response. See, for example, U.S. Pat. Nos. 5,997,867 and 5,866,692.

A Fcγ moiety in a recombinant humanized antibody can be modified to thereby avoid mutual action with a Fcγ receptor and the complement immune system. Such an antibody preparation technique is described in International Publication No. WO99/58572.

Many "humanized" antibody molecules comprising a nonhuman immunoglobulin-derived antigen binding site have been reported. Examples thereof include rodent V regions and their associated complementarity determining regions (CDRs) fused with human constant domains. See, for example, Winter et al., Nature 349: 293-299 (1991); Lobuglio et al., Proc. Nat. Acad. Sci. USA 86: 4220-4224 (1989); Shaw et al., J Immunol. 138: 4534-4538 (1987); and Brown et al., Cancer Res. 47: 3577-3583 (1987). Other references describe rodent CDRs grafted into human supporting framework regions (FRs) before fusion with appropriate human antibody constant domains. See, for example, Riechmann et al., Nature 332: 323-327 (1988); Verhoeyen et al., Science 239: 1534-1536 (1988); and Jones et al., Nature 321: 522-525 (1986). Another reference describes rodent CDRs supported by recombinantly veneered rodent framework regions. See, for example, European Patent Publication No. 519,596. These types of "humanized" molecules are designed to minimize unnecessary immunological response to rodent anti-human antibody molecules, which limits the therapeutic application period and efficacy of the moieties in human recipients. Other antibody humanization methods that may be used are disclosed in Daugherty et al., Nucl. Acids Res., 19: 2471-2476 (1991) and U.S. Pat. Nos. 6,180,377, 6,054,297, 5,997,867, 5,866,692, 6,210,671, and 6,350,861, and International Publication No. WO01/27160.

Further exemplary methods for the antibody humanization are described in International Publication No. WO02/084277 and U.S. Patent Publication No. 2004/0,133,357, both of which are incorporated herein by reference in their entirety.

Still alternatively, a fully human antibody can be obtained using commercially available mice engineered to express specific human immunoglobulin proteins. Transgenic animals designed to produce more desirable (e.g., fully human antibody) or more robust immune response may also be used in humanized or human antibody preparation. Examples of such a technique include Xenomouse™ from Abgenix Inc. (Fremont, Calif.) and HuMAb-Mouse® and TC Mouse™ from Medarex, Inc. (Princeton, N.J.).

Alternatively, the antibody may be recombinantly prepared by a phage display technique. See, for example, U.S. Pat. Nos. 5,565,332, 5,580,717, 5,733,743 and 6,265,150; and Winter et al., Annu. Rev. Immunol. 12: 433-455 (1994). Alternatively, the phage display technique (McCafferty et al., Nature 348: 552-553 (1990)) can be used for producing human antibodies and human antibody fragments in vitro from immunoglobulin variable (V) domain gene repertoires from unimmunized donors. According to this technique, antibody V domain genes are cloned in frame into major or minor coat protein genes of filamentous bacteriophages, such as M13 or fd, and displayed as functional antibody fragments on the surface of the phage particles. Because the filamentous particles contain a single-stranded DNA copy of the phage genome, antibody selection based on functional properties also leads to the selection of genes encoding antibodies exhibiting these properties. Thus, the phages mimic some of the properties of B cells. The phage display can be carried out in various formats. For review, see, for example, Johnson, Kevin S. and Chiswell, David J., Current Opinion in Structural Biology 3, 564-571 (1993). A plurality of sources of V gene segments can be used in the phage display.

Clackson et al. (Nature 352: 624-628 (1991)) isolated diverse arrays of anti-oxazolone antibodies from a small random combinatorial library of V genes derived from the spleens of immunized mice. V gene repertoires from unimmunized human donors can be constructed, and antibodies against diverse arrays of antigens (including self-antigens) can be isolated by essentially following a technique described by Mark et al., J. Mol. Biol. 222: 581-597 (1991) or Griffith et al., EMBO J. 12: 725-734 (1993). In natural immune response, antibody genes accumulate mutations at a high rate (somatic hypermutation). Some of introduced changes will confer high affinity, and B cells displaying a high-affinity surface immunoglobulin are preferentially replicated and differentiated during subsequent antigen challenge. This natural process can be mimicked by a technique known as "chain shuffling" (Marks, et al., Bio/Technol. 10: 779-783 (1992)). In this method, the affinity of "primary" human antibodies obtained by phage display can be improved by sequentially replacing the heavy chain and light chain V region genes with repertoires of natural variants (repertoires) of V domain genes obtained from unimmunized donors. This technique allows production of antibodies and antibody fragments having affinity in the range of pM to nM. A strategy to prepare very large phage antibody repertoires (also known as "mother-of-all libraries") is described by Waterhouse et al., Nucl. Acids Res. 21: 2265-2266 (1993).

A human antibody having affinity and specificity equivalent to those of a starting rodent antibody may be induced from the rodent antibody by gene shuffling. According to this method, also referred to as "epitope imprinting", the heavy chain or light chain V domain genes of rodent antibodies obtained by the phage display technique are replaced with human V domain gene repertoires to create rodent-human chimeras. Selection based on an antigen brings about the isolation of human variable regions that can reconstruct a functional antigen binding site. Specifically, the epitope governs (imprints) partner selection. When the method is repeated to replace residual rodent V domains, the human antibody is obtained (see International Publication No. WO9306213 published on Apr. 1, 1993). Unlike the conventional humanization of rodent antibodies by CDR grafting, this technique provides completely human antibodies free from rodent-derived framework or CDR residues. Although the discussion described above relates to humanized antibodies, it is apparent that the general principles discussed are applicable to, for example, antibody customization for use in dogs, cats, primates, horses and cattle.

The chimeric or hybrid antibody may also be prepared in vitro by a known method of synthetic protein chemistry, including a method using a cross-linking agent. For example, immunotoxins can be constructed by using disulfide exchange reaction or forming a thioether bond. Examples of reagents suitable for this purpose include iminothiolate and methyl-4-mercaptobutyrimidate.

The single-chain Fv fragment may also be produced as described in Iliades et al., 1997, FEBS Letters, 409: 437-

441. The coupling of such single-chain fragments using various linkers is described in Kortt et al., 1997, Protein Engineering, 10: 423-433. Various techniques regarding the recombinant production and recombinant manipulation of antibodies are well known in the art.

The antibody may be conjugated with a water-soluble polymer moiety. The antibody may be conjugated with polyethylene glycol (PEG), monomethoxy-PEG, an ethylene glycol/propylene glycol copolymer, carboxymethylcellulose, dextran, polyvinyl alcohol, or the like. The antibody may be modified at random positions on the molecule or at predetermined positions on the molecule and may contain one, two, or three or more attached moieties. The polymer may have any molecular weight and may be branched or nonbranched. In a certain embodiment, the moiety is attached to the polypeptide via a linker. In a certain embodiment, the attached moiety increases the circulation half-life of the antibody in vivo in animals. Methods for attaching polymers such as PEG to antibodies are well known in the art. In a certain embodiment, the antibody is a PEGylated antibody such as a PEGylated antibody. The conjugate may be further conjugated with an additional different drug such as a chemotherapeutic, a radionuclide, an immunotherapeutic, a cytokine, a chemokine, a contrast medium, a toxin, a biological agent, an enzyme inhibitor, or an antibody.

2. Antibody-Drug Conjugate

In a certain embodiment, the present invention relates to a conjugate comprising the antibody and triptolide conjugated with each other. The triptolide is (3bS,4aS,5aS,6R,6aR,7aS,7bS,8aS,8bS)-6-hydroxy-6a-isopropyl-8b-methyl-3b,4,4a,6,6a,7a,7b,8b,9,10-decahydrotrisoxireno[6,7:8a,9:4b,5]phenanthro[1,2-c]furan-1(3H)-one under IUPAC name and has a structure represented by the following formula:

[Formula 1]

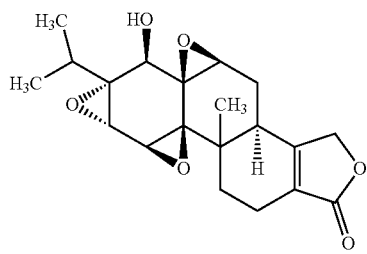

Accordingly, the antibody-triptolide conjugate of the present invention can be represented by the following formula:

[Formula 2]

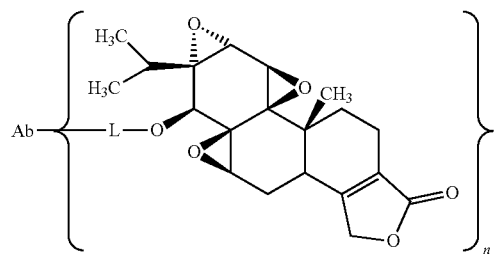

wherein Ab represents the antibody, L represents a linker, and n is a natural number which represents the number of the triptolide attached to the antibody.

The antibody and the triptolide are covalently attached via the linker L. To attach the antibody and the triptolide, a multivalent linker (e.g., a divalent linker) can be used as the linker L. Linkers that can attach drugs to an antibody are well known in the art. The linker may be degradable or may be nondegradable. The linker may or may not contain a sulfur atom. For example, the linker can be acid-degradable, photodegradable, peptidase-degradable, esterase-degradable, disulfide bond-reducing, or hydrophobic. The linker may have, for example, a maleimide group or a haloacetyl group as a basic skeleton.

Examples of the linker includes N-succinimidyl 3-(2-pyridyldithio)-propionate (SPDP), N-[γ-maleimidobutyryloxy]succinimide ester (GMBS), succinimidyl-4-(N-maleimidomethyl)cyclohexane-1-carboxylate (SMCC), N-(4-maleimidobutyryloxy) sulfosuccinimide, sodium salt (Sulfo-GMBS), N-[(4-maleimidomethyl)cyclohexylcarbonyloxy]sulfosuccinimide, sodium salt (Sulfo-SMCC), N-succinimidyl-4-(maleimidomethyl)cyclohexane-1-carboxy-(6-amidocaproate) (LC-SMCC), κ-maleimidoundeconic acid N-succinimidyl ester (KMUA), ε-maleimidocaproic acid N-succinimidyl ester (EMCS), m-maleimidobenzoyl-N-hydroxysuccinimide ester (MBS), N-(α-maleimidoacetoxy)-succinimide ester (AMSA), succinimidyl-6-(β-maleimidopropionamido)hexanoate (SMPH), N-succinimidyl-4-(p-maleimidophenyl)-butyrate (SMPB), N-(p-maleimidophenyl) isocyanate (PMIP), maleimide-based cross-linking agents containing PEG, N-succinimidyl iodoacetate (SIA), N-succinimidyl(4-iodoacetyl) aminobenzoate (SIAB), N-succinimidyl bromoacetate (SBA), and N-succinimidyl 3-(bromoacetamido) propionate (SBAP).

The starting material for triptolide can be a dimer having the following structure in order to enhance preservation stability, and this dimer itself can be used with reduction.

[Formula 3]

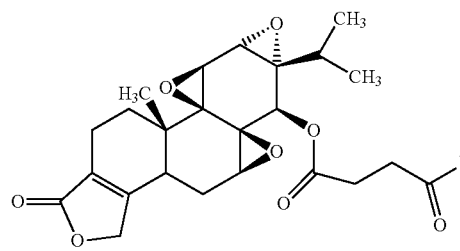

In this case, the dimer is reduced to give the following substance containing a 4-oxo-4-[(2-thiolethyl)amino]butanoic acid group bonded to each triptolide.

[Formula 4]

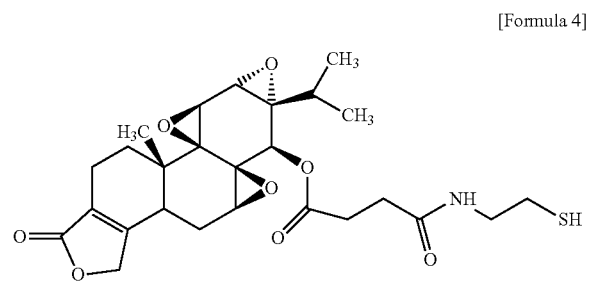

The 4-oxo-4-[(2-thiolethyl)amino]butanoic acid group bonded to the triptolide may be used as the linker L. Alternatively, the 4-oxo-4-[(2-thiolethyl)amino]butanoic acid group may be removed, and the linker mentioned above may be attached directly to the triptolide as the linker L. Alternatively, the linker L may be a group in which the divalent linker mentioned above is bonded to a 4-oxo-4-[(2-thiolethyl)amino]butanoic acid group. For example, when 4-oxo-4-[(2-thiolethyl)amino]butanoic acid and SMCC are used as the linker L, the antibody-triptolide conjugate of the present invention can be represented by the following formula:

attachment position of the triptolide to the antibody is not particularly limited as long as the position does not influence the specificity of the antibody. Preferably, the triptolide is attached to a constant region of the antibody.

The antibody-drug conjugate of the present invention can be manufactured by a method well known to those skilled in the art. For example, the antibody and the linker can be reacted first to bind each other, and then the linker can be attached to the drug (triptolide). Specifically, the antibody is reacted with the linker of 10 to 50 times the molar amount of the antibody dissolved in DMSO at room temperature for 30 minutes in PBS-EDTA (pH 7.5), and unreacted linkers are removed to obtain the antibody attached to the linker. A dimer of a triptolide derivative is dissolved in 100% ethanol and reduced for 2 hours. The linker-modified antibody and the triptolide can be reacted overnight at a ratio of 1:5.68 at room temperature in PBS-EDTA pH 7.5 to obtain an antibody-linker-triptolide attachment product.

3. Concomitant Drug

The present invention further relates to a concomitant drug of the antibody and an additional antitumor agent. Examples of the antitumor agent that may be used concomitantly with the antibody can include: alkylating drugs including nitrogen mustards such as cyclophosphamide, ifosfamide, melphalan, busulfan, and thiotepa, and nitroureas such as nimustine, ranimustine, dacarbazine, procarbazine, temozolomide, carmustine, streptozocin, and bendamustine; platinum compounds such as cisplatin, car-

[Formula 5]

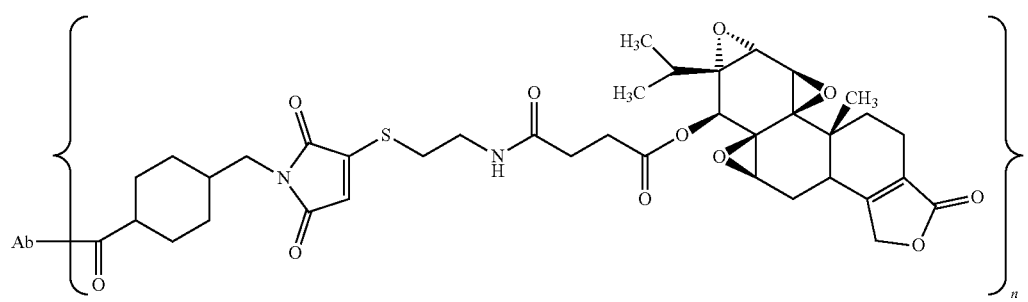

The number of the triptolide (represented by n in the formula described above) attached to one antibody molecule may be at least 1 and can be, for example, 2 or more, 2.5 or more, 3 or more, 3.5 or more, 4 or more, 4.5 or more, 5 or more, 5.5 or more, 6 or more, 6.489 or more, 6.5 or more, 7 or more, 7.5 or more, 8 or more, 8.5 or more, 9 or more, 9.5 or more, or 10 or more. Also, the number of the triptolide (represented by n in the formula described above) attached to one antibody molecule can be 3 or less, 3.5 or less, 4 or less, 4.5 or less, 5 or less, 5.5 or less, 6 or less, 6.5 or less, 7 or less, 7.5 or less, 8 or less, 8.5 or less, 9 or less, 9.5 or less, or 10 or less. Alternatively, the number of the triptolide attached to one antibody molecule can be 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, or 1, 2, 2.5, 3, 3.5, 4, 4.5, 5, 5.5, 6, 6.5, 6.489, 7, 7.5, 8, 8.5, 9, 9.5 or 10.

The attachment of the linker to the antibody is usually achieved by acylating a lysine residue of the antibody. The boplatin, oxaliplatin, and nedaplatin; antimetabolite drugs such as enocitabine, capecitabine, carmofur, cladribine, gemcitabine, cytarabine, cytarabine ocfosfate, tegafur, tegafur uracil, tegafur/gimeracil/oteracil potassium, doxifluridine, nelarabine, hydroxycarbamide, 5-fluorouracil (5-FU), fludarabine, pemetrexed, pentostatin, mercaptopurine, and methotrexate; plant alkaloids or microtubule inhibiting drugs such as irinotecan, etoposide, eribulin, sobuzoxane, docetaxel, nogitecan, paclitaxel, vinorelbine, vincristine, vindesine, and vinblastine; anticancer antibiotics such as actinomycin D, aclarubicin, amrubicin, idarubicin, epirubicin, zinostatin stimalamer, daunorubicin, doxorubicin, pirarubicin, bleomycin, peplomycin, mitomycin C, mitoxantrone, and liposomal doxorubicin; cancer vaccines such as sipuleucel-T; molecular targeting drugs such as ibritumomab tiuxetan, imatinib, everolimus, erlotinib, gefitinib, gemtuzumab ozogamicin, sunitinib, cetuximab, sorafenib, dasatinib, tamibarotene, trastuzumab, tretinoin, panitumumab, bevacizumab, bortezomib, lapatinib, and rituximab; hormone agents such as anastrozole, exemestane, estramustine, ethinylestradiol, chlormadinone, goserelin, tamoxifen, dexamethasone, toremifene, bicalutamide, flutamide, prednisolone, fosfestrol, mitotane, methyltestosterone, medroxyprogesterone, mepitiostane, leuprorelin, and letrozole; and biological response modifiers such as interferon α, interferon β, interferon γ, interleukin, ubenimex, dry BCG, and lentinan. Cisplatin, pemetrexed, or gemcitabine is preferred, and gemcitabine is more preferred.

The concomitant drug (pharmaceutical composition containing two or more drugs) of the present invention may contain all or a part of two or more types of drugs to be used concomitantly in one preparation, or may be provided as separate preparations containing each drug alone for concomitant use. Alternatively, the concomitant drug of the present invention may be provided as a kit for concomitant use including separate preparations containing each drug of all or a part of two or more types of drugs to be used concomitantly.

4. Application

The conjugate or the concomitant drug of the present invention is useful in various applications including, but are not limited to, a method for treatment or a method for lysing malignant cells. The present invention includes, for example, a pharmaceutical composition, a therapeutic drug for malignant mesothelioma, a malignant mesothelioma cell growth inhibitor, and a malignant mesothelioma cell lysing agent, which contain the conjugate or the concomitant drug of the present invention as an active ingredient. The present invention may also provide the conjugate or the concomitant drug of the present invention for use in a pharmaceutical composition, a therapeutic drug for malignant mesothelioma, a malignant mesothelioma cell growth inhibitor, or a malignant mesothelioma cell lysing agent. Alternatively, the present invention may provide a use of the conjugate of the present invention or a use of an anti-CD26 antibody and an antitumor agent in the manufacture of a pharmaceutical composition, a therapeutic drug for malignant mesothelioma, a malignant mesothelioma cell growth inhibitor, or a malignant mesothelioma cell lysing agent. In one aspect, the present invention includes a method for treating malignant mesothelioma, a method for inhibiting malignant mesothelioma cell growth, and a method for lysing malignant mesothelioma cells, comprising administering an effective amount of the conjugate or the concomitant drug of the present invention to a patient in need thereof. Accordingly, the present invention also provides a method for inhibiting CD26-expressing cell growth. The inhibition of CD26-expressing cell growth includes any observable inhibition, including partial growth inhibition and complete growth inhibition. In a certain embodiment, the cell growth is inhibited by at least approximately 10%, at least approximately 25%, at least approximately 50%, at least approximately 75%, at least approximately 90%, at least approximately 95%, at least approximately 98%, or approximately 100%. The method may be performed in vitro or in vivo. In a certain embodiment, the method comprises the step of contacting the cells with the conjugate or the concomitant drug described herein. In general, the cells are contacted with a sufficient amount of the conjugate or the concomitant drug for inhibiting the cell growth.

In a certain embodiment, the CD26-expressing cells are mammalian cells and are preferably human cells. In a certain embodiment, the CD26-expressing cells are cancer cells. In a certain embodiment, the CD26-expressing cells are cells of malignant mesothelioma, lung cancer, kidney cancer, liver cancer or other malignant tumors involving the expression of CD26. In a certain embodiment, the tumor cells are malignant or benign.

Methods for evaluating the inhibition of cell growth are known in the art. Examples thereof include MTT assay (see e.g., Aytac et al., (2003) British Journal of Cancer 88: 455-462; Ho et al., (2001) Clinical Cancer Research 7: 2031-2040; Hansen et al., (1989) J. Immunol. Methods, 119: 203-210; and Aytac et al., (2001) Cancer Res 61: 7204-7210).

The present invention further provides a method for treating a condition associated with CD26 expression in a subject. The method for treating a condition associated with CD26 expression in a subject comprises administering an effective amount of a composition comprising the conjugate or the concomitant drug described herein to the subject. The condition associated with CD26 expression may be associated with the abnormal expression of CD26. The condition associated with CD26 expression may be a condition associated with a change or abnormality in CD26 expression (in a certain embodiment, increase or decrease in CD26 expression level (as compared with a normal sample) and/or inappropriate expression, for example, expression in tissues and/or cells normally expressing no CD26, or deficiency in CD26 expression in tissues or cells normally expressing CD26). The condition associated with CD26 expression may be a condition associated with CD26 overexpression. The condition associated with CD26 expression may be mediated at least partially by CD26, may be a condition associated with CD26-expressing cells, or may be a condition with the abnormal growth of CD26-expressing cells. The CD26-expressing cells may be T cells or tumor cells. The tumor cells may be malignant or benign.

The condition associated with CD26 expression in the subject includes a proliferative disease, particularly, a cancer. The cancer is malignant mesothelioma, lung cancer, kidney cancer, liver cancer or any other malignant tumor involving the expression of CD26.

The method (including the treatment method) described herein may be accomplished by single direct injection at one time or multiple times to single or multiple sites. The administration may also be performed to a plurality of sites at almost the same time. The frequency of administration is determined and adjusted in the course of treatment and is based on the desired results to be achieved. In some cases, a sustained-release preparation of the conjugate, the concomitant drug, or the pharmaceutical composition of the present invention may be appropriate. Various preparations and apparatuses for achieving sustained release are well known in the art.

The subject for treatment or prevention includes mammals such as humans, cattle, horses, dogs, cats, pigs, and sheep and is preferably a human.

The conjugate or the concomitant drug is preferably administered as being contained in a carrier (preferably a pharmaceutically acceptable carrier) to a mammal. Appropriate carriers and their preparations are described in Remington's Pharmaceutical Sciences, 18th edition, A. Gennaro ed., Mack Publishing Co., Easton, Pa., 1990 and Remington, The Science and Practice of Pharmacy, 20th edition, Mack Publishing, 2000. Usually, an appropriate amount of a pharmaceutically acceptable salt is used in a preparation so that the preparation has isotonicity. Examples of the carrier include physiological saline, Ringer's solutions and dextrose solutions. The pH of these solutions is preferably approximately 5 to approximately 8, more preferably approximately 7 to approximately 7.5. Further examples of the carrier include sustained-release preparations such as semipermeable matrices of solid hydrophobic polymers containing the antibody. The matrices are in the form of shaped articles, for example, films, liposomes, or microparticles. It will be apparent to those skilled in the art that a certain carrier may be more preferred depending upon, for example, the administration route and concentration of the antibody to be administered.

The conjugate or the concomitant drug may be administered to a mammal by injection (e.g., systemic, intravenous, intraperitoneal, subcutaneous, intramuscular, or intraportal injection), or may be administered thereto by other methods (e.g., infusion) that secure delivery in an effective form to blood stream. The conjugate or the concomitant drug may be administered by an isolated perfusion method such as isolated tissue perfusion to exert a local therapeutic effect. Intravenous injection is preferred.

Effective doses and schedules for administering the conjugate or the concomitant drug of the present invention are empirically determined. Methods for such determination are included within technical common sense in the art. Those skilled in the art will understand that the dose of the conjugate or the concomitant drug to be administered varies depending on, for example, the mammal that will receive the conjugate or the concomitant drug, an administration route, the specific type of the antibody used, and other drugs to be administered to the mammal. The typical daily amount of the conjugate (used alone) or the concomitant drug administered may range from approximately 1 µg/kg body weight to 100 mg/kg body weight or more per day, though depending on the factors mentioned above. In general, any of the following amounts administered may be used: at least approximately 50 mg/kg body weight; at least approximately 10 mg/kg body weight; at least approximately 3 mg/kg body weight; at least approximately 1 mg/kg body weight; at least approximately 750 µg/kg body weight; at least approximately 500 µg/kg body weight; at least approximately 250 µg/kg body weight; at least approximately 100 µg/kg body weight; at least approximately 50 µg/kg body weight; at least approximately 10 µg/kg body weight; at least approximately 1 µg/kg body weight, or more.

The conjugate or the concomitant drug may be administered to the mammal by further concomitant use with effective amounts of one or more other therapeutic drugs. The conjugate or the concomitant drug may be administered sequentially or concurrently with the one or more other therapeutic agents. The amounts of the conjugate or the concomitant drug and the therapeutic drug depend on, for example, the types of the drugs used, a pathological condition to be treated, an administration schedule and an administration route and may generally be less than the amounts of the conjugate or the concomitant drug and the therapeutic drug used individually.

The physiological condition of the mammal thus given the conjugate or the concomitant drug can be monitored by various methods well known to those skilled in the art.

5. Method for Screening for Compound Exhibiting Synergistic Effect by Concomitant use with Anti-CD26 Antibody In a further alternative aspect, the present invention relates to a method for screening for a compound exhibiting a synergistic effect by concomitant use with an anti-CD26 antibody. The screening method of the present invention is based on CD26 that mutually acts and counters with CD9 (Okamoto et al., PLOS One (2014) 9 (1): e86671). When a chemotherapeutic candidate mutually acts with CD26, its effect is attenuated by CD9. Therefore, a candidate differing in growth inhibitory effect between a cell line coexpressing CD26 and CD9 and a cell line expressing CD26 but expressing no CD9 can be determined as a medication exhibiting a synergistic effect by concomitant use with an anti-CD26 antibody. Specifically, the screening method of the present invention is a method for screening for a compound exhibiting a synergistic antitumor effect by concomitant use with an anti-CD26 antibody, comprising the following steps:
(a) culturing a tumor cell line coexpressing CD26 and CD9, and a cell line expressing CD26 but expressing no CD9 in the presence of a test compound;
(b) measuring the respective numbers of cells of the tumor cell lines thus cultured;
(c) calculating a growth inhibitory effect of the test compound on the tumor cell line coexpressing CD26 and CD9, and a growth inhibitory effect of the test compound on the cell line expressing CD26 but expressing no CD9; and
(d) comparing the growth inhibitory effect of the test compound on the tumor cell line coexpressing CD26 and CD9, and the growth inhibitory effect of the test compound on the cell line expressing CD26 but expressing no CD9, and selecting the test compound as a compound likely to exhibit a synergistic antitumor effect by concomitant use with an anti-CD26 antibody when the growth inhibitory effect on the cell line expressing CD26 but expressing no CD9 is better.

In this method, a mesothelioma cell line MESO1 or H2452 can be used as the tumor cell line coexpressing CD26 and CD9. JMN or H226 can be used as the cell line expressing CD26 but expressing no CD9.

The step of measuring the respective numbers of cells of the tumor cell lines can adopt every known method as long as the method provides measurement values reflecting the numbers of cells. For example, other numerical values serving as an index for the number of cells, such as turbidity or a measurement value of MTT assay may be used instead of the number of cells.

The growth inhibitory effect on each tumor cell line may be calculated as the number of cells with that of a control defined as 100, or a numerical value serving as an index for drug efficacy, such as IC50 may be calculated. The degree of the growth inhibitory effect can be confirmed as excellent growth inhibitory effect when the number of cells whose growth has been suppressed is large.

Hereinafter, the present invention will be described in more detail with reference to Examples. However, the present invention is not limited by these Examples. All literatures cited herein are incorporated herein by reference in their entirety.

(Example 1) Antibody-Drug Conjugation (1) Starting Material

A humanized anti-CD26 antibody YS110 was designed based on an anti-CD26 mouse antibody 14D10 and expressed according to the already reported approach (see International Publication No. WO2007/014169); and Inamoto T et al., Clin Cancer Res (2007) 13: 4191-200). Triptolide having the following structure (molecular formula: C20H24O6; MW=360.4) was purchased from Shaanxi Taiji Technology (Shanxi Sheng, China).

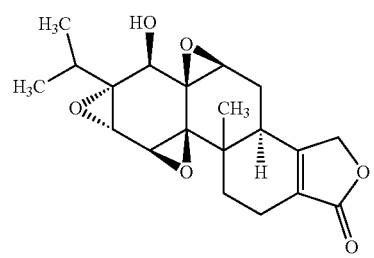

[Formula 6]

(2) Conjugation Protocol

A SH group was introduced to the triptolide by Chem-Genesis Inc. (Tokyo, Japan). The obtained triptolide derivative was designated as TR1. TR1 was provided as a dimer of such triptolide derivatives bound via a S—S bond for enhanced scientific stability and had the following structure.

[Formula 7]

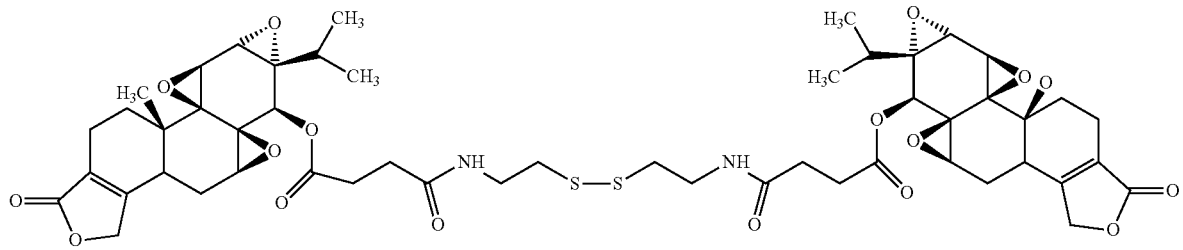

A hetero-divalent linker SPDP (N-succinimidyl 3-(2-pyridyldithio)-propionate) (catalog No. 21857, Thermo Fisher Scientific Inc., Waltham, Mass.), GMBS (N-[γ-maleimidobutyryloxy]succinimide ester) (catalog No. 22309, Thermo Fisher Scientific Inc., Waltham, Mass.), or SMCC (succinimidyl 4-[N-maleimidomethyl] cyclohexane-1-carboxylate) (catalog No. 22360, Thermo Fisher Scientific Inc., Waltham, Mass.) was dissolved in DMSO immediately before use. YS110 was modified through reaction with the hetero-divalent linker SPDP (15 times the molar quantity of the antibody), GMBS (30 times the molar quantity of the antibody), or SMCC (20 times the molar quantity of the antibody) at room temperature for 30 minutes in PBS-EDTA (pH 7.5). Unreacted linkers were removed using HiTrap Desalting column (catalog No. 21857, GE Healthcare Inc., Buckinghamshire, UK). The triptolide derivative TR1 S—S dimer was dissolved in 100% ethanol and reduced with immobilized TCEP Reducing Gel (catalog No. 77712, Thermo Fisher Scientific Inc., Waltham, Mass.) for 2 hours. The SH group concentration of the reduced TR1-SH was measured by DTNB ((5,5-dithio-bis-(2-nitrobenzoic acid)) assay. The linker-modified YS110 and the TR1-SH were reacted overnight at a ratio of 1:5.68 at room temperature in PBS-EDTA pH 7.5. Unreacted TR1-SH was removed using PD-10 column (catalog No. 17085101, GE Healthcare Inc., Buckinghamshire, UK). This reaction is summarized below.

[Formula 8]

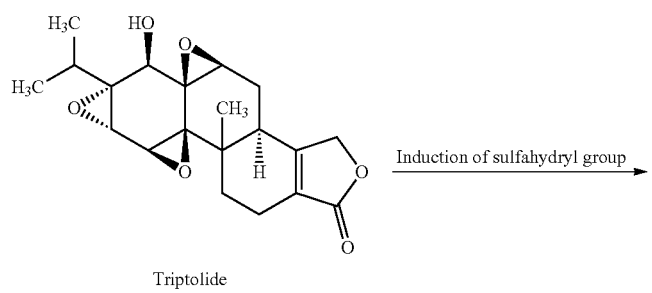

Triptolide

Induction of sulfahydryl group

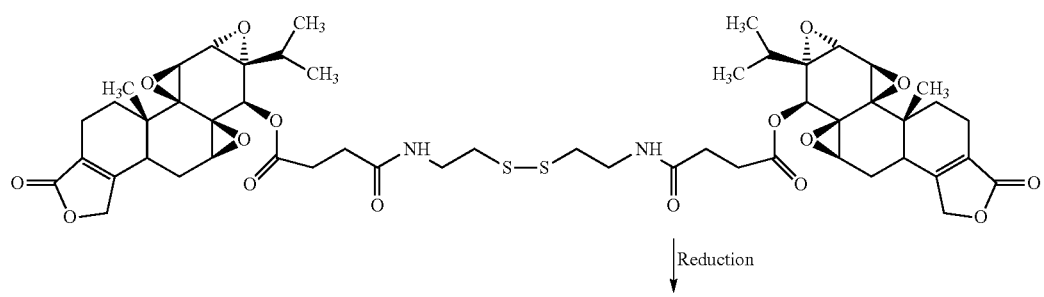

Reduction

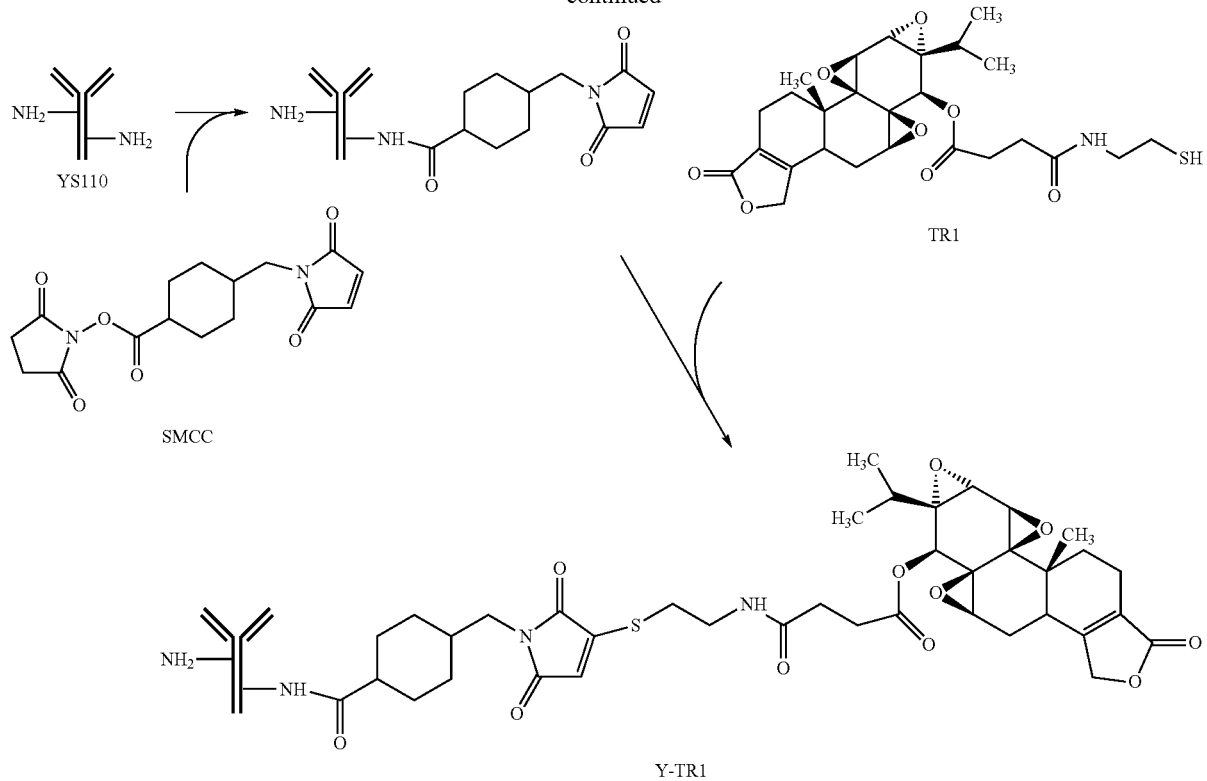

The obtained product was filter-sterilized through Millex-GV Filter Unit 0.22 um (Cat no. SLGV 013SL, EMD Millipore, Billerica, Mass.). The final concentration was measured using BCA protein assay reagent kit (catalog No. 23225, Thermo Fisher Scientific Inc., Waltham, Mass.). Residual unconjugated TR1-SH in the product was measured by DTNB assay.

(3) Results

YS110 and TR1 were conjugated using a hetero-divalent linker (SPDP, GMBS, or SMCC) according to the method described above. The final product concentration measured using BCA protein assay reagent kit (Thermo Fisher Scientific Inc., Waltham, Mass.) was approximately 1 mg/ml. Residual unconjugated TR1-SH in the product was measured by DTNB assay, but was hardly detectable (data not shown).

(Example 2) Cell Culture

A CD26-negative malignant mesothelioma cell line MSTO-211H (MSTO) (American Type Cell Culture Collection, Manassas, Va.) was transfected with CD26 gene, which was designated as MSTO clone 12 (Aoe K et al., Clin Cancer Res. (2012) 18: 1447-56). A CD26-negative T-cell leukemia cell line Jurkat (American Type Cell Culture Collection, Manassas, Va.) was transfected with CD26 gene, which was designated as Jurkat CD26(+) (Tanaka T et al., Proc Natl Acad Sci USA (1993) 90: 4586-90). A CD26-positive cell line JMN established from malignant mesothelioma was kindly provided by professor Chikao Morimoto, the Institute of Medical Science, the University of Tokyo. All the cell lines were cultured in RPMI medium (catalog No. 11875-093, Life Technologies Corp., Carlsbad, Calif.) containing 10% heat-inactivated fetal bovine serum (FBS, Life Technologies Corp., Carlsbad, Calif.), ABPC (100 µg/ml), and streptomycin (100 µg/ml) at 37° C. under 5% $CO_2$ environment.

(Example 3) Mass Spectrometry

The drug/antibody ratio of Y-TR1 was analyzed by matrix-assisted laser desorption/ionization mass spectrometry (MALDI-TOFmass) using Autoflex III (Bruker Corporation, Billerica, Mass.) after ultrafiltration.

Figure 1B:
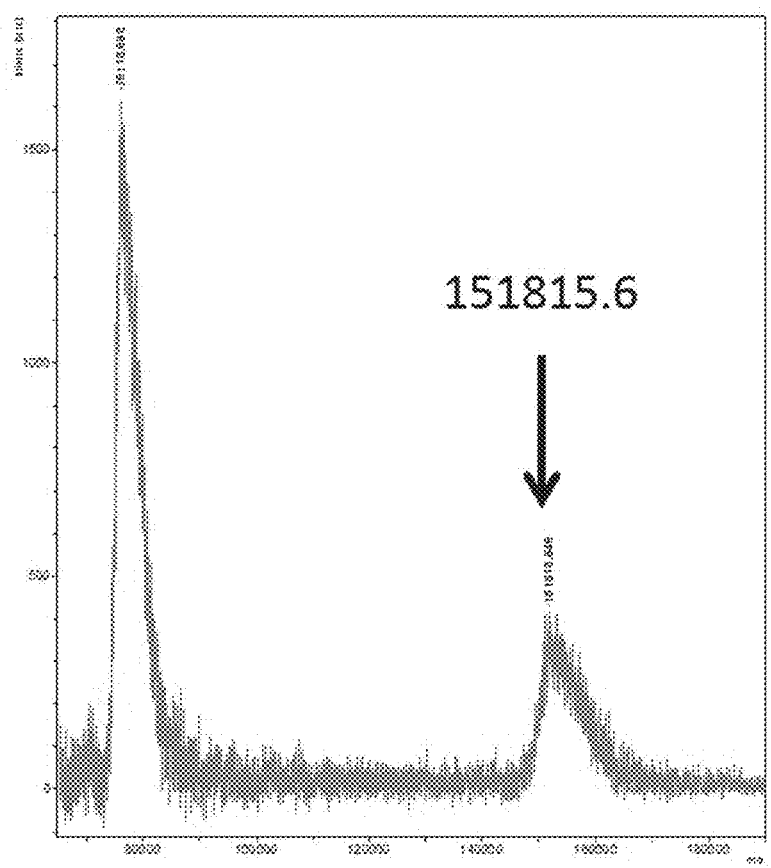
FIG. 1B shows Y-TR1 (SMCC) (measured value: 151815.6).

The intact masses of unconjugated YS110 and Y-TR1 (SMCC) analyzed by MALDI-TOFmass were 147012.7 and 151815.6, respectively (FIG. 1). The estimated molecular amount of antibody-conjugated TR1 with the SMCC group was 739.6. Based on this molecular amount, the average number of TR1-SMCC groups attached to one molecule of YS110 can be calculated according to the expression {(151815.6-147012.7)/739.6} and was consequently 6.489. This means that 6.489 molecules of TR-1 were attached to one molecule of YS110 on average.

(Example 4) Binding Assay

To examine the binding of Y-TR1 to CD26-positive malignant mesothelioma cells, cultured MSTO-wt cells (CD26-negative) and MSTO clone 12 cells (CD26-positive) were recovered. $1 \times 10^6$ cells of each cell line were cultured with 1 µg/ml, 10 µg/ml, or 100 µg/ml Y-TR1 at 4° C. for 30 minutes. The cells were washed three times and cultured with FITC-conjugated rabbit anti-human IgG (catalog No. 6140-02, Southern Biotech, Birmingham, Ala.) at a dilution ratio of 1:100 at 4° C. for 30 minutes. The cells were washed three times, followed by FACS analysis using Epics XL-MCL (Beckman Coulter, Inc., Brea, Calif.).

Figure 2:
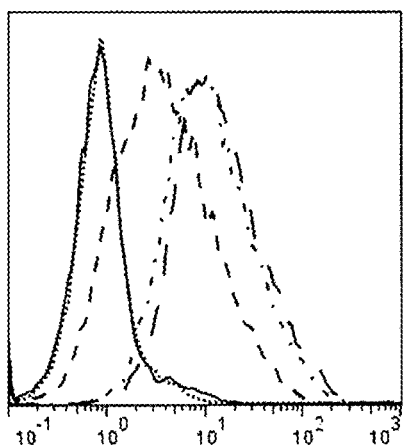
FIG. 2 is a graph of the binding of Y-TR1 to a malignant mesothelioma cell line MSTO clone 12 (CD26-positive). Primary antibody: Y-TR1, secondary antibody: FITC-conjugated rabbit anti-human IgG. At 10 µg/ml or higher, Y-TR1 exhibited intact binding to the CD26-positive cells. The ordinate indicates fluorescence intensity, and the abscissa indicates the number of cells.

The intact binding of Y-TR1 to the CD26-positive malignant mesothelioma cell line MSTO clone 12 was confirmed by flow cytometry analysis (FIG. 2).

(Example 5) Cytotoxicity Assay

The cytotoxicity of triptolide, YS110 and Y-TR1 to malignant mesothelioma and T-cell leukemia cell lines was measured using colorimetric cell proliferation kit WST-1 (catalog No. 11644807001, Roche Applied Science, Rotkreuz, Switzerland) based on the colorimetric detection of a formazan dye. In summary, $5 \times 10^3$ MSTO-wt, MSTO clone 12, JMN, Jurkat CD26(−), or Jurkat CD26(+) cells were cultured with triptolide (0 to 100 nM), TR1 (0 to 100 nM), YS110 (0 to 100 μg/ml), or Y-TR1 (0 to 100 ug/ml) in RPMI medium containing 10% heat-inactivated fetal bovine serum, ABPC (100 μg/ml) and streptomycin (100 μg/ml) in a 96-well plate at 37° C. for 48 hours under 5% $CO_2$ environment. WST-1 assay was conducted according to the manual provided by the manufacturer. The background absorbance of each sample at 630 nm was subtracted from the measurement value thereof at 450 nm. The experiment was conducted in triplicate, and typical results are shown.

As shown in FIG. 3, the triptolide exhibited a dose-dependent toxic effect on the malignant mesothelioma cell lines MSTO-wt, MSTO clone 12, and JMN, and the T-cell leukemia cell lines Jurkat and Jurkat CD26(+) after the treatment for 48 hours. The IC50 value of the triptolide for these cell lines is shown in Table 4.

Figure 4A:
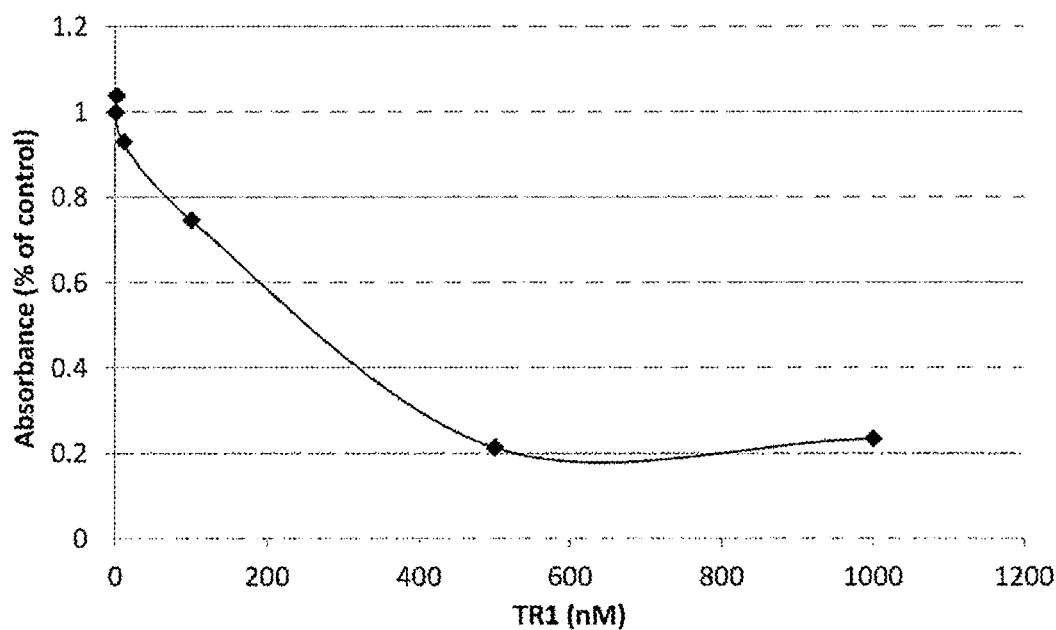
FIG. 4 is a graph of in vitro cytotoxicity of TR1 to a malignant mesothelioma cell line. The ordinate indicates fluorescence intensity (%) vs. control, and the abscissa indicates the concentration (nM) of TR1.
Figure 4B:
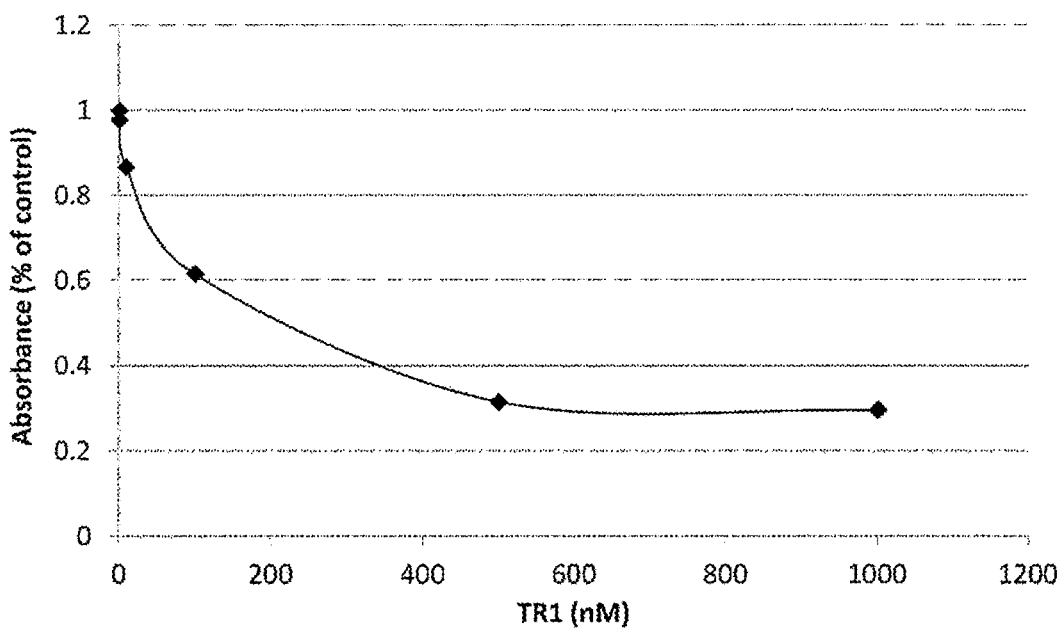
Figure 5A:
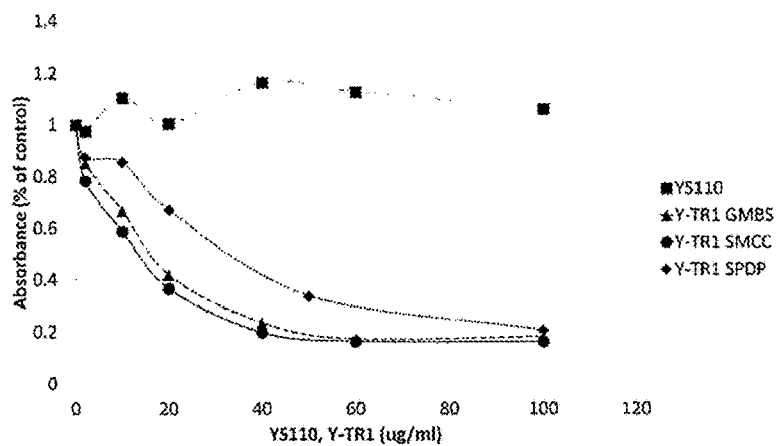
FIG. 5A shows the cytotoxicity of Y-TR1 to a CD26-positive malignant mesothelioma cell line MSTO clone 12, comparing various linkers used. Y-TR1 using SMCC exhibited the highest cytotoxicity.
Figure 5B:
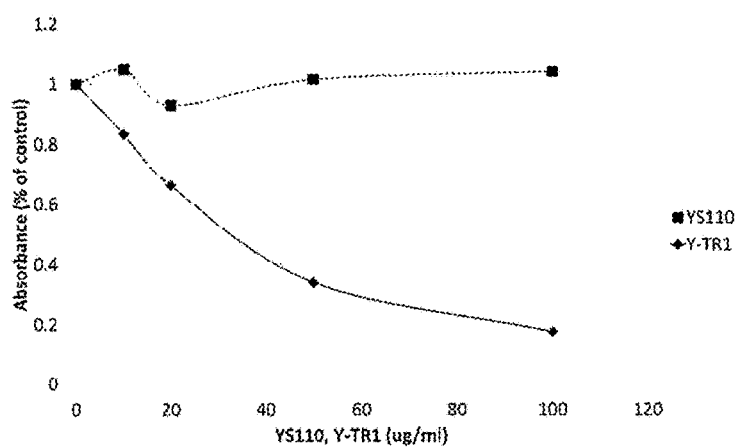
FIG. 5B shows the cytotoxicity of TR1 towards CD26-positive malignant mesothelioma cell line JMN as compared with unconjugated YS110.
Figure 5C:
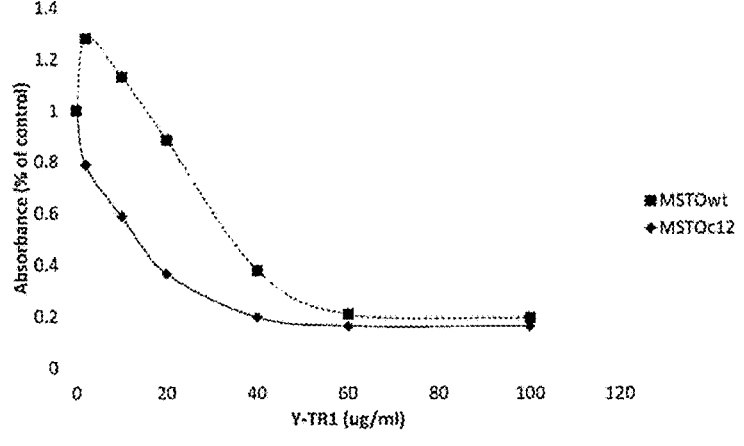
FIG. 5C is a graph showing the in vitro cytotoxicity of Y-TR1 towards the CD26-positive malignant mesothelioma cells MSTO clone 12, which is compared with that towards the CD26-negative wild-type MSTO (wt) cell line. Y-TR1 exhibited higher cytotoxicity against the CD26-positive malignant mesothelioma cells MSTO clone 12 than against the CD26-negative wild-type MSTO (wt) cell line.
Figure 5D:
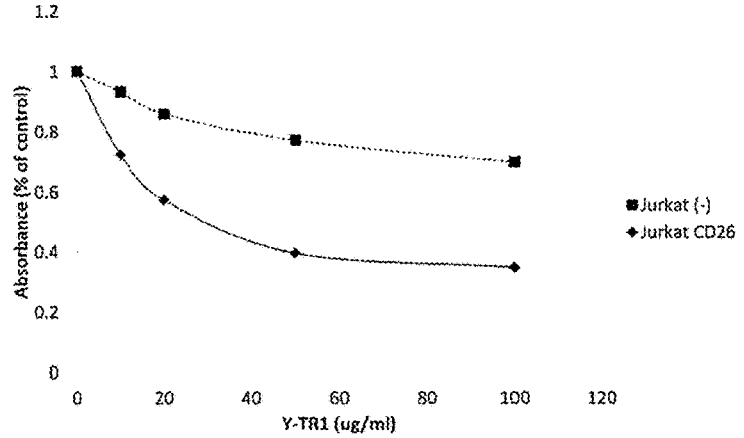
FIG. 5 is a graph of in vitro cytotoxicity of Y-TR1 to malignant mesothelioma and T-cell leukemia cell lines.

The triptolide derivative TR1 that was designed for attachment to the linker was tested for its cytotoxicity and IC50 value in the same way as above. The results are shown in FIG. 4 and Table 4. TR1 was reduced from the SS dimer using immobilized TR-1 TCEP Reducing Gel (Thermo Fisher Scientific Inc., Waltham, Mass.) before assay.

Figure 6:
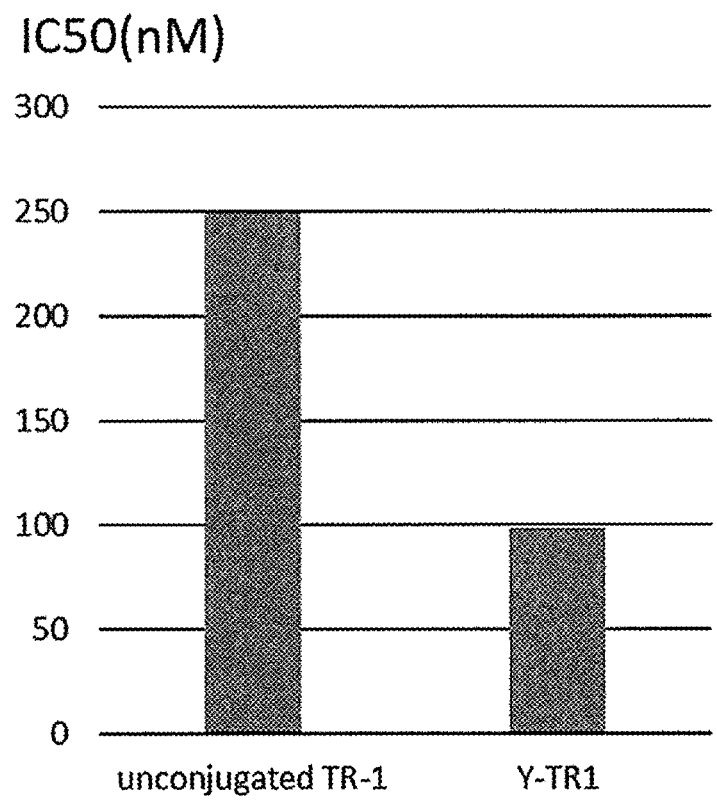
FIG. 6 is a graph comparing IC50 values of unconjugated TR1 and Y-TR1 in molar concentrations.

Y-TR1 exhibited dose-dependent cytotoxicity to the CD26-positive malignant mesothelioma and leukemia cell lines (FIG. 5). The cytotoxicity of Y-TR1 to the CD26-positive malignant mesothelioma cell line MSTO clone 12 was compared among 3 types of linkers (SPDP, GMBS and SMCC) (FIG. 5A). As a result of this comparison among 3 types of hetero-divalent linkers, the IC50 value of Y-TR1 for MSTO clone 12 was 38 μg/ml, 18 μg/ml and 15 μg/ml for use of SPDP, GMBS and SMCC, respectively (Table 5). In this experiment, the conjugate Y-TR1 via SMCC exhibited the best cytotoxicity. Therefore, Y-TR1 (SMCC) was used in subsequent experiments. The cytotoxicity of Y-TR1 to the CD26-positive or CD26-negative malignant mesothelioma and leukemia cell lines was compared with that of unconjugated YS110 (FIGS. 5A and 5B). The IC50 value of Y-TR1 (SMCC) for various cell lines is shown in Table 4. Y-TR1, compared with YS110, exhibited remarkably higher cytotoxicity to the CD26-positive cells (MSTO clone 12, JMN, and Jurkat CD26(+)). The CD26-positive cell lines (MSTO clone 12 and Jurkat CD26(+)), compared with the corresponding CD26-negative cells (MSTO wt and Jurkat CD26(−)), were more highly sensitive to Y-TR1 cytotoxicity (FIGS. 5C and 5D). Free TR-1 (corresponding to Y-TR1) for the MSTO clone 12 cell line was calculated from the IC50 values of Y-TR1 (approximately 15 μg/ml=99 nM) and unconjugated TR-1 (250 nM). As a result, one molecule of Y-TR1 corresponded to 2.5 molecules of TR1 (FIG. 6). From this, it was confirmed that the cytotoxic action on a mesothelioma cell line per triptolide molecule was remarkably enhanced by its conjugation with the anti-CD26 antibody YS110. These results indicated that malignant mesothelioma can be treated with a smaller amount administered.

TABLE 4

| Cell line | Origin | CD26 | IC50 of Triptolide (nM) | IC50 of TR1 (nM) | IC50 of Y-TR1 (μg/ml) |
|---|---|---|---|---|---|
| MSTO wt | Mesothelioma | (−) | 10 | 250 | 35 |
| MSTO clone12 | Mesothelioma | (+) | 10 | 250 | 15 |
| JMN | Mesothelioma | (+) | 15 | ND | 30 |
| Jurkat (−) | Leukemia | (−) | >100 | ND | >100 |
| Jurkat CD26 (+) | Leukemia | (+) | 6 | ND | 30 |

TABLE 5

| conjugate | IC50 (ug/ml) |
|---|---|
| Y-TR1 SPDP | 35 |
| Y-TR1 GMBS | 18 |
| Y-TR1 SMCC | 15 |

(Example 6) In Vivo Effect Assay and Toxicity Study

NOD/SCID (NOD/LtSz-scid) mice were maintained in a microisolator cage within a specific pathogen-free (SPF) facility and allowed to freely take sterilized diet and sterilized water. The animal experiment protocol was conducted with the approval of the Animal Care and Use Committee.

$1 \times 10^7$ cultured JMN cells were subcutaneously administered to 6- to 8-week-old female NOD/SCID mice. A total of 30 animals were randomly divided into 3 types of treatment groups: a control group, a YS110 administration group, and a Y-TR1 administration group. 4 mg/kg/dose of YS110 or Y-TR1 was intraperitoneally administered to the YS110 and Y-TR1 groups three times a week (a total of 9 times) from the day of tumor inoculation. The same amount of PBS was administered to the control group. When a tumor became evidently visible, the tumor was excised, and its size was measured with a vernier caliper. The estimated tumor volume was determined by calculation according to the expression: $\pi/6 \times L \times W \times W$ (Tomayko M M et al., Cancer Chemother Pharmacol. (1989) 24: 148-54). The statistical difference among the average tumor volumes of these groups were determined by Fisher's protected least-square differences (PLSD) multiple comparison test. Statistical analysis was conducted using SPSS software (IBM, Armonk, N.Y.).

Figure 7:
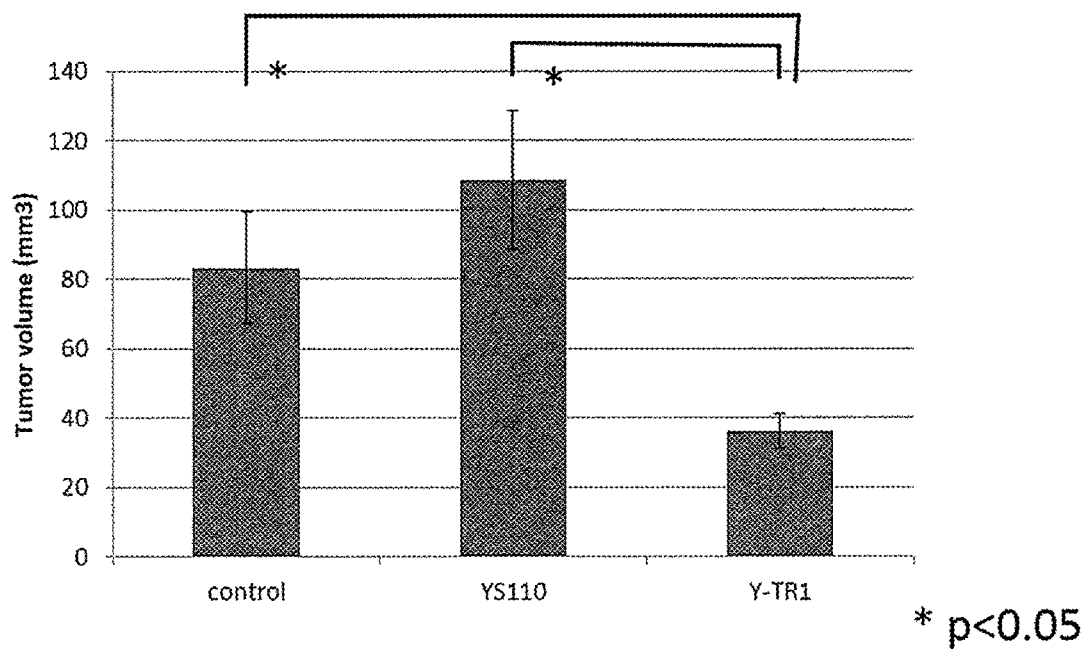
FIG. 7 is a graph of the in vivo antitumor activity of Y-TR1 measured by using NOD/SCID xenograft mouse models which have been grafted a CD26-positive malignant mesothelioma cell line JMN. Y-TR1 was administered intraperitoneally at 4 mg/kg/dose three times a week. Y-TR1 was administered 9 times in total from the day of administration of $1 \times 10^7$ JMN cells subcutaneously (day0). An average estimated tumor volume at day 55 was compared among 3 groups (control group, YS110 administration group, and Y-TR1 administration group) by Fisher's protected least-square differences (PLSD) multiple comparison test. The average tumor volume of the Y-TR1 administration group was remarkably lower than that of the control group and the YS110 administration group (p<0.05). The ordinate indicates the estimated average tumor volume ($mm^3$), and the abscissa indicates the group.

FIG. 7 shows results about the in vivo efficacy of Y-TR1 compared with unconjugated YS110 on the NOD/SCID mouse xenograft models prepared using the CD26-positive malignant mesothelioma cell line JMN. The average tumor volume of day 55 estimated according to the ellipsoid volume formula ($\pi/6 \times L \times W \times H$) (Tomayko M M et al., Cancer Chemother Pharmacol. (1989) 24: 148-54) was compared among 3 groups (control, YS110, and Y-TR1) by Fisher's protected least-square differences (PLSD) multiple comparison test. The average tumor volume of the Y-TR1 administration group (intraperitoneally given 36 mg/kg in total of Y-TR1) was remarkably lower as compared with the control group and the YS110 administration group ($p<0.05$). The complete suppression of tumor growth was megascopically confirmed in two of the nine mice in the Y-TR1 administration group at the completion of the experiment (day 55). FIG. 7 shows one typical example of similar experiment results obtained twice. The average body weight of the mice at the completion of the experiment did not remarkably differ among the groups.

(Example 7) Confirmation of CD26 Expression in Mesothelioma Cell Line

CD26 expression in a mesothelioma cell line was confirmed by FACS measurement. Among CD26-positive mesothelioma cell lines, ACC-MESO1 and JMN were used as sarcomatoid mesothelioma cell lines, and NCI-H2452 and NCI-H226 were used as epithelioid mesothelioma cell lines. The ACC-MESO1, JMN, NCI-H2452, and NCI-H226 cells were stained with anti-CD26 monoclonal antibody-FITC, followed by FACS analysis.

Figure 8:
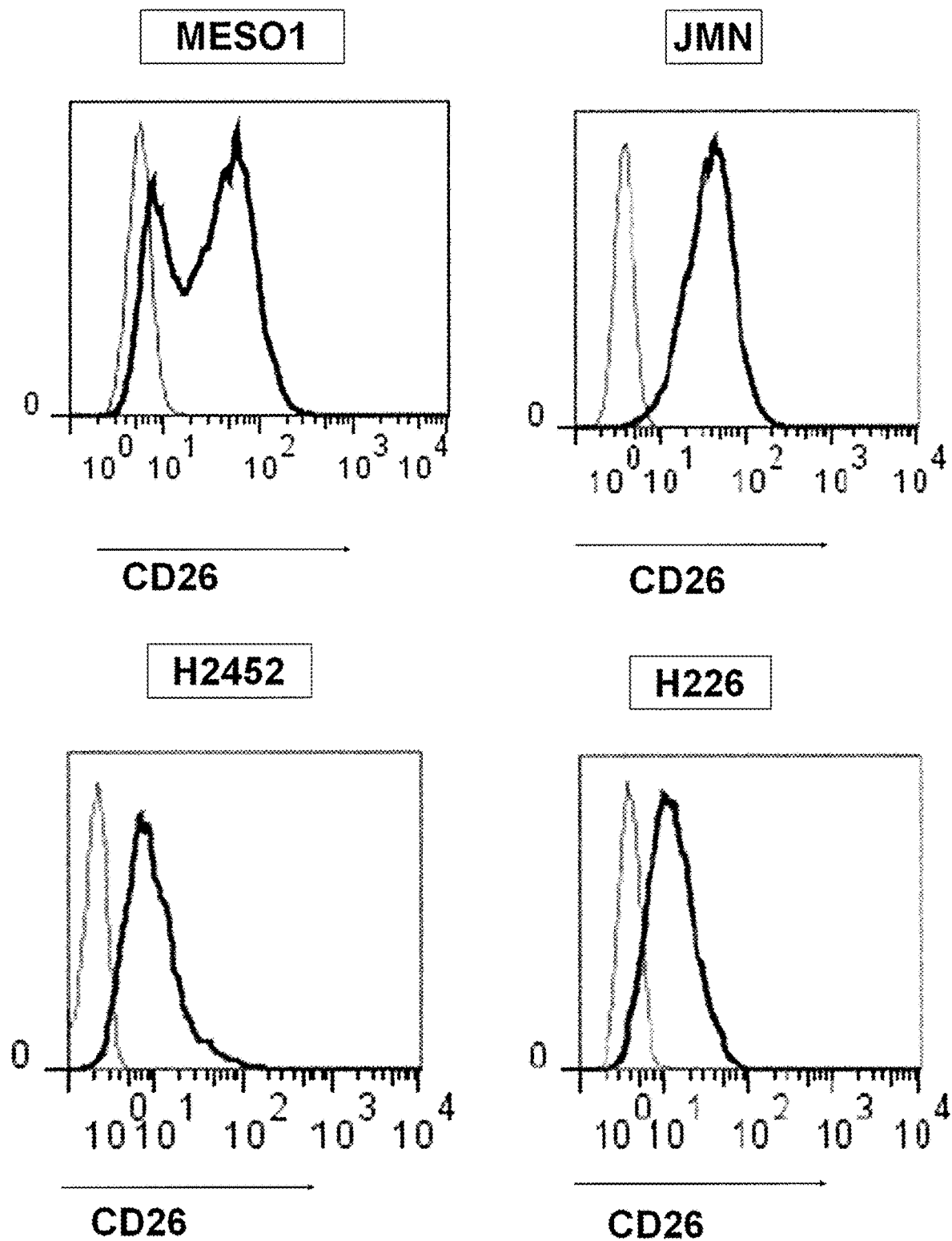
FIG. 8 is a graph of CD26 expression in a mesothelioma cell line. The each tested cell name is indicated above graph.

The results are shown in FIG. 8. All the cell lines tested were confirmed to express CD26.

(Example 8) Potentiation of Cell Growth Inhibitory Effect of Cisplatin-Pemetrexed by Concomitant Use with YS110 on Mesothelioma Cell (1) Dose-Response Curves of Cisplatin and Pemetrexed
MESO1 or H2452 cells ($2\times10^3$ cells/well) were inoculated to a 96-well plate. One hour later, cisplatin or pemetrexed was added thereto at $10^{-9}$, $10^{-8}$, $10^{-7}$, $10^{-6}$, $10^{-5}$, or $10^{-4}$ M (n=6). At day 2, MTT assay was conducted.

Figure 9:
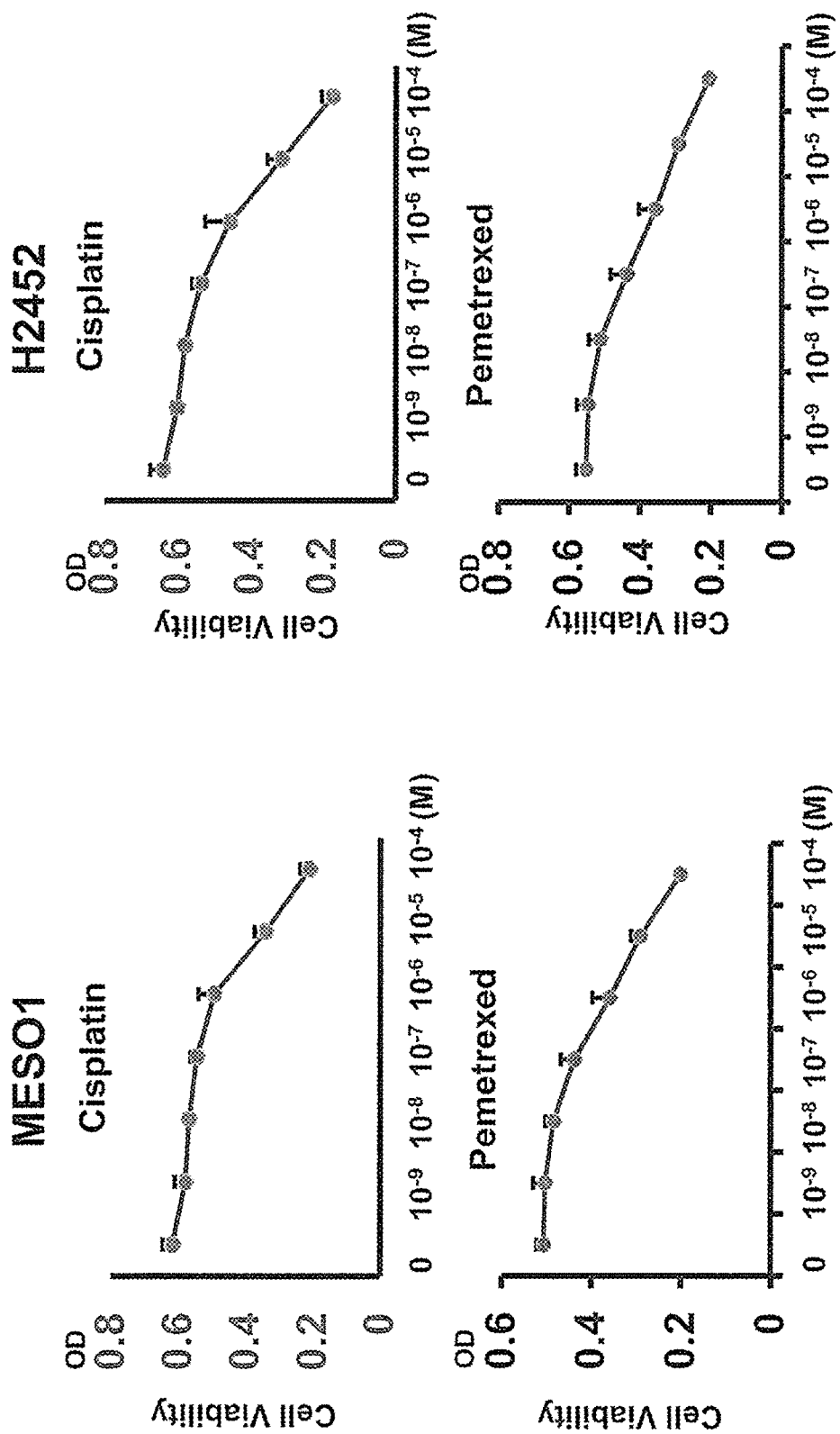
FIG. 9 is a graph of the dose-response curves of cisplatin and pemetrexed. The ordinate indicates viable cells (turbidity: OD), and the abscissa indicates the concentration of cisplatin or pemetrexed. The left graphs are results of using MESO1 cells, and the right graphs are the results of using H2452 cells. The upper graphs are results of cisplatin, and the lower graphs are results of pemetrexed.

The results are shown in FIG. 9. Cisplatin and pemetrexed suppressed the growth of MESO1 and H2452 in a dose-dependent manner.

(2) Potentiation of MESO1 Cell Growth Inhibitory Effects of Cisplatin and Pemetrexed by YS110
MESO1 cells ($2\times10^3$ cells/well) were inoculated to a 96-well plate. One hour later, the combination of 0.3, 3, or 10 μM cisplatin and 0.1, 3, or 10 μg/ml YS110, or the combination of 0.03, 0.3, or 1 μM pemetrexed and 0.1, 3, or 10 μg/ml YS110 was added thereto. At day 2, MTT assay was conducted. Significant difference was tested by two-tailed t-test (vs Cont).

Figure 10A:
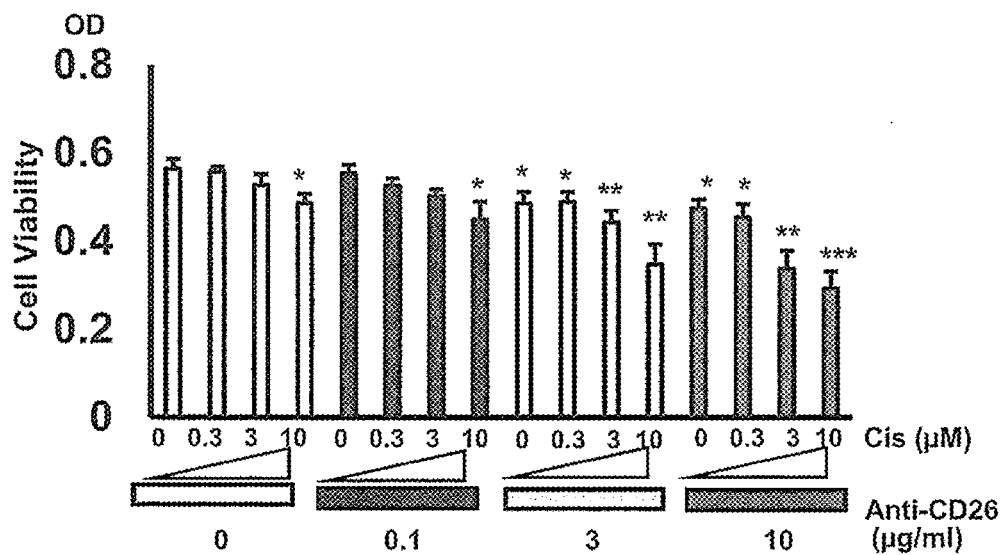
FIG. 10A shows results of cisplatin.
Figure 10B:
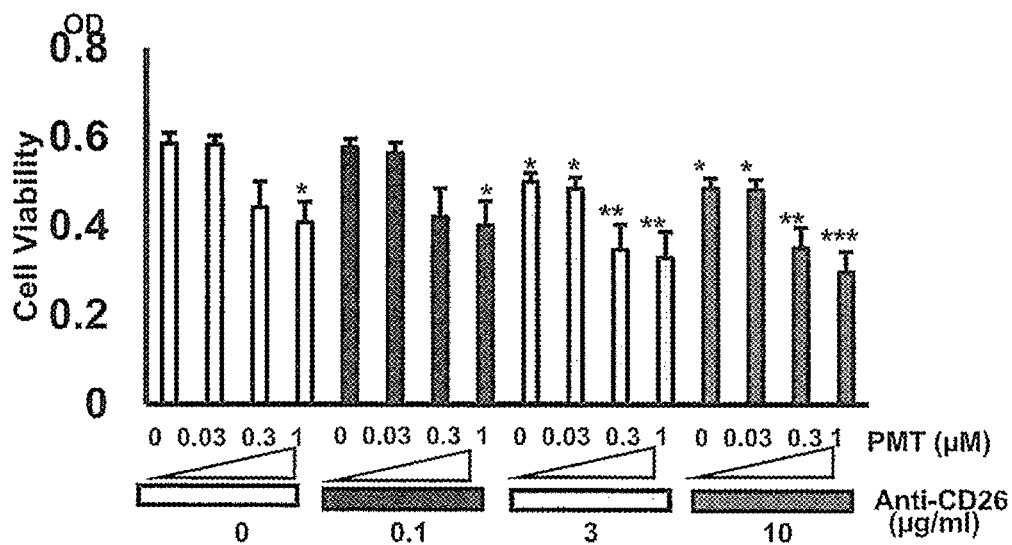
FIG. 10B shows results of pemetrexed. The ordinate indicates viable cells (turbidity: OD), and the abscissa indicates the amount of each drug administered. Anti-CD26 represents the anti-CD26 antibody YS110. $*p<0.05$, $p<0.01$, $*p<0.001$.

The results are shown in FIG. 10. YS110 potentiated the cell growth inhibitory effects of cisplatin and pemetrexed. Pemetrexed
(3) Potentiation of H2452 Cell Growth Inhibitory Effects of Cisplatin and Pemetrexed by YS110
H2452 cells ($2\times10^3$ cells/well) were inoculated to a 96-well plate. One hour later, the combination of 0.03, 0.3, or 1 μM cisplatin and 0.1, 3, or 10 μg/ml YS110, or the combination of 0.01, 0.1, or 0.3 μM pemetrexed and 0.1, 3, or 10 μg/ml YS110 was added thereto (n=6). At day 2, MTT assay was conducted. Significant difference was tested by two-tailed t-test (vs Cont).

Figure 11A:
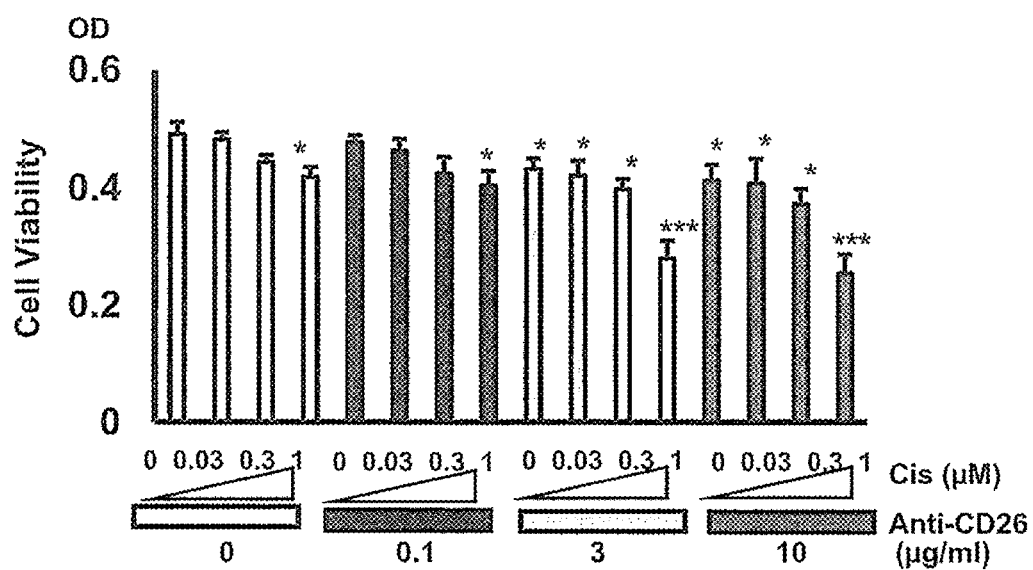
FIG. 11A shows results of cisplatin.
Figure 11B:
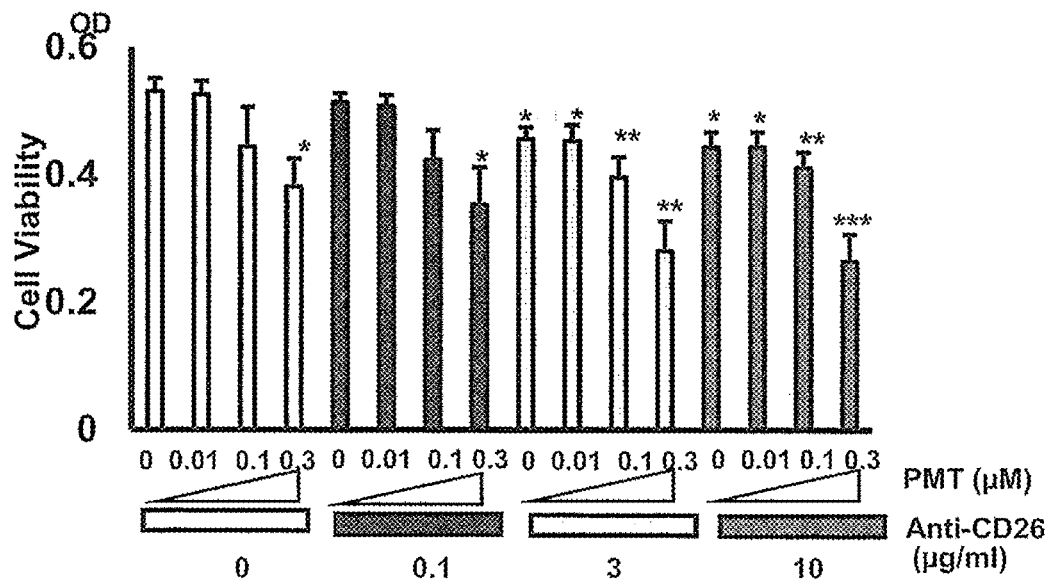
FIG. 11B shows results of pemetrexed. The ordinate indicates viable cells (turbidity: OD), and the abscissa indicates the amount of each drug administered. Anti-CD26 represents the anti-CD26 antibody YS110. $*p<0.05$, $p<0.01$, $*p<0.001$).

The results are shown in FIG. 11. YS110 potentiated the cell growth inhibitory effects of cisplatin and pemetrexed.
(4) Potentiation of MESO1 Cell Growth Inhibitory Effect of Cisplatin-Pemetrexed Concomitant use by YS110
MESO1 cells ($2\times10^3$ cells/well) or H2452 cells ($2\times10^3$ cells/well) were inoculated to a 96-well plate. One hour later, 0.3 μM cisplatin-0.1 μM pemetrexed combination, or YS110 (10 μg/ml) plus the 0.3 μM cisplatin-0.1 μM pemetrexed combination was added thereto (n=6). At day 2, MTT assay was conducted. Significant difference was tested by two-tailed t-test (vs Cont).

Figure 12A:
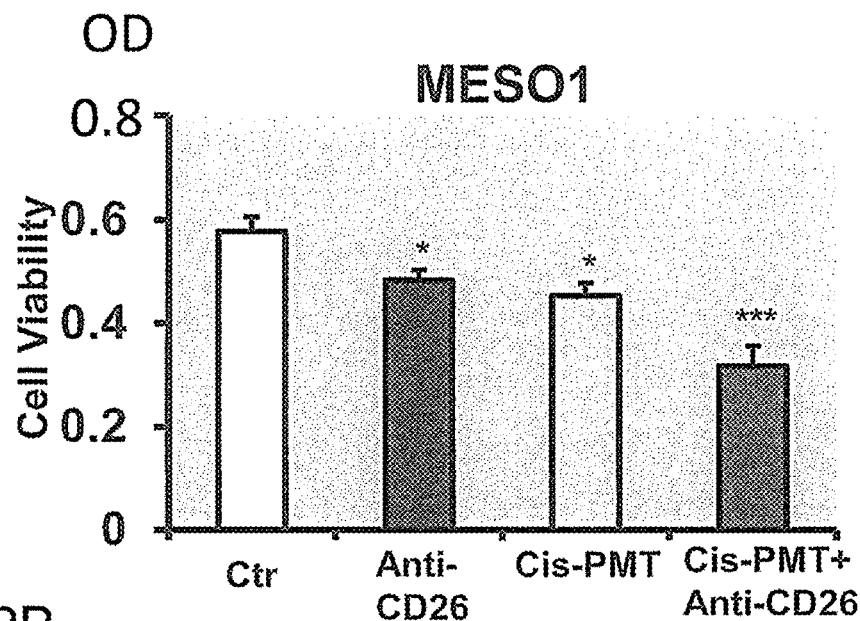
FIG. 12A shows results of MESO1 cells.
Figure 12B:
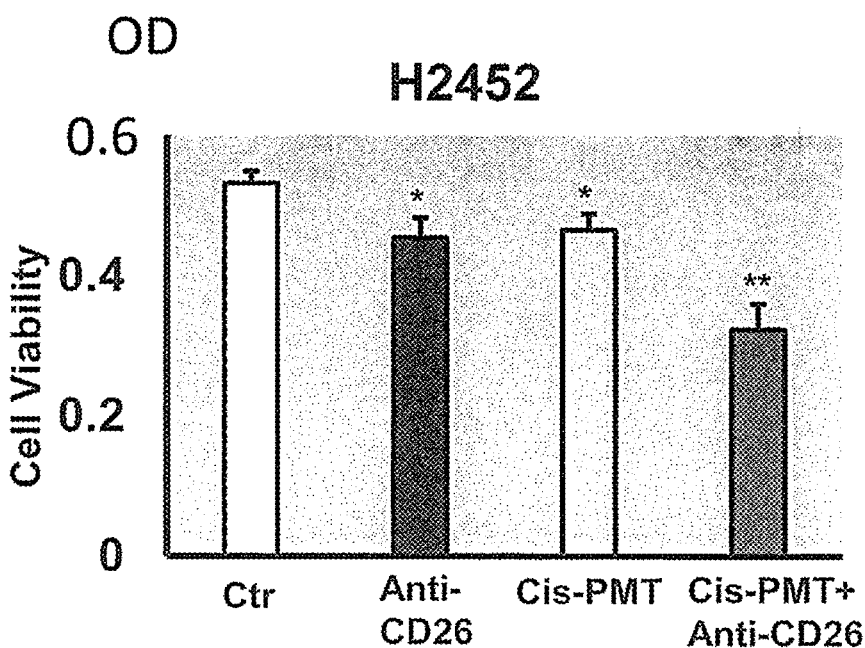
FIG. 12B shows results of H2452 cells. The ordinate indicates viable cells (turbidity: OD), and the abscissa indicates the administered drug. Anti-CD26 represents the anti-CD26 antibody YS110. $*p<0.05$, $p<0.01$, $*p<0.001$.

The results are shown in FIG. 12. YS110 potentiated the cell growth inhibitory effect of cisplatin-pemetrexed.
(5) Potentiation of in Vivo JMN Cell Growth Inhibitory Effects of Cisplatin and Pemetrexed by YS110
JMN cells ($3\times10^5$ cells/animal) were subcutaneously transplanted to the backs of female SCID mice. The day of transplantation was defined as day 0. YS110 (10 mg/kg) alone, cisplatin (0.5 mg/kg) alone, pemetrexed (50 mg/kg) alone, cisplatin (0.5 mg/kg) and YS110 (10 mg/kg) used concomitantly, or pemetrexed (50 mg/kg) and YS110 (10 mg/kg) used concomitantly was intraperitoneally administered to the mice twice (days 1 and 4). At day 7, their tumors were excised, and the tumor weights were measured. Significant difference was tested by two-tailed t-test (vs Cont).

Figure 13:
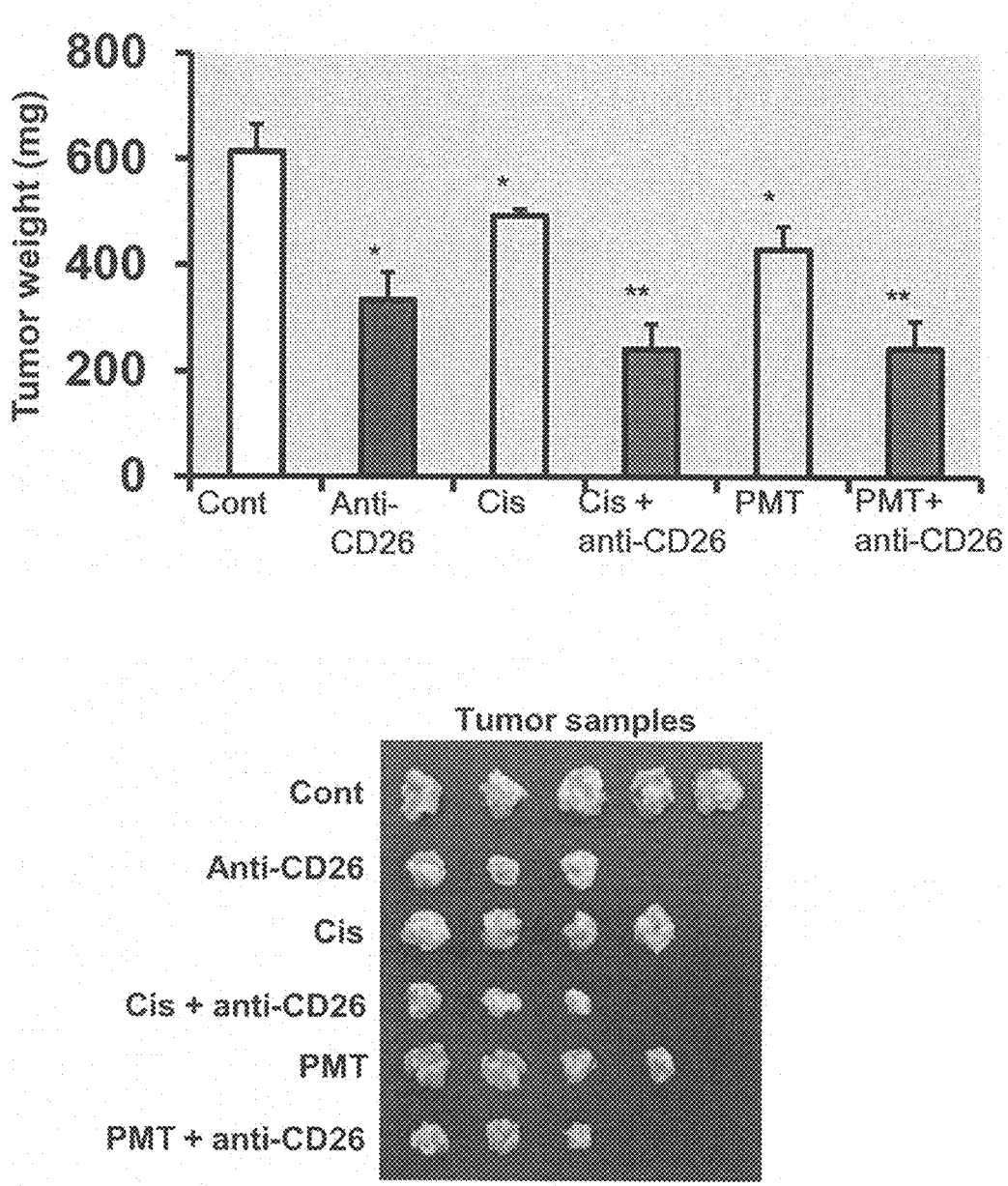
FIG. 13 is a graph and a photograph showing the effect of YS110 on inhibition of in vivo JMN cell growth by cisplatin (Cis) or pemetrexed (PMT). In the graph, the ordinate indicates a tumor weight (mg), and the abscissa indicates the administered drug. The photograph shows excised tumor samples. $*p<0.05$, $**p<0.01$.

The results are shown in FIG. 13. YS110 potentiated the in vivo tumor growth inhibitory effects of cisplatin and pemetrexed.
(6) Potentiation of in Vivo JMN Cell Growth Inhibitory Effect of Cisplatin-Pemetrexed Concomitant use by YS110
JMN cells ($5\times10^3$ cells/animal) were subcutaneously transplanted to the backs of female SCID mice. The day of transplantation was defined as day 0. Cisplatin (0.5 mg/kg)-pemetrexed (50 mg/kg) used concomitantly, YS110 (10 mg/kg) alone, or YS110 (10 mg/kg) used concomitantly with the cisplatin-pemetrexed concomitant use was intraperitoneally administered to the mice twice (days 1 and 4). At day 7, their tumors were excised, and the tumor weights were measured. Significant difference was tested by two-tailed t-test (vs Cont).

Figure 14:
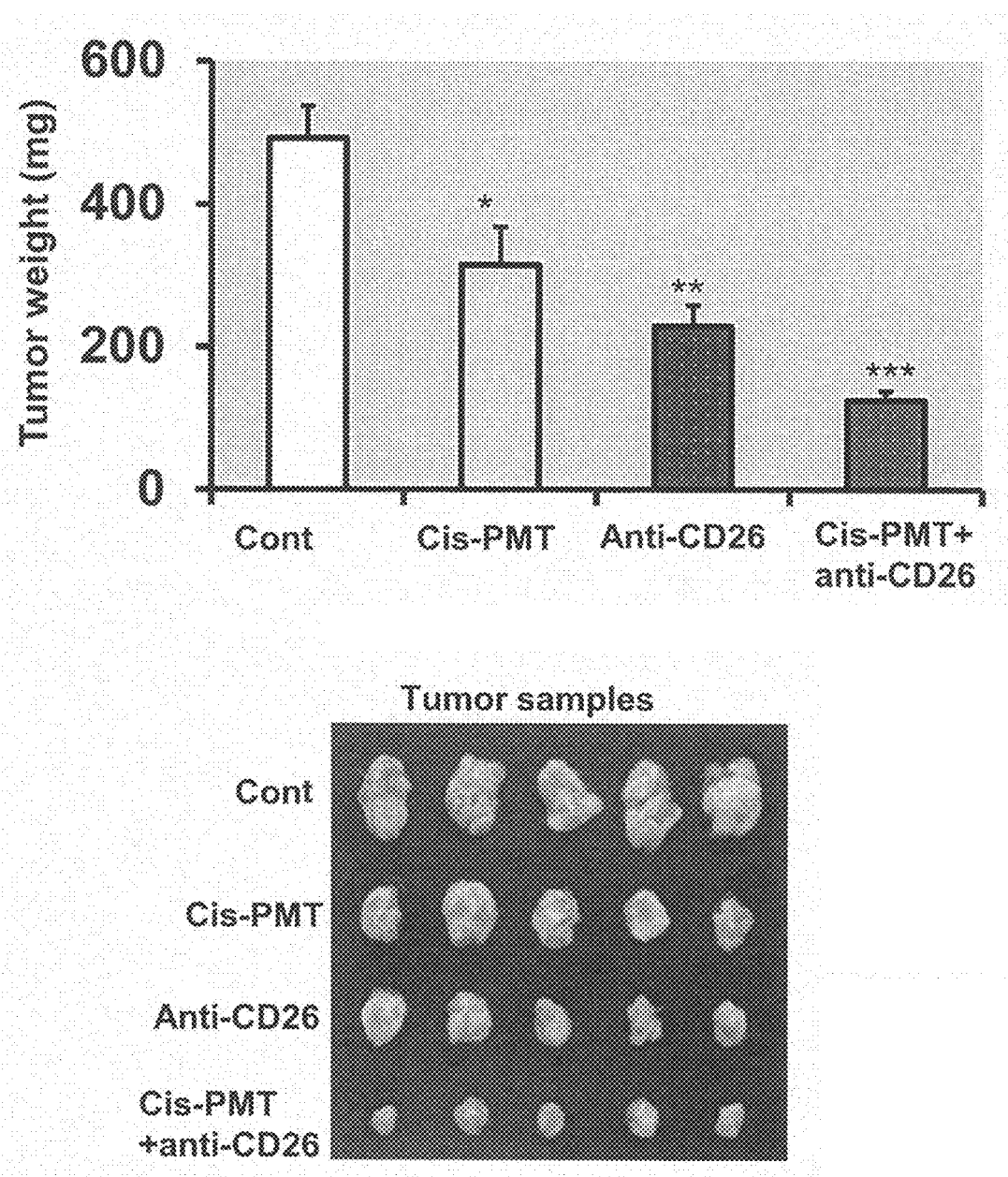
FIG. 14 is a graph and a photograph showing the effect of YS110 on inhibition of in vivo JMN cell growth by cisplatin (Cis)-pemetrexed (PMT) concomitant use. In the graph, the ordinate indicates a tumor weight (mg), and the abscissa indicates the administered drug. The photograph shows excised tumor samples. $*p<0.05$, $p<0.01$, $*p<0.001$.

The results are shown in FIG. 14. YS110 potentiated the in vivo tumor growth inhibitory effect of cisplatin-pemetrexed.
(7) Potentiation of in Vivo MESO1 Cell Growth Inhibitory Effect of Cisplatin-Pemetrexed Concomitant use by YS110
MESO1 cells ($3\times10^5$ cells/animal) were subcutaneously transplanted to the backs of female SCID mice. The day of transplantation was defined as day 0. YS110 (10 mg/kg) alone, cisplatin (0.5 mg/kg)-pemetrexed (50 mg/kg) used concomitantly, or YS110 (10 mg/kg) concomitantly used with the cisplatin-pemetrexed concomitant use was intraperitoneally administered to the mice twice (days 1 and 4). At day 7, their tumors were excised, and the tumor weights were measured. Significant difference was tested by two-tailed t-test (vs Cont).

The results are shown in FIG. 15. YS110 potentiated the in vivo tumor growth inhibitory effect of cisplatin-pemetrexed on MESO1 cells.
(8) Potentiation of in Vivo H2452 Cell Growth Inhibitory Effect of Cisplatin-Pemetrexed Concomitant use by YS110
H2452 cells ($3\times10^5$ cells/animal) were subcutaneously transplanted to the backs of female SCID mice. The day of transplantation was defined as day 0. YS110 (10 mg/kg) alone, cisplatin (0.5 mg/kg)-pemetrexed (50 mg/kg) used concomitantly, or YS110 (10 mg/kg) used concomitantly with the cisplatin-pemetrexed concomitant use was intraperitoneally administered to the mice twice (days 1 and 4). At day 7, their tumors were excised, and the tumor weights were measured. Significant difference was tested by two-tailed t-test (vs Cont).

The results are shown in FIG. 16. YS110 potentiated the in vivo tumor growth inhibitory effect of cisplatin-pemetrexed on H2452 cells.

(Example 9) Potentiation of Cell Invasion Inhibitory Effect of Cisplatin-Pemetrexed by Concomitant Use with YS110 on Mesothelioma Cell (1) Action of Cisplatin and Pemetrexed on Cell Invasion
MESO1 cells or H2452 cells ($2.5\times10^4$ cells/well) were inoculated to a Boyden chamber. One hour later, cisplatin (5, 10, or 30 μM) or pemetrexed (1, 10, or 30 μM) was added thereto (n=5), followed by Boyden chamber invasion assay.

24 hours after the cell inoculation, invasive cells were stained with Diff-Quik-staining kit. Significant difference was tested by two-tailed t-test (vs Cont).

The results are shown in FIG. 17. Cisplatin suppressed invasion at 10 and 30 µM. On the other hand, pemetrexed exhibited no inhibitory action on invasion even at 30 µM.

(2) Cell Invasion Inhibitory Effect of Cisplatin-Pemetrexed Concomitant Use

MESO1 cells or H2452 cells ($2.5 \times 10^4$ cells/well) were inoculated to a Boyden chamber. One hour later, the combination of cisplatin (0, 3, or 10 µM) and pemetrexed (0, 10, or 30 µM) was added thereto (n=5), followed by Boyden chamber invasion assay. 24 hours after the cell inoculation, invasive cells were stained with Diff-Quik-staining kit. Significant difference was tested by two-tailed t-test (vs Cont).

Figure 18A:
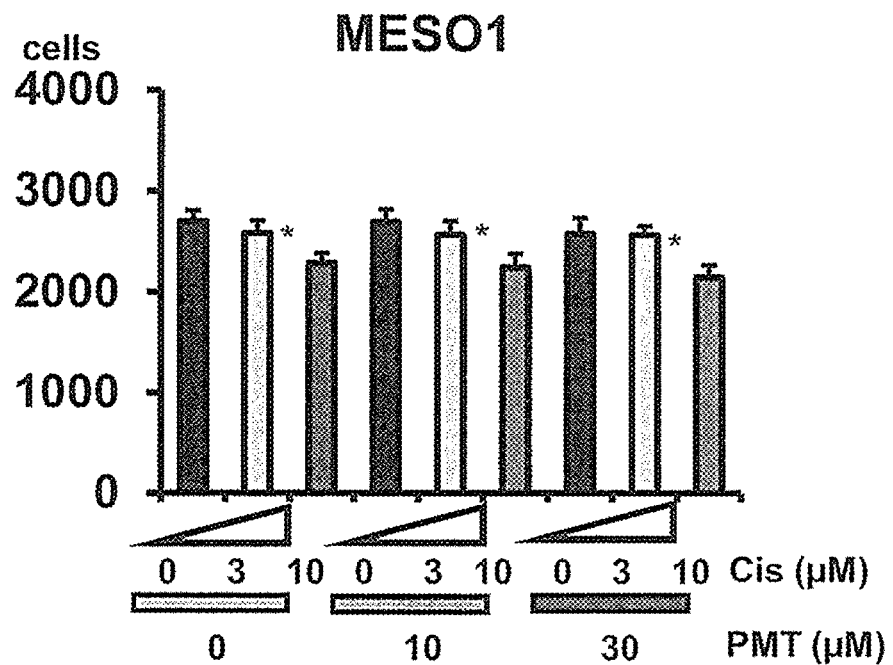
FIG. 18 is a graph of the cell invasion inhibitory effect of concomitant use of cisplatin (Cis)-pemetrexed (PMT). The ordinate indicates the number of invasive cells, and the abscissa indicates the concentration (μM) of each drug. The upper graphs show results of using MESO1 cells, and the lower graphs show results of using H2452 cells. $*p<0.05$, $p<0.01$, $*p<0.001$.
Figure 18B:
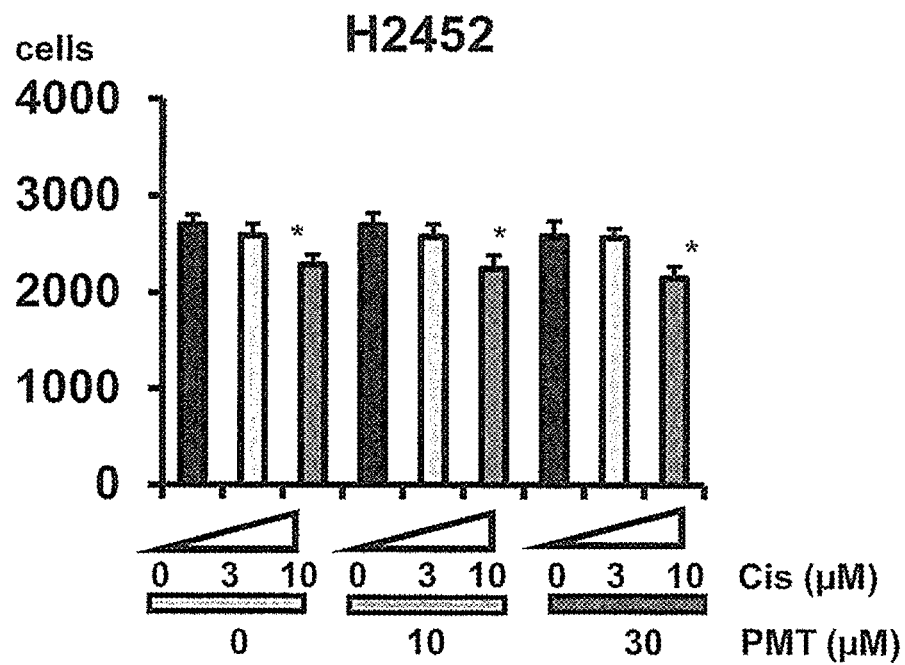

The results are shown in FIG. 18. Cisplatin suppressed cell invasion at 10 µM, whereas pemetrexed did not potentiate the cell invasion inhibitory effect of cisplatin even at 30 µM. These results indicated that the combination of pemetrexed with cisplatin does not potentiate the inhibitory effect on cell invasion, and cisplatin and cisplatin-pemetrexed were equivalent in terms of cell invasion.

(3) YS110 Potentiates Cell Invasion Inhibitory Effect of Cisplatin on MESO1 Cell MESO1 cells ($2.5 \times 10^4$ cells/well) were inoculated to a Boyden chamber. One hour later, the combination of cisplatin (0, 3, or 10 µM) and YS110 (0, 10, or 20 µg/ml) was added thereto (n=5), followed by Boyden chamber invasion assay. 24 hours after the cell inoculation, invasive cells were stained with Diff-Quik-staining kit. Significant difference was tested by two-tailed t-test (vs Cont). Next, the interaction of YS110 with cisplatin-pemetrexed concomitant use was studied. The interaction was analyzed by two-way ANOVA.

The results are shown in FIG. 19. YS110 potentiated the cell invasion inhibitory action of cisplatin-pemetrexed (FIG. 19A). YS110 (10 µg/ml)+cisplatin (10 µM) and YS110 (20 µg/ml)+cisplatin (10 µM) combinations had interaction (FIG. 19B).

(4) YS110 Potentiates Cell Invasion Inhibitory Effect of Cisplatin on H2452 Cell H2452 cells ($2.5 \times 10^4$ cells/well) were inoculated to a Boyden chamber. One hour later, the combination of cisplatin (0, 3, or 10 µM) and YS110 (0, 10, or 20 µg/ml) was added thereto (n=5), followed by Boyden chamber invasion assay. 24 hours after the cell inoculation, invasive cells were stained with Diff-Quik-staining kit. Significant difference was tested by two-tailed t-test (vs Cont). Next, the interaction of YS110 with cisplatin-pemetrexed concomitant use was studied. The interaction was analyzed by two-way ANOVA.

Figures 20A, 20B:
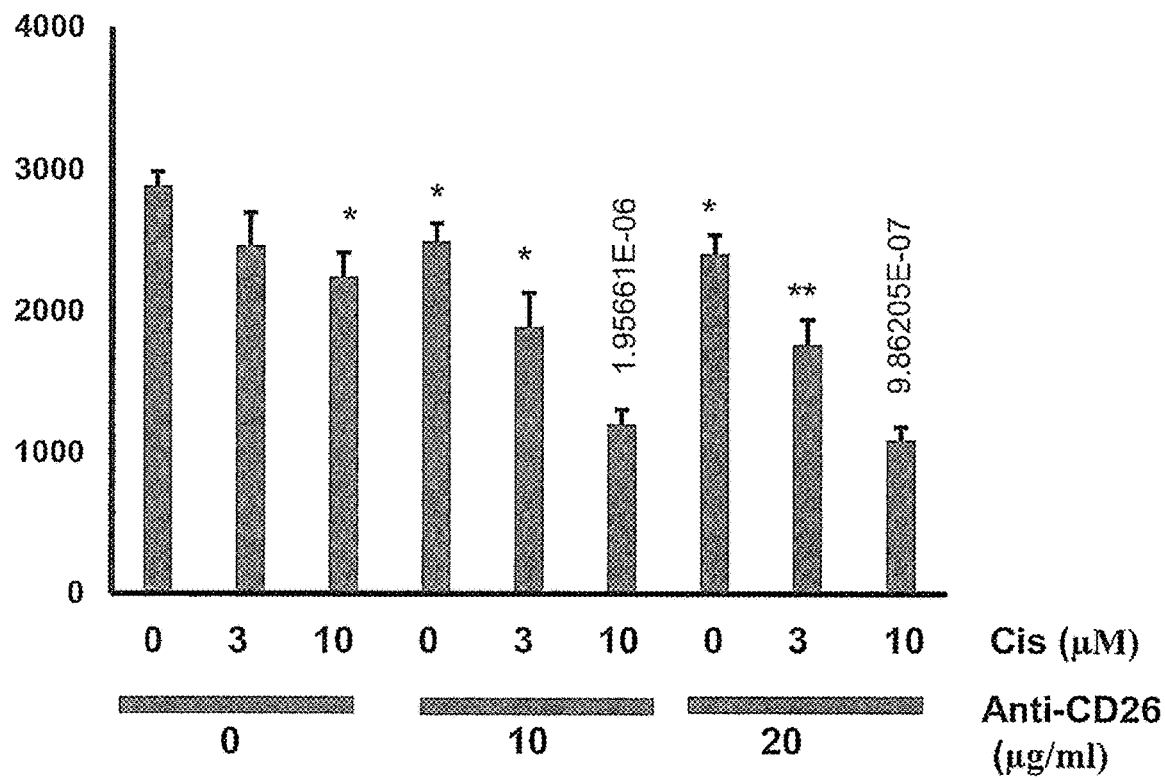
FIG. 20A is a graph showing the H2452 cell invasion inhibitory effect of combination use of YS110 and cisplatin (Cis). The ordinate indicates the number of invasive cells, and the abscissa indicates the concentration (μM) of each drug. $*p<0.05$, $p<0.01$, $*p<0.001$.
FIG. 20B is a table of analyzed interaction of cisplatin with YS110 for a H2452 cell invasion inhibitory effect.

The results are shown in FIG. 20. YS110 synergistically potentiated the cell invasion inhibitory action of cisplatin-pemetrexed (FIG. 20A). YS110 (10 µg/ml)+cisplatin (10 µM) and YS110 (20 µg/ml)+ cisplatin (10 µM) combinations had interaction (FIG. 20B).

(Example 10) Concomitant Use of Gemcitabine and YS110 in Mesothelioma Cell (1) Dose-Response Curve of Gemcitabine in Mesothelioma Cell Line Gemcitabine was studied for its effect on the growth of a mesothelioma cell line. A mesothelioma cell line MESO1, JMN, H2452, or H226 ($2 \times 10^3$ cells/well) was inoculated to a 96-well plate. One hour later, gemcitabine ($10^{-9}$, $10^{-8}$, $10^{-7}$, $10^{-6}$, $10^{-5}$, or $10^{-4}$ M) was added thereto (N=6). 2 days later, MTT assay was conducted. Significant difference was tested by two-tailed t-test (vs Cont).

Figure 21:
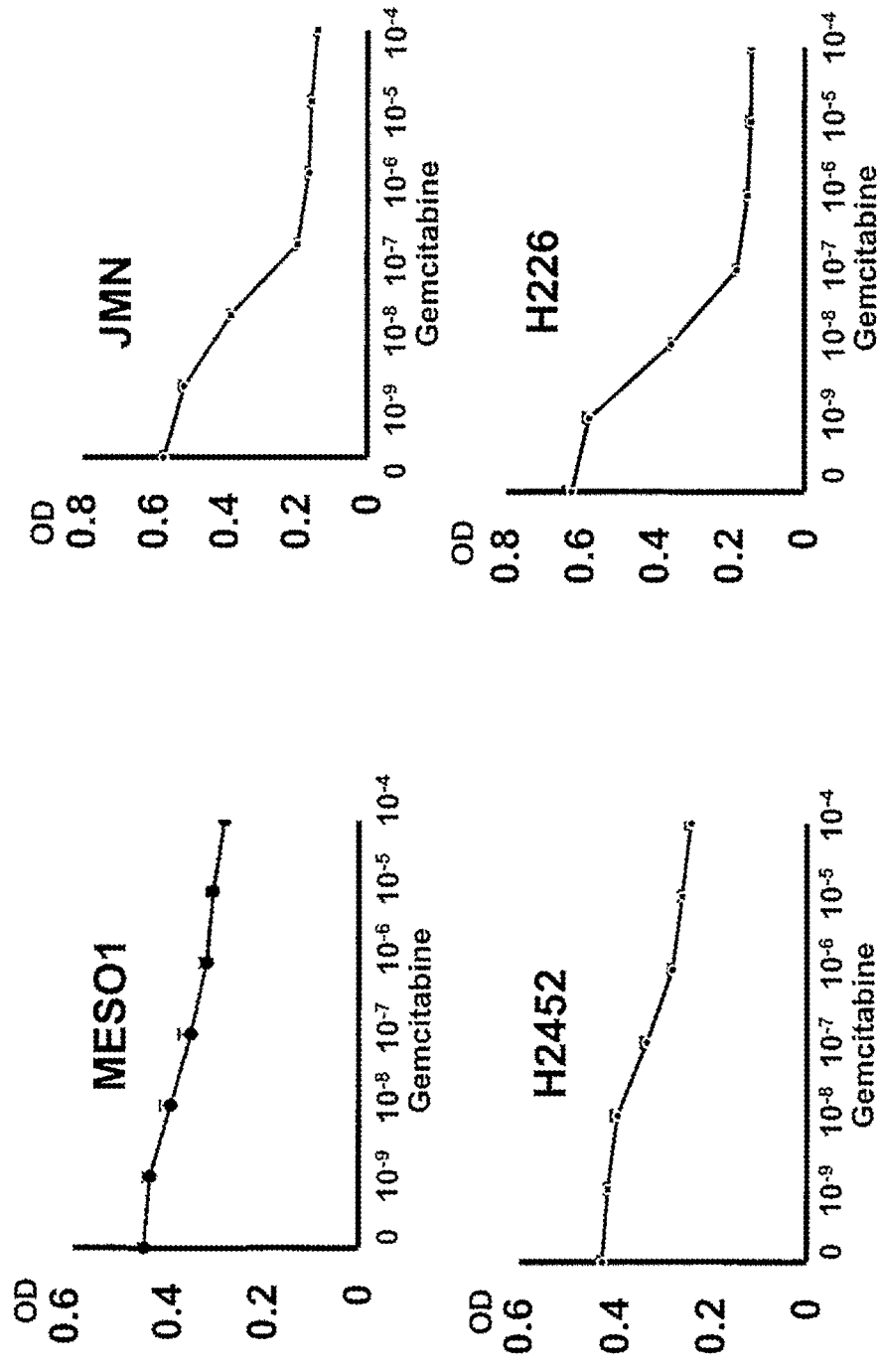
FIG. 21 is a graph of the dose-response curve of gemcitabine against a mesothelioma cell line. The ordinate indicates viable cells (turbidity: OD), and the abscissa indicates the concentration of gemcitabine.

The results are shown in FIG. 21. Gemcitabine more strongly suppressed the growth of JMN and H226.

(2) Effect of YS110 and Gemcitabine Used Concomitantly on Sarcomatoid Mesothelioma MESO1 Cell Growth MESO1 cells ($2 \times 10^3$ cells/well) were inoculated to a 96-well plate. One hour later, gemcitabine (0, $10^{-8}$, $3 \times 10^{-8}$, or $10^{-7}$ M) and YS110 (0, 1, 3, or 10 µg/ml) were added thereto in combination. At day 2, MTT assay was conducted. Significant difference was tested by two-tailed t-test (vs Cont). Next, interaction in concomitant use of medications was studied (n=6). The interaction between YS110 and gemcitabine used concomitantly was analyzed by two-way ANOVA.

Figures 22A, 22B:
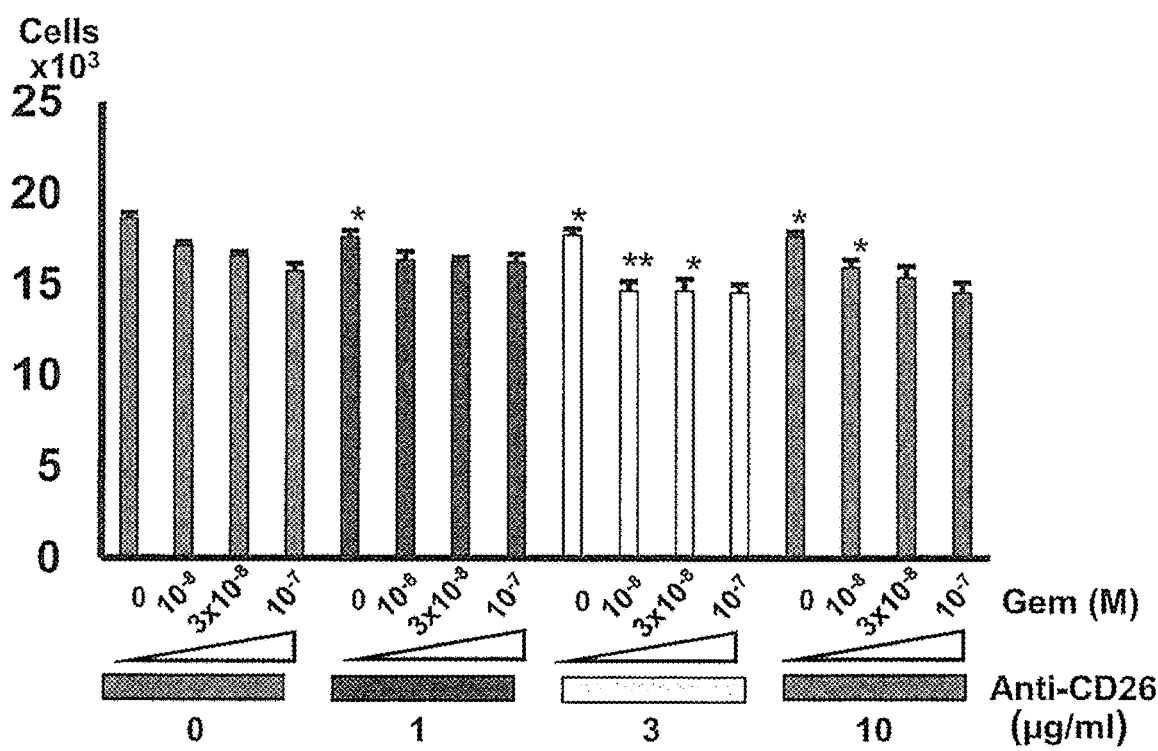
FIG. 22A is a graph of the effect of combination use of YS110 and gemcitabine (Gem) on sarcomatoid mesothelioma MESO1 cell growth. The ordinate indicates the number of cells ($\times 10^3$ cells), and the abscissa indicates the amount of each drug administered. $*p<0.05$, $**p<0.01$.
FIG. 22B is a table of analyzed interaction of gemcitabine with YS110 for a MESO1 cell growth inhibitory effect.

The results are shown in FIG. 22. YS110 potentiated the growth inhibitory effect of gemcitabine (FIG. 22A). Interaction was observed in the combination of gemcitabine ($10^{-8}$ M) and YS110 (3 µg/ml) (FIG. 22B).

(3) Effect of YS110 and Gemcitabine Used Concomitantly on Sarcomatoid Mesothelioma JMN Cell Growth JMN cells ($2 \times 10^3$ cells/well) were inoculated to a 96-well plate. One hour later, gemcitabine (0, $3 \times 10^{-10}$, $10^{-9}$, or $3 \times 10^{-8}$ M) and YS110 (0, 1, 3, or 10 µg/ml) were added thereto in combination. At day 2, MTT assay was conducted. Significant difference was tested by two-tailed t-test (vs Cont). Next, interaction in concomitant use of medications was studied (n=6). The interaction between YS110 and gemcitabine used concomitantly was analyzed by two-way ANOVA.

The results are shown in FIG. 23. YS110 potentiated the growth inhibitory effect of gemcitabine (FIG. 23A). Interaction was observed in the combination of gemcitabine ($3 \times 10^{-8}$ M) and YS110 (3 µg/ml) and the combination of gemcitabine ($3 \times 10^{-8}$ M) and YS110 (10 µg/ml) (FIG. 23B).

(4) Effect of YS110 and gemcitabine used concomitantly on epithelioid mesothelioma H2452 cell growth H2452 cells ($2 \times 10^3$ cells/well) were inoculated to a 96-well plate. One hour later, gemcitabine (0, $10^{-8}$, $3 \times 10^{-8}$, or $10^{-7}$ M) and YS110 (0, 1, 3, or 10 µg/ml) were added thereto in combination. At day 2, MTT assay was conducted. Significant difference was tested by two-tailed t-test (vs Cont). Next, interaction in concomitant use of medications was studied (n=6). The interaction between YS110 and gemcitabine used concomitantly was analyzed by two-way ANOVA.

Figures 24A, 24B:
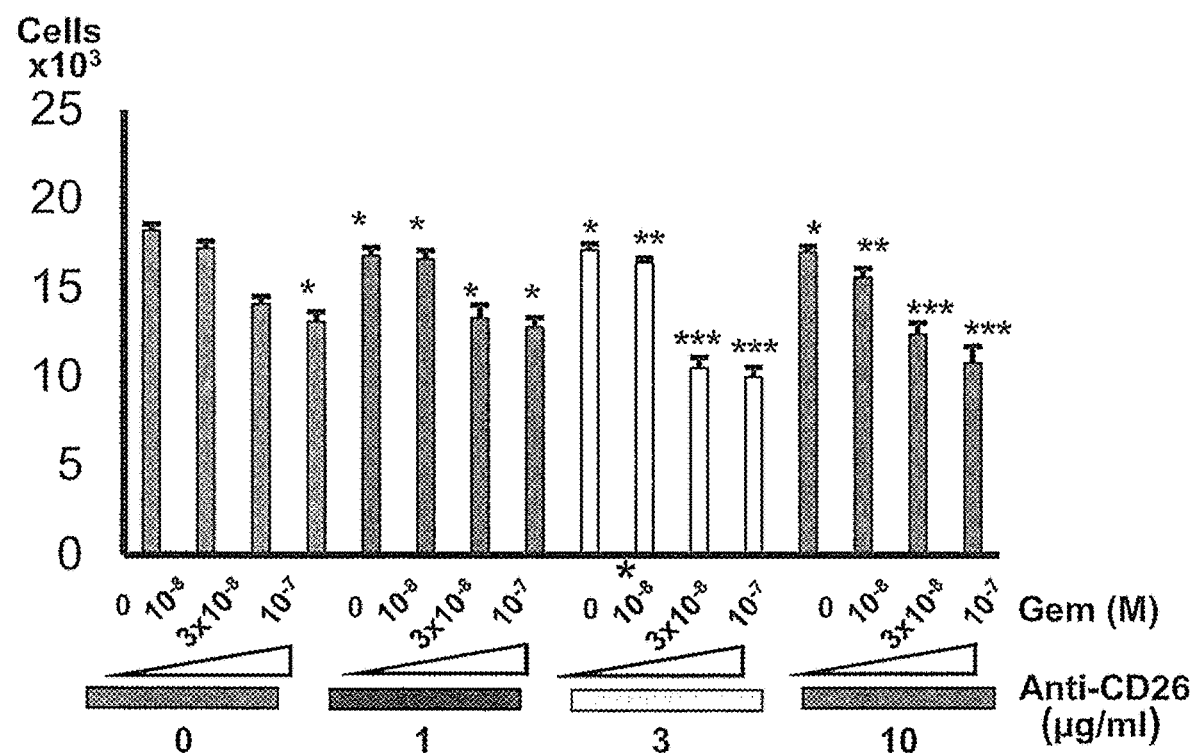
FIG. 24A is a graph of the effect of combination use of YS110 and gemcitabine (Gem) on epithelioid mesothelioma H2452 cell growth. The ordinate indicates the number of cells ($\times 10^3$ cells), and the abscissa indicates the amount of each drug administered. $*p<0.05$, $p<0.01$, $*p<0.001$.
FIG. 24B is a table of analyzed interaction of gemcitabine with YS110 for a H2452 cell growth inhibitory effect.

The results are shown in FIG. 24. YS110 potentiated the growth inhibitory effect of gemcitabine (FIG. 24A). Interaction was observed in the combination of gemcitabine ($10^{-7}$ M) and YS110 (3 µg/ml) (FIG. 24B).

(5) Effect of YS110 and Gemcitabine Used Concomitantly on Epithelioid Mesothelioma H226 Cell Growth H226 cells ($2 \times 10^3$ cells/well) were inoculated to a 96-well plate. One hour later, gemcitabine (0, $10^{-8}$, $3 \times 10^{-8}$, or $10^{-7}$ M) and YS110 (0, 1, 3, or 10 µg/ml) were added thereto in combination. At day 2, MTT assay was conducted. Significant difference was tested by two-tailed t-test (vs Cont). Next, interaction in concomitant use of medications was studied (n=6). The interaction between YS110 and gemcitabine used concomitantly was analyzed by two-way ANOVA.

Figures 25A, 25B:
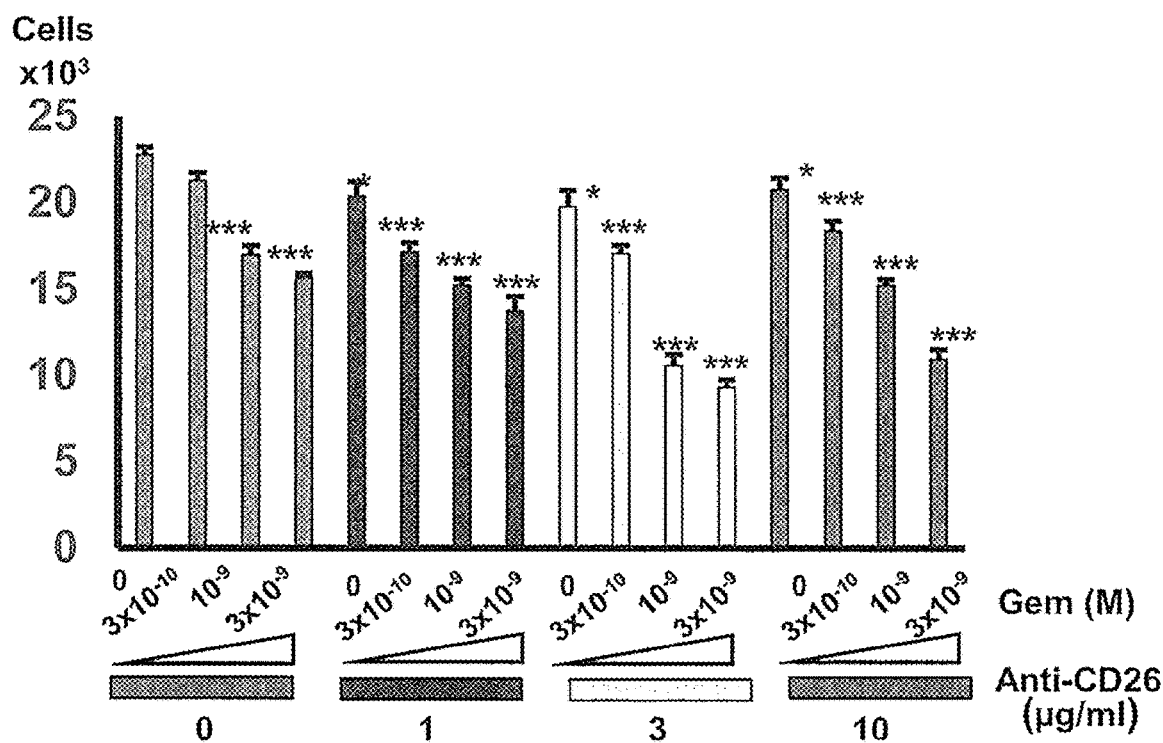
FIG. 25A is a graph of the effect of combination use of the anti-CD26 antibody and gemcitabine (Gem) on epithelioid mesothelioma H226 cell growth. The ordinate indicates the number of cells ($\times 10^3$ cells), and the abscissa indicates the amount of each drug administered. $*p<0.05$, $p<0.01$, $*p<0.001$.
FIG. 25B is a table of analyzed interaction of gemcitabine with YS110 for a H226 cell growth inhibitory effect.

The results are shown in FIG. 25. YS110 potentiated the growth inhibitory effect of gemcitabine (FIG. 25A). Interaction was observed in the combination of gemcitabine ($10^{-8}$ M) and YS110 (3 µg/ml), the combination of gemcitabine ($3 \times 10^{-8}$ M) and YS110 (3 μg/ml), and the combination of gemcitabine ($3 \times 10^{-8}$ M) and YS110 (10 μg/ml) (FIG. 25B).

(6) Concomitant Use of Gemcitabine with Standard Cisplatin-Pemetrexed Therapy

MESO1, JMN, H2452 or H226 cells ($2 \times 10^3$ cells/well were inoculated to a 96-well plate. One hour later, $3 \times 10^{-8}$ M or $10^{-7}$ M gemcitabine was added thereto by concomitant use with the combination of cisplatin (0, 0.1, 0.3, or 1 μM) and pemetrexed (0, 0.03, 0.1, or 0.3 μM) (n=6). At day 2, MTT assay was conducted.

Figure 26:
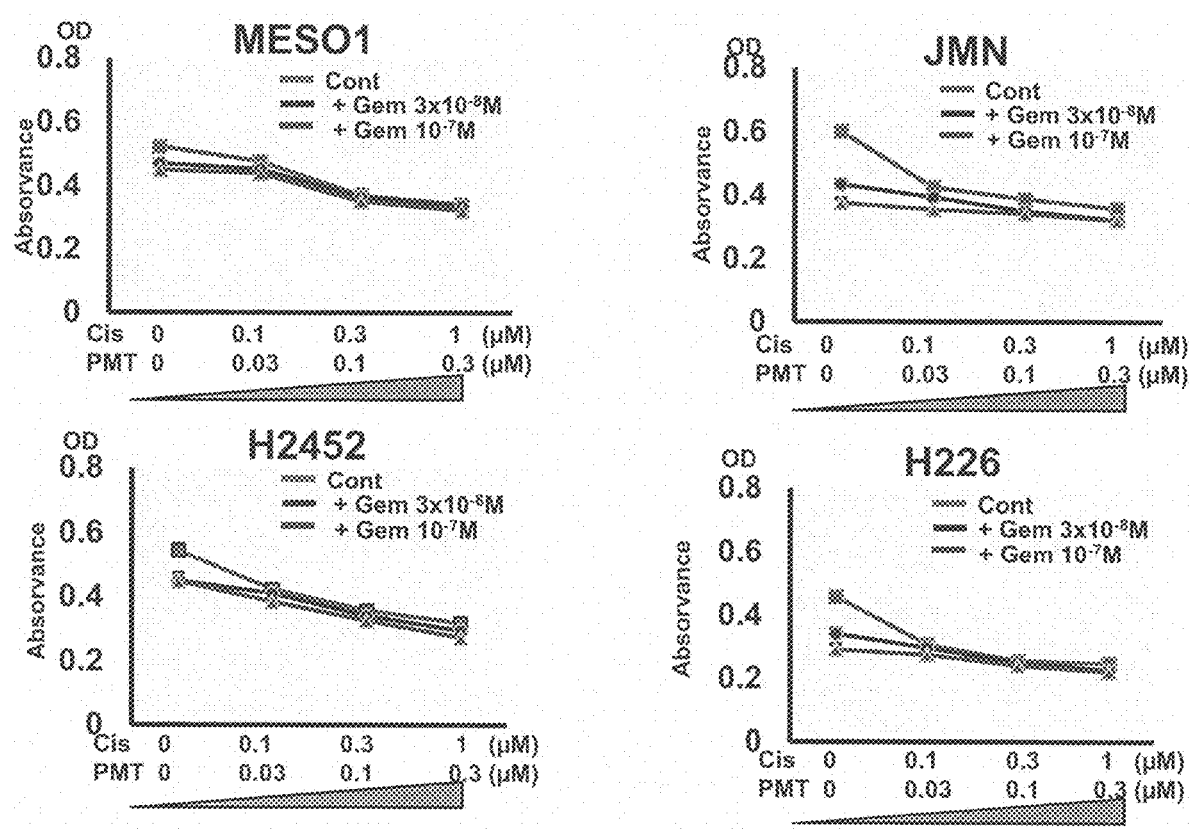
FIG. 26 is a graph of the effect of combination use of gemcitabine (Gem) with cisplatin (Cis)-pemetrexed (PMT). The ordinate indicates viable cells (turbidity: OD), and the abscissa indicates the administered drug. The used cell line name is indicated above the graph. The black square indicates a control group. The black circle indicates a $3\times10^{-8}$ M gemcitabine administration group. The black triangle indicates a $1\times10^{-9}$ M gemcitabine administration group.

The results are shown in FIG. 26. The concomitant use of gemcitabine with cisplatin-pemetrexed combination did not potentiate the growth inhibitory action of cisplatin-pemetrexed.

(7) Concomitant Use of YS110 and Gemcitabine Against in Vivo Growth of Epithelioid Mesothelioma Cell H226

H226 ($3.8 \times 10^5$ cells/animal) was subcutaneously transplanted to the backs of female SCID mice. The day of transplantation was defined as day 0. YS110 (10 mg/kg), gemcitabine (20 mg/kg), or YS110 (10 mg/kg)+gemcitabine (20 mg/kg) was intraperitoneally administered to the mice twice (days 2 and 4) (n=6). At day 7, their tumors were excised, and the tumor weights were measured. Significant difference was tested by two-tailed t-test (vs Cont). The interaction between YS110 and gemcitabine used concomitantly was analyzed by two-way ANOVA.

Figure 27:
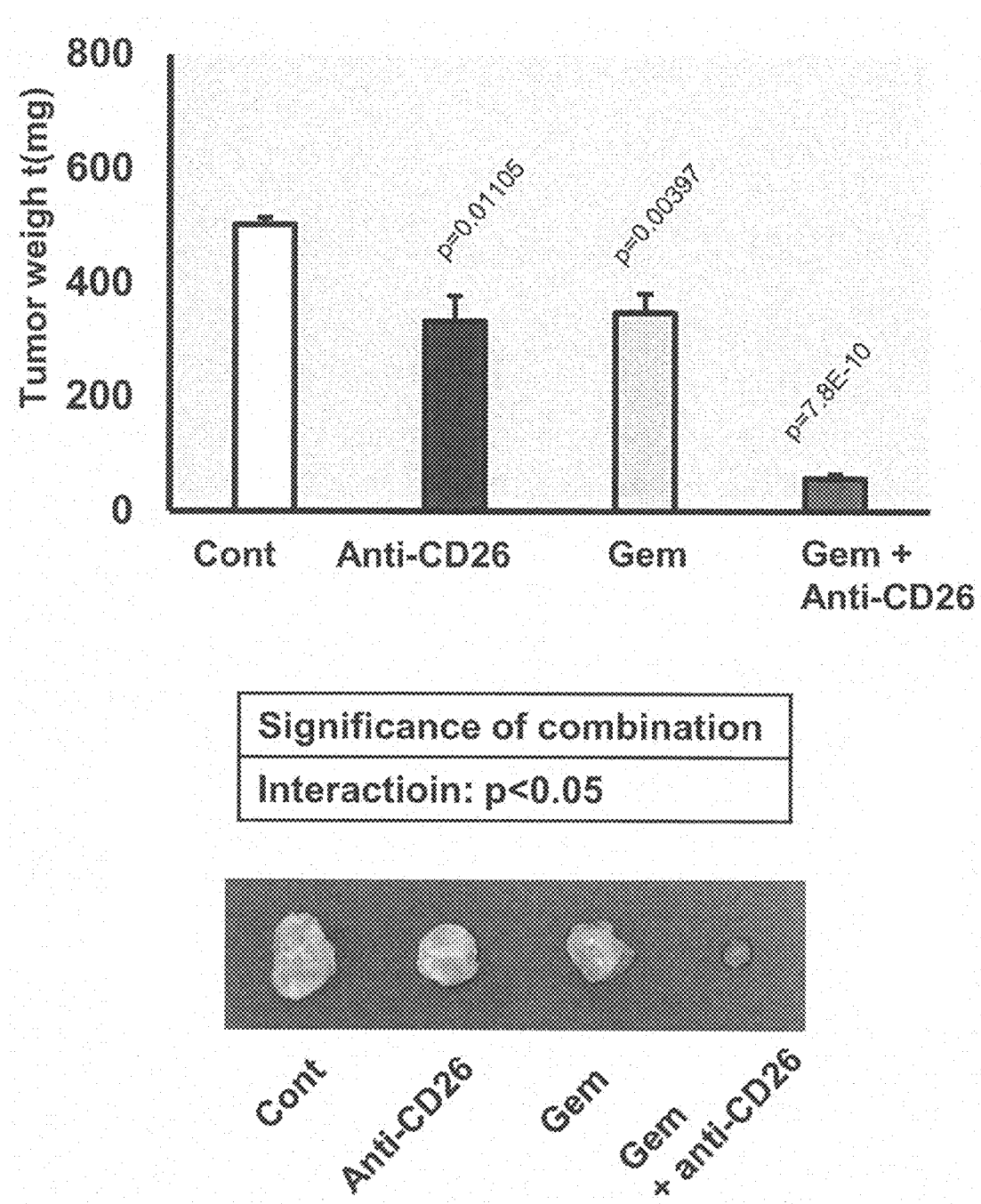
FIG. 27 is a graph and a photograph showing the effect of combination use of YS110 and gemcitabine on the in vivo growth of epithelioid mesothelioma H226 cells, and a table of the interaction of gemcitabine with YS110. In the graph, the ordinate indicates a tumor weight (mg), and the abscissa indicates the administered drug. The photograph shows excised tumor samples.

The results are shown in FIG. 27. The YS110 alone, gemcitabine alone, and YS110+gemcitabine groups exhibited a inhibitory effect of 34%, 29%, and 88%, respectively, and each exhibited a significant inhibitory effect. Interaction was observed in the concomitant use of YS110 and gemcitabine.

(8) Concomitant Use of YS110 and Gemcitabine Against in Vivo Growth of Sarcomatoid Mesothelioma Cell JMN H226 cells ($3 \times 10^5$ cells/animal) were subcutaneously transplanted to the backs of female SCID mice. The day of transplantation was defined as day 0. YS110 (10 mg/kg), gemcitabine (10 mg/kg), or YS110 (10 mg/kg)+gemcitabine (10 mg/kg) was intraperitoneally administered to the mice twice (days 2 and 4) (n=6). At day 7, their tumors were excised, and the tumor weights were measured. Significant difference was tested by two-tailed t-test (vs Cont). The interaction between YS110 and gemcitabine used concomitantly was analyzed by two-way ANOVA.

The results are shown in FIG. 28. The YS110 alone, gemcitabine alone, and YS110+gemcitabine groups exhibited a inhibitory effect of 34%, 29%, and 88%, respectively, and each exhibited a significant inhibitory effect. Interaction was observed in the concomitant use of YS110 and gemcitabine.

(Example 11) Concomitant Use with YS110 Against In Vivo Growth of CD26-Positive Lung Cancer Cell Line (1) Concomitant Use of YS110 and Cisplatin-Pemetrexed Against In Vivo Growth of CD26-Positive Lung Cancer Cell Line HCC827

HCC827 cells ($1.8 \times 10^5$ cells/animal) were subcutaneously transplanted to the backs of female SCID mice. The day of transplantation was defined as day 0. At day 1, YS110 (10 mg/kg) alone, cisplatin (0.5 mg/kg)+pemetrexed (50 mg/kg), or YS110 (10 mg/kg)+cisplatin (0.5 mg/kg)+pemetrexed (50 mg/kg) was intraperitoneally administered to the mice. At day 4, the same amount of the same drug was administered by the same method as in day 1 (n=6). At day 7, their tumors were excised, and the tumor weights were measured. Significant difference was tested by two-tailed t-test (vs Cont).

Figure 29:
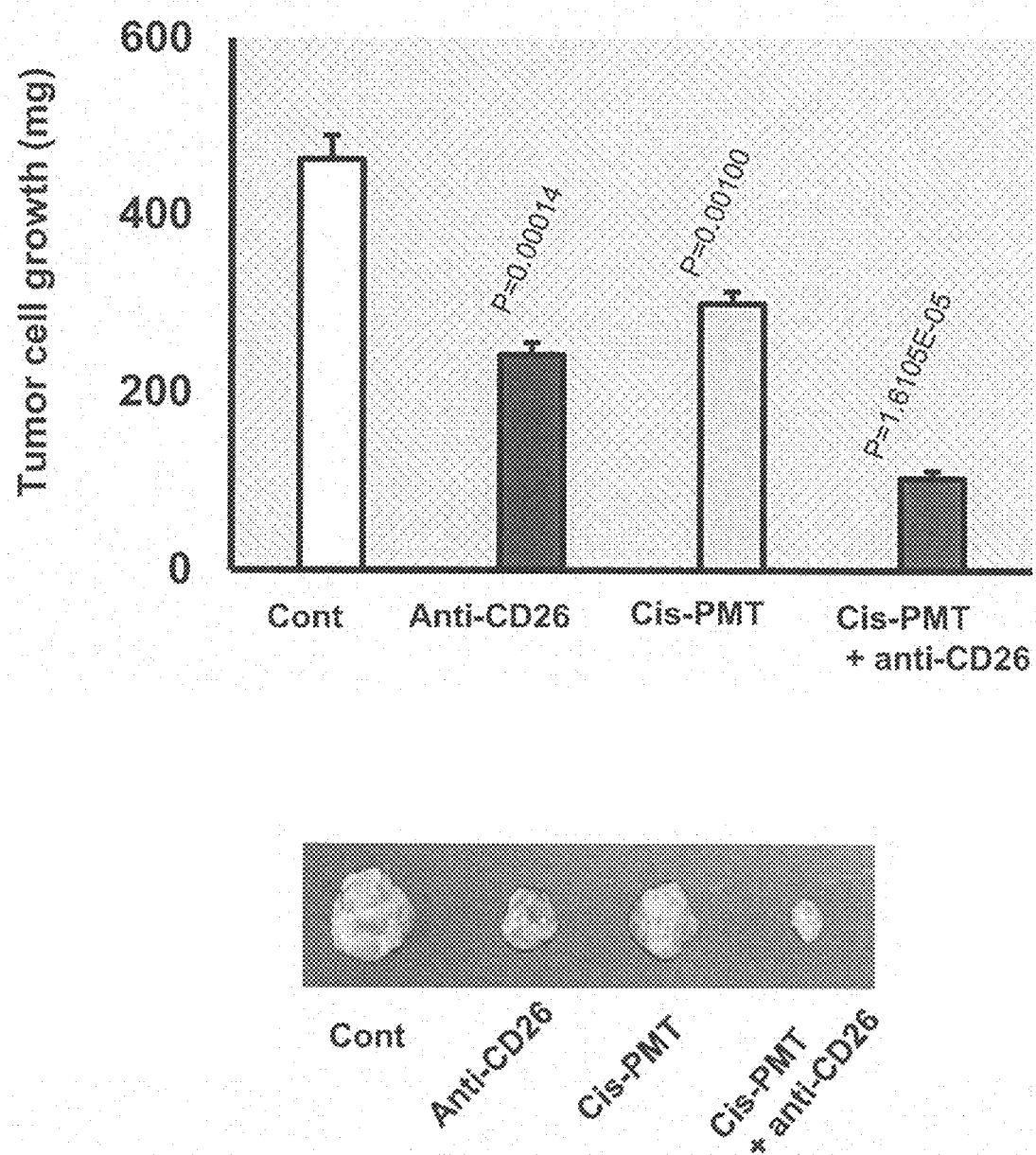
FIG. 29 is a graph showing the effect of combination use of YS110 and cisplatin-pemetrexed on the in vivo growth of CD26-positive lung cancer cell line HCC827 cells. In the graph, the ordinate indicates a tumor weight (mg), and the abscissa indicates the administered drug. The photograph shows excised tumor samples.

The results are shown in FIG. 29. YS110 potentiated the effect of cisplatin-pemetrexed.

(2) Concomitant Use of YS110 and Gefitinib Against In Vivo Growth of CD26-Positive Lung Cancer Cell Line HCC4006 Cell HCC827 cells ($0.5 \times 10^5$ cells/animal) were subcutaneously transplanted to the backs of female SCID mice. The day of transplantation was defined as day 0. YS110 (10 mg/kg, intraperitoneal administration), gefitinib (100 mg/kg, oral administration), or YS110 (10 mg/kg, intraperitoneal administration)+gefitinib (100 mg/kg, oral administration) was administered to the mice twice (days 1 and 4). At day 7, their tumors were excised, and the tumor weights were measured. Significant difference was tested by two-tailed t-test (vs Cont).

Figure 30:
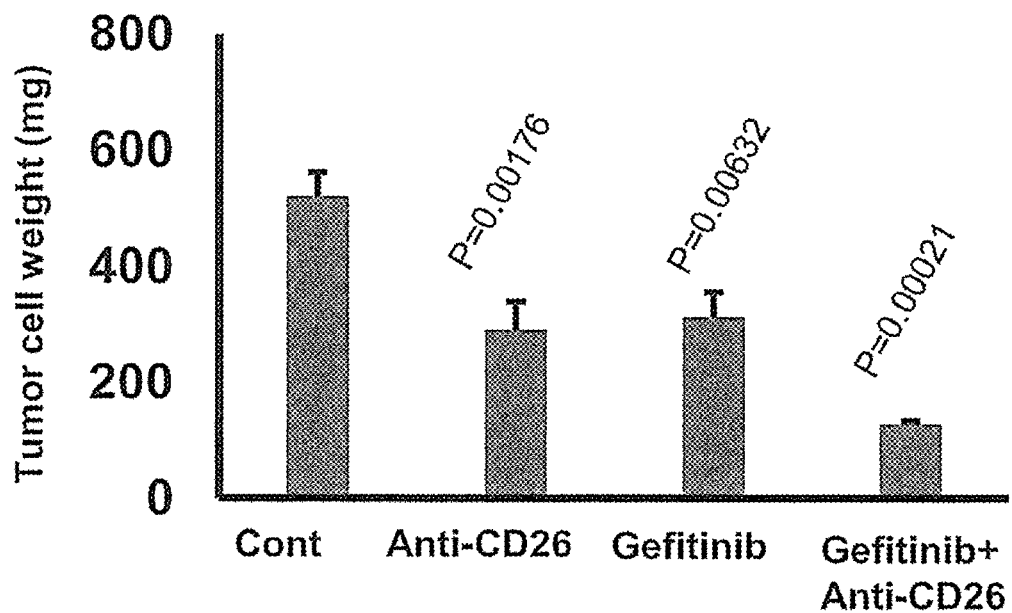
FIG. 30 is a graph showing the effect of combination use of YS110 and gefitinib on the in vivo growth of CD26-positive lung cancer cell line HCC4006 cells. In the graph, the ordinate indicates a tumor weight (mg), and the abscissa indicates the administered drug.

The results are shown in FIG. 30. YS110 potentiated the effect of gefitinib.

(3) Concomitant Use of YS110 and Gefitinib Against in Vivo Growth of CD26-Positive Lung Cancer Cell Line HCC827

HCC827 cells ($0.9 \times 10^5$ cells/animal) were subcutaneously transplanted to the backs of female SCID mice. The day of transplantation was defined as day 0. YS110 (10 mg/kg, intraperitoneal administration), gefitinib (100 mg/kg, oral administration), or YS110 (10 mg/kg, intraperitoneal administration)+gefitinib (100 mg/kg, oral administration) was administered to the mice twice (days 1 and 4). At day 7, their tumors were excised, and the tumor weights were measured. Significant difference was tested by two-tailed t-test (vs Cont).

Figure 31:
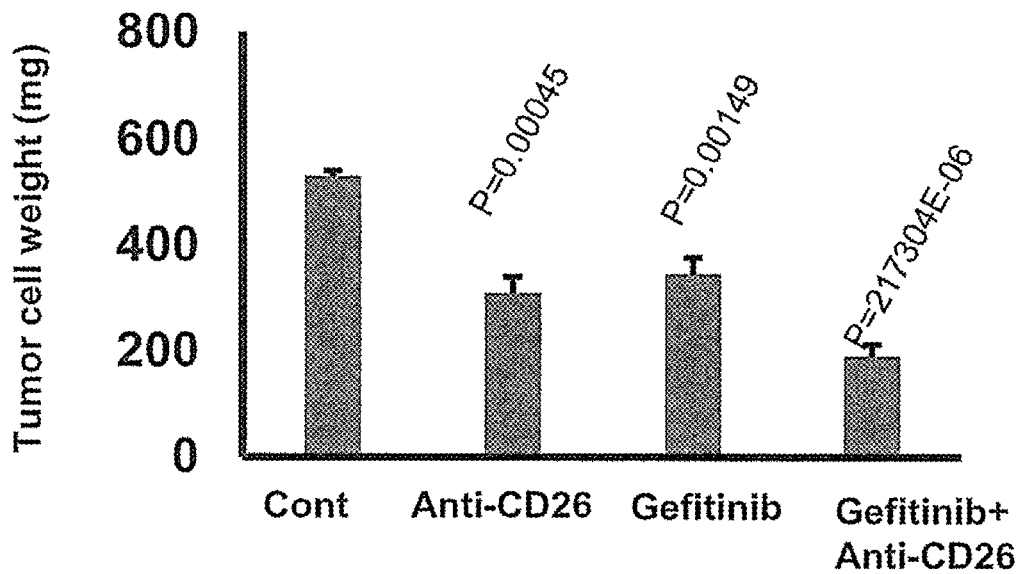
FIG. 31 is a graph showing the effect of combination use of YS110 and gefitinib on the in vivo growth of CD26-positive lung cancer cell line HCC827 cells. In the graph, the ordinate indicates a tumor weight (mg), and the abscissa indicates the administered drug.

The results are shown in FIG. 31. YS110 potentiated the effect of gefitinib.

(Example 12) Study on Screening System to Eetermine Whether Chemotherapeutic can be Expected to Exhibit Synergistic Effect by Concomitant Use with CD26 Antibody Medication therapy is considered to exert a synergistic effect through the mutual action between involved molecules. This suggests the possibility that a chemotherapeutic that exerts an anticancer effect while mutually acting with CD26 can be expected to exhibit a synergistic effect by concomitant use with a CD26 antibody. CD26 and CD9 mutually act and counter with each other (Okamoto et al., PLOS One (2014) 9 (1): e86671). This suggests the possibility that the effect of a chemotherapeutic that mutually acts with CD26 is attenuated by CD9. Accordingly, mesothelioma cell lines MESO1 and H2452 coexpressing CD26 and CD9 and cell lines JMN and H226 expressing CD26 but expressing no CD9 were used in study on the setting of a screening system to determine whether a chemotherapeutic could be expected to exhibit a synergistic effect by concomitant use with a CD26 antibody.

(1) Comparison of Growth Inhibitory Effects of Cisplatin and Pemetrexed Using MESO1 and JMN Cell Lines The growth inhibitory effects of cisplatin ($10^{-9}$ to $10^{-4}$ M) and pemetrexed ($10^{-9}$ to $10^{-4}$ M) were compared using the MESO1 and JMN cell lines.

Figure 32A:
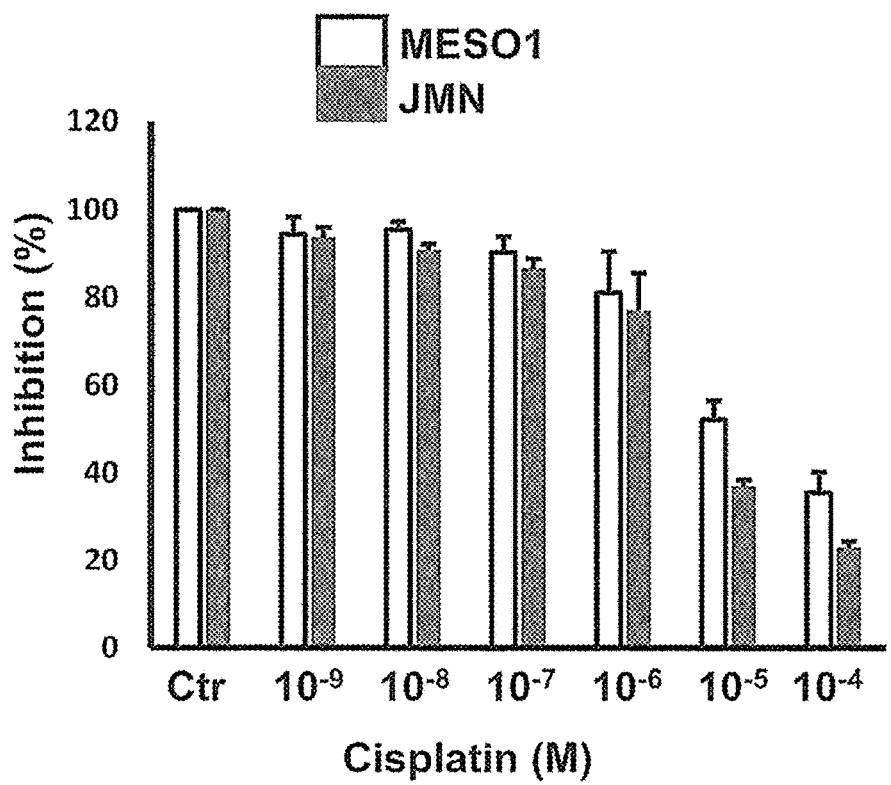
FIG. 32A shows the results comparing the growth inhibitory effect of cisplatin.
Figure 32B:
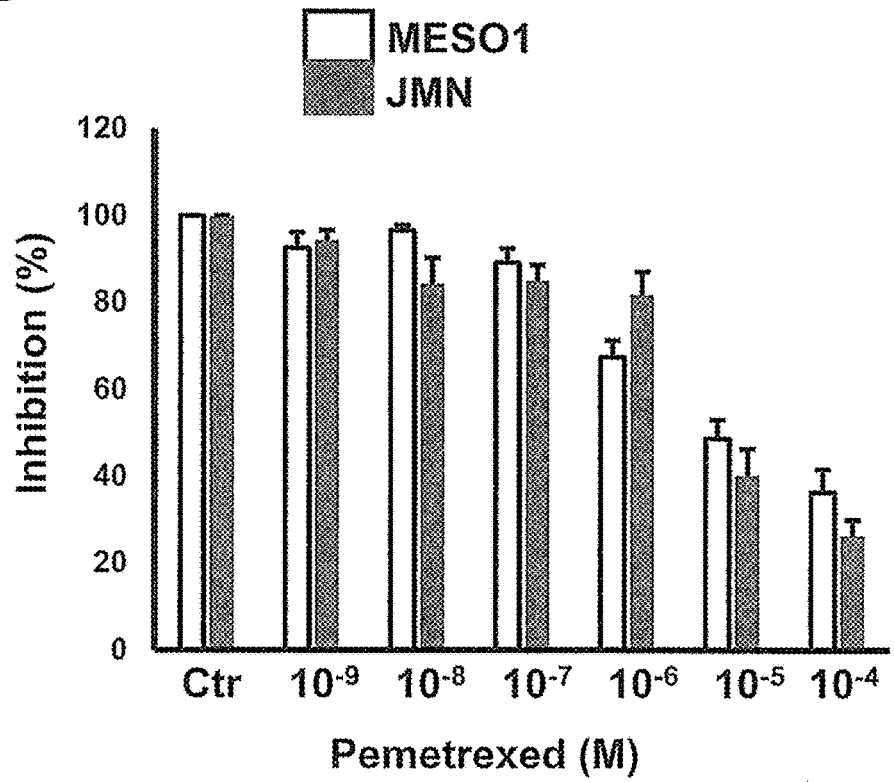
FIG. 32B shows the results comparing the growth inhibitory effect of pemetrexed.

The results are shown in FIG. 32. FIG. 32A shows that as a result of comparing the growth inhibitory effect of cisplatin, the growth inhibitory effect of cisplatin did not differ between MESO1 and JMN. FIG. 32B shows that as a result of comparing the growth inhibitory effect of pemetrexed, the growth inhibitory effect of pemetrexed did not differ between MESO1 and JMN. These results suggested the possibility that a synergistic effect is expected neither in the concomitant use of the anti-CD26 antibody and cisplatin nor in the concomitant use of the anti-CD26 antibody and pemetrexed.

(2) Comparison of Growth Inhibitory Effect of Gemcitabine Using MESO1, H2452, JMN, and H226 Cell Lines The growth inhibitory effect of gemcitabine ($10^{-9}$ to $10^{-4}$ M) was compared using MESO1, H2452, JMN, and H226 cell lines.

Figure 33A:
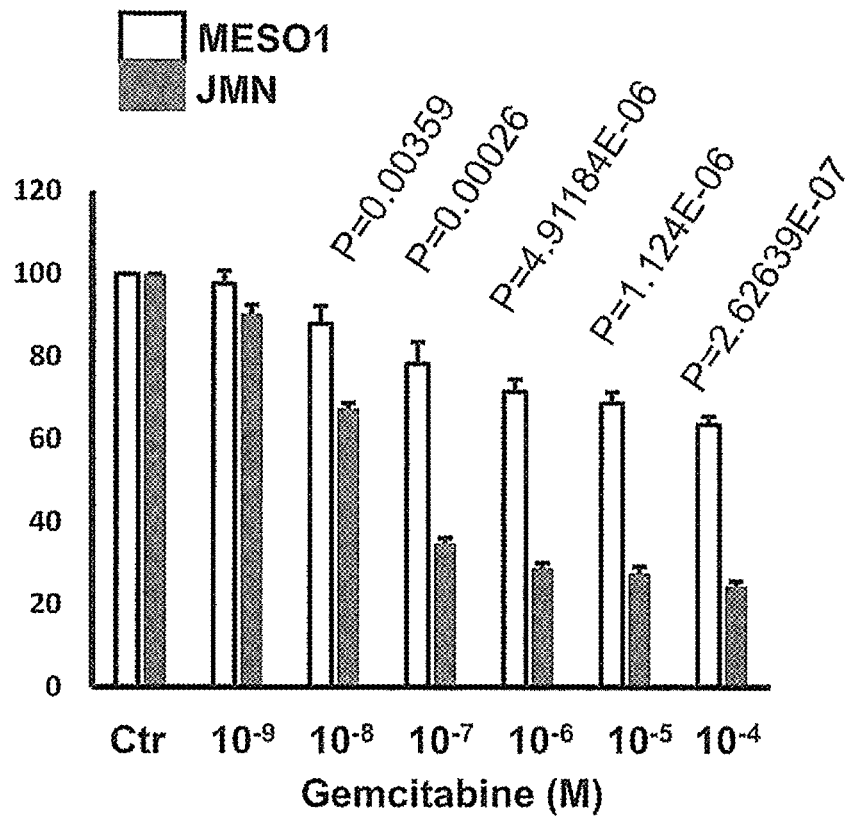
FIG. 33A shows the results of comparing the growth inhibitory effect of gemcitabine between MESO1 and JMN.
Figure 33B:
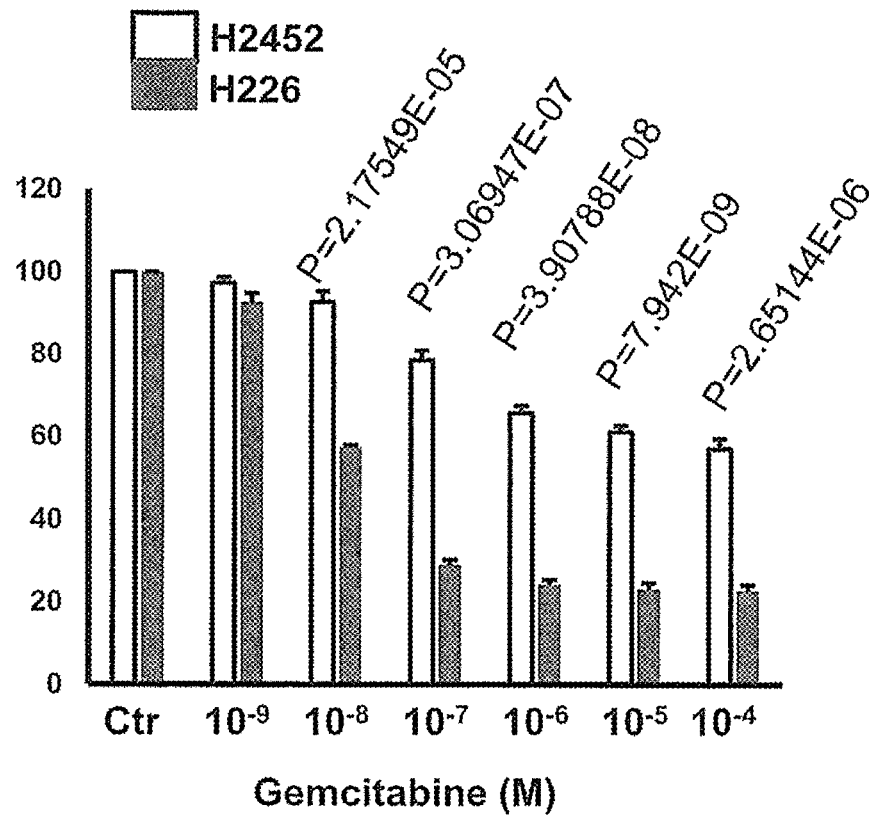
FIG. 33B shows the results of comparing the growth inhibitory effect of gemcitabine between H2452 and H226.

The results are shown in FIG. 33. FIG. 33A shows that as a result of comparing the growth inhibitory effect of gemcitabine between MESO1 and JMN, gemcitabine exhibited a significantly stronger growth inhibitory effect on JMN than on MESO1. FIG. 33B shows that as a result of comparing the growth inhibitory effect of gemcitabine between H2452 and H226, gemcitabine exhibited a significantly stronger growth inhibitory effect on H226 than on H2452. In the comparison between MESO1 and JMN and between H2452 and H226, the stronger growth inhibitory effect of gemcitabine was observed in JMN and H226 expressing no CD9. These results suggested that the possibility that a synergistic effect can be expected in the concomitant use of the anti-CD26 antibody and gemcitabine.

As described above, cisplatin and pemetrexed did not differ in growth inhibitory effect between MESO1 cells (CD9+) and JMN cells (CD9−). In the experiments mentioned above, the concomitant use of the anti-CD26 antibody with cisplatin or pemetrexed was confirmed to have an additive effect, indicating that a synergistic effect is obtained by concomitant use with the anti-CD26 antibody when there is no difference in growth inhibitory effect between MESO1 cells (CD9+) and JMN cells (CD9−−. On the other hand, gemcitabine exhibited significant difference in growth inhibitory effect between MESO1 (CD9+) and JMN (CD9−) and between H2452 (CD9+) and H226 (CD9−). In the experiments mentioned above, the concomitant use of the anti-CD26 antibody with gemcitabine was confirmed to have a synergistic effect, indicating that a synergistic effect is obtained by concomitant use with the anti-CD26 antibody when there is a difference in growth inhibitory effect between CD9+ cells and CD9− cells. These results indicated that a chemotherapeutic that brings about a synergistic effect by concomitant use with a CD26 antibody can be screened for by using cells coexpressing CD26 and CD9 (e.g., MESO1 or H2452) and cells expressing CD26 but expressing no CD9 (JMN or H226).

---

What is claimed is:

1. A conjugate comprising an anti-CD26 antibody or a F(ab')$_2$ fragment thereof which is linked to triptolide,
   wherein the anti-CD26 antibody or the F(ab')$_2$ fragment thereof specifically binds to CD26, comprising: (a) a CDRH1 amino acid sequence of SEQ ID NO: 30, a CDRH2 amino acid sequence of SEQ ID NO: 31, a CDRH3 amino acid sequence of SEQ ID NO: 32, a CDRL1 amino acid sequence of SEQ ID NO: 33, a CDRL2 amino acid sequence of SEQ ID NO: 34, and a CDRL3 amino acid sequence of SEQ ID NO: 35; or (b) a CDRH1 amino acid sequence of SEQ ID NO: 36, a CDRH2 amino acid sequence of SEQ ID NO: 37, a CDRH3 amino acid sequence of SEQ ID NO: 38, a CDRL1 amino acid sequence of SEQ ID NO: 39, a CDRL2 amino acid sequence of SEQ ID NO: 40, and a CDRL3 amino acid sequence of SEQ ID NO: 41.

2. The conjugate of claim 1, wherein the anti-CD26 antibody or the F(ab')$_2$ fragment thereof is a humanized antibody or a fragment thereof.

3. The conjugate of claim 2, wherein the humanized antibody or the F(ab')$_2$ fragment thereof comprises a heavy chain variable region comprising an amino acid sequence having 80% or more identity to an amino acid sequence of SEQ ID NO: 8, and a light chain variable region comprising an amino acid sequence having 80% or more identity to an amino acid sequence of SEQ ID NO: 4.

4. The conjugate of claim 2, wherein the humanized antibody or the F(ab')$_2$ fragment thereof comprises a heavy chain variable region comprising an amino acid sequence of SEQ ID NO 8, and a light chain variable region comprising an amino acid sequence of SEQ ID NO 4.

5. The conjugate of claim 2, wherein the humanized antibody comprises at least one heavy chain comprising an amino acid sequence having 90% or more sequence identity to the amino acid sequence of SEQ ID NO: 17, and at least one light chain comprising an amino acid sequence having 90% or more sequence identity to the amino acid sequence of SEQ ID NO: 18.

6. The conjugate of claim 2, wherein the humanized antibody comprises at least one heavy chain comprising an amino acid sequence from position 20 to position 465 of the amino acid sequence of SEQ ID NO: 17, and at least one light chain comprising an amino acid sequence from position 21 to position 234 of the amino acid sequence of SEQ ID NO: 18.

7. The conjugate of claim 2, wherein the humanized antibody is produced by a strain designated as s604069.YST-pABMC148 (x411) under deposition No. PTA-7695 of the American Type Culture Collection (ATCC).

8. A method for inhibiting CD26-expressing malignant mesothelioma cell growth comprising administering a conjugate of claim 1.

9. A method for lysing a CD26-expressing malignant mesothelioma cell comprising administering a conjugate of claim 1.

10. A method of treatment of CD26-expressing malignant mesothelioma, comprising administering to a patient in need thereof a pharmaceutical composition comprising a conjugate of claim 1.

* * * * *

SEQUENCE LISTING

```
<160> NUMBER OF SEQ ID NOS: 41

<210> SEQ ID NO 1
<211> LENGTH: 107
<212> TYPE: PRT
<213> ORGANISM: Artificial Sequence
<220> FEATURE:
<223> OTHER INFORMATION: Synthetic peptide

<400> SEQUENCE: 1

Asp Ile Leu Met Thr Gln Ser Pro Ser Ser Leu Ser Ala Ser Pro Gly
1               5                   10                  15

Asp Arg Val Thr Ile Ser Cys Arg Ala Ser Gln Asp Ile Arg Asn Asn
            20                  25                  30

Leu Asn Trp Tyr Gln Gln Lys Pro Gly Gln Ala Pro Arg Leu Leu Ile
        35                  40                  45

Tyr Tyr Ser Ser Asn Leu His Ser Gly Val Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Ala Tyr Tyr Cys Gln Gln Ser Ile Lys Leu Pro Leu
                85                  90                  95

Thr Phe Gly Ser Gly Thr Lys Val Glu Ile Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: Synthetic peptide

<400> SEQUENCE: 2

Glu Ile Glu Leu Thr Gln Ser Pro Ser Ser Leu Ser Val Ser Leu Gly
1               5                   10                  15

Asp Arg Val Thr Ile Ser Cys Ser Ala Ser Gln Asp Ile Arg Asn Asn
            20                  25                  30
```

Leu Asn Trp Tyr Gln Gln Lys Pro Gly Gln Ala Pro Arg Leu Leu Ile
            35                  40                  45

Tyr Tyr Ser Ser Asn Leu Gln Thr Gly Val Pro Ala Arg Phe Ser Gly
        50                  55                  60

Ser Gly Ser Gly Thr Asp Phe Thr Leu Thr Ile Ser Arg Leu Glu Pro
65                  70                  75                  80

Glu Asp Val Ala Ala Tyr Tyr Cys Gln Gln Ser Ile Lys Leu Pro Phe
                85                  90                  95

Thr Phe Gly Ser Gly Thr Lys Val Glu Ile Lys
            100                 105

<210> SEQ ID NO 3
<211> LENGTH: 107
<212> TYPE: PRT
<213> ORGANISM: Artificial Sequence
<220> FEATURE:
<223> OTHER INFORMATION: Synthetic peptide

<400> SEQUENCE: 3

Asp Ile Glu Met Thr Gln Ser Pro Ser Ser Leu Ser Ala Ser Ala Gly
1               5                   10                  15

Glu Arg Val Thr Ile Ser Cys Arg Ala Ser Gln Gly Ile Arg Asn Ser
            20                  25                  30

Leu Asn Trp Tyr Gln Gln Lys Pro Gly Gln Ala Pro Arg Leu Leu Ile
            35                  40                  45

Tyr Tyr Ser Ser Asn Leu Gln Thr Gly Val Pro Ser Arg Phe Ser Gly
        50                  55                  60

Ser Gly Ser Gly Thr Asp Phe Thr Leu Thr Ile Ser Arg Leu Gln Ala
65                  70                  75                  80

Glu Asp Phe Ala Thr Tyr Tyr Cys Gln Gln Ser Asn Lys Leu Pro Phe
                85                  90                  95

Thr Phe Gly Ser Gly Thr Lys Val Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 4

Asp Ile Leu Leu Thr Gln Ser Pro Ser Ser Leu Ser Ala Thr Pro Gly
1               5                   10                  15

Glu Arg Ala Thr Ile Thr Cys Arg Ala Ser Gln Gly Ile Arg Asn Asn
            20                  25                  30

Leu Asn Trp Tyr Gln Gln Lys Pro Gly Gln Ala Pro Arg Leu Leu Ile
            35                  40                  45

Tyr Tyr Ser Ser Asn Leu Gln Ser Gly Val Pro Ser Arg Phe Ser Gly
        50                  55                  60

Ser Gly Ser Gly Thr Asp Phe Thr Leu Thr Ile Ser Arg Leu Gln Pro
65                  70                  75                  80

Glu Asp Val Ala Ala Tyr Tyr Cys Gln Gln Ser Ile Lys Leu Pro Phe
                85                  90                  95

Thr Phe Gly Ser Gly Thr Lys Val Glu Ile Lys
            100                 105

```
<210> SEQ ID NO 5
<211> LENGTH: 107
<212> TYPE: PRT
<213> ORGANISM: Artificial Sequence
<220> FEATURE:
<223> OTHER INFORMATION: Synthetic peptide

<400> SEQUENCE: 5

Glu Ile Glu Met Thr Gln Ser Pro Ser Ser Leu Ser Val Ser Ala Gly
1               5                   10                  15

Glu Arg Ala Thr Ile Ser Cys Ser Ala Ser Gln Asp Ile Arg Asn Ser
            20                  25                  30

Leu Asn Trp Tyr Gln Gln Lys Pro Gly Gln Ala Pro Arg Leu Leu Ile
        35                  40                  45

Tyr Tyr Ser Ser Asn Leu His Thr Gly Val Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Val Ala Ile Tyr Tyr Cys Gln Gln Ser Asn Lys Leu Pro Leu
                85                  90                  95

Thr Phe Gly Ser Gly Thr Lys Val Glu Ile Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: Syntetic peptide

<400> SEQUENCE: 6

Glu Ile Glu Leu Thr Gln Ser Pro Ser Ser Leu Ser Val Ser Pro Gly
1               5                   10                  15

Asp Arg Val Thr Ile Ser Cys Ser Ala Ser Gln Gly Ile Arg Asn Ser
            20                  25                  30

Leu Asn Trp Tyr Gln Gln Lys Pro Gly Gln Ala Pro Arg Leu Leu Ile
        35                  40                  45

Tyr Tyr Ser Ser Asn Leu His Thr Gly Val Pro Ala Arg Phe Ser Gly
    50                  55                  60

Ser Gly Ser Gly Thr Asp Phe Thr Leu Thr Ile Ser Arg Leu Gln Ala
65                  70                  75                  80

Glu Asp Phe Ala Thr Tyr Tyr Cys Gln Gln Ser Ile Lys Leu Pro Leu
                85                  90                  95

Thr Phe Gly Ser Gly Thr Lys Val Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: Synthetic peptide

<400> SEQUENCE: 7

Asp Ile Leu Met Thr Gln Ser Pro Ser Ser Leu Ser Ala Ser Pro Gly
1               5                   10                  15

Asp Arg Val Thr Ile Ser Cys Arg Ala Ser Gln Asp Ile Arg Asn Asn
            20                  25                  30

Leu Asn Trp Tyr Gln Gln Lys Pro Gly Gln Ala Pro Arg Leu Leu Ile
        35                  40                  45
```

```
Tyr Tyr Ser Ser Asn Leu Gln Thr Gly Val Pro Ala Arg Phe Ser Gly
         50                  55                  60

Ser Gly Ser Gly Thr Asp Phe Thr Leu Thr Ile Ser Arg Leu Glu Pro
 65                  70                  75                  80

Glu Asp Phe Ala Ala Tyr Tyr Cys Gln Gln Ser Ile Lys Leu Pro Leu
                 85                  90                  95

Thr Phe Gly Ser Gly Thr Lys Val Glu Ile Lys
            100                 105

<210> SEQ ID NO 8
<211> LENGTH: 116
<212> TYPE: PRT
<213> ORGANISM: Artificial Sequence
<220> FEATURE:
<223> OTHER INFORMATION: Synthetic peptide

<400> SEQUENCE: 8

Glu Val Gln Leu Val Glu Ser Gly Ala Gly Val Lys Gln Pro Gly Gly
 1               5                  10                  15

Thr Leu Arg Leu Thr Cys Thr Ala Ser Gly Phe Ser Leu Thr Thr Tyr
             20                  25                  30

Gly Val His Trp Val Arg Gln Ala Pro Gly Lys Gly Leu Glu Trp Val
         35                  40                  45

Gly Val Ile Trp Gly Asp Gly Arg Thr Asp Tyr Asp Ala Ala Phe Met
     50                  55                  60

Ser Arg Val Thr Ile Ser Lys Asp Thr Ser Lys Ser Thr Val Tyr Leu
 65                  70                  75                  80

Gln Met Asn Ser Leu Arg Ala Glu Asp Thr Ala Val Tyr Tyr Cys Met
                 85                  90                  95

Arg Asn Arg His Asp Trp Phe Asp Tyr Trp Gly Gln Gly Thr Thr Val
            100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: Synthetic peptide

<400> SEQUENCE: 9

Glu Val Gln Leu Val Gln Ser Gly Gly Gly Val Lys Gln Pro Gly Glu
 1               5                  10                  15

Thr Leu Arg Leu Thr Cys Thr Ala Ser Gly Phe Ser Leu Thr Thr Tyr
             20                  25                  30

Gly Val His Trp Val Arg Gln Ala Pro Gly Lys Gly Leu Glu Trp Val
         35                  40                  45

Gly Val Ile Trp Gly Asp Gly Arg Thr Asp Tyr Asp Ala Ala Phe Met
     50                  55                  60

Ser Arg Val Thr Ile Ser Lys Asp Thr Ser Lys Ser Thr Ala Tyr Leu
 65                  70                  75                  80

Gln Met Asn Ser Leu Arg Ala Glu Asp Thr Ala Val Tyr Tyr Cys Met
                 85                  90                  95

Arg Asn Arg His Asp Trp Phe Asp Tyr Trp Gly Gln Gly Thr Thr Val
            100                 105                 110

Thr Val Ser Ser
```

```
<210> SEQ ID NO 10
<211> LENGTH: 116
<212> TYPE: PRT
<213> ORGANISM: Artificial Sequence
<220> FEATURE:
<223> OTHER INFORMATION: Synthetic peptide

<400> SEQUENCE: 10

Glu Val Gln Leu Val Glu Ser Gly Ala Gly Val Glu Gln Pro Gly Gly
1               5                   10                  15

Thr Leu Arg Leu Thr Cys Thr Ala Ser Gly Phe Ser Leu Thr Thr Tyr
            20                  25                  30

Gly Val His Trp Val Arg Gln Ala Pro Gly Lys Gly Leu Glu Trp Met
        35                  40                  45

Gly Val Ile Trp Gly Asp Gly Arg Thr Asp Tyr Asp Ala Ala Phe Met
    50                  55                  60

Ser Arg Val Thr Ile Ser Arg Asp Thr Ser Lys Ser Thr Ala Tyr Leu
65                  70                  75                  80

Gln Leu Asn Ser Leu Arg Ala Glu Asp Thr Ala Val Tyr Tyr Cys Val
                85                  90                  95

Arg Asn Arg His Asp Trp Phe Asp Tyr Trp Gly Gln Gly Thr Thr Val
            100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Synthetic peptide

<400> SEQUENCE: 11

Glu Val Gln Leu Val Glu Ser Gly Ala Glu Leu Val Gln Pro Gly Gly
1               5                   10                  15

Ser Leu Arg Leu Thr Cys Lys Ala Ser Gly Phe Thr Leu Asn Thr Tyr
            20                  25                  30

Gly Val His Trp Val Arg Gln Ala Pro Gly Lys Gly Leu Glu Trp Met
        35                  40                  45

Gly Val Ile Trp Gly Gly Gly Arg Thr Asp Tyr Asp Ala Ser Phe Met
    50                  55                  60

Ser Arg Val Thr Ile Ser Lys Asp Asn Ser Lys Asn Thr Ala Tyr Leu
65                  70                  75                  80

Gln Leu Asn Ser Leu Arg Ala Glu Asp Thr Ala Val Tyr Tyr Cys Thr
                85                  90                  95

Arg Ser Arg His Asp Trp Phe Asp Tyr Trp Gly Gln Gly Thr Thr Val
            100                 105                 110

Thr Val Ser Ser
        115

<210> SEQ ID NO 12
<211> LENGTH: 116
<212> TYPE: PRT
<213> ORGANISM: Artificial Sequence
<220> FEATURE:
<223> OTHER INFORMATION: Synthetic peptide

<400> SEQUENCE: 12
```

Glu Val Gln Leu Val Gln Ser Gly Gly Gly Leu Lys Gln Pro Gly Glu
1               5                   10                  15

Thr Leu Arg Leu Ser Cys Thr Ala Ser Gly Tyr Ser Leu Thr Thr Tyr
            20                  25                  30

Gly Val His Trp Val Arg Gln Ala Pro Gly Lys Gly Leu Glu Trp Met
        35                  40                  45

Gly Val Ile Trp Gly Asp Gly Arg Thr Asp Tyr Asp Ser Ser Phe Met
    50                  55                  60

Ser Arg Val Thr Ile Ser Lys Asp Thr Ser Lys Ser Thr Ala Tyr Leu
65                  70                  75                  80

Gln Leu Asn Ser Leu Arg Ala Glu Asp Thr Ala Val Tyr Tyr Cys Thr
                85                  90                  95

Arg Asn Arg His Asp Trp Phe Asp Tyr Trp Gly Gln Gly Thr Thr Val
            100                 105                 110

Thr Val Ser Ser
        115

<210> SEQ ID NO 13
<211> LENGTH: 116
<212> TYPE: PRT
<213> ORGANISM: Artificial Sequence
<220> FEATURE:
<223> OTHER INFORMATION: Synthetic peptide

<400> SEQUENCE: 13

Glu Val Gln Leu Val Gln Ser Gly Gly Gly Val Lys Gln Pro Gly Glu
1               5                   10                  15

Thr Leu Arg Leu Thr Cys Thr Ala Ser Gly Phe Ser Leu Ser Thr Tyr
            20                  25                  30

Gly Val His Trp Val Arg Gln Ala Pro Gly Lys Gly Leu Glu Trp Val
        35                  40                  45

Gly Val Ile Trp Gly Asp Gly Arg Thr Asp Tyr Asp Ala Ala Phe Met
    50                  55                  60

Ser Arg Val Thr Ile Ser Lys Asp Thr Ser Lys Ser Thr Val Tyr Leu
65                  70                  75                  80

Gln Met Asn Ser Leu Arg Ala Glu Asp Thr Ala Val Tyr Tyr Cys Met
                85                  90                  95

Arg Asn Arg His Asp Trp Phe Asp Tyr Trp Gly Gln Gly Thr Thr Val
            100                 105                 110

Thr Val Ser Ser
        115

<210> SEQ ID NO 14
<211> LENGTH: 116
<212> TYPE: PRT
<213> ORGANISM: Artificial Sequence
<220> FEATURE:
<223> OTHER INFORMATION: Synthetic peptide

<400> SEQUENCE: 14

Glu Val Gln Leu Val Glu Ser Gly Gly Gly Val Lys Gln Pro Gly Glu
1               5                   10                  15

Thr Leu Arg Leu Thr Cys Thr Ala Ser Gly Phe Ser Leu Ser Thr Tyr
            20                  25                  30

Gly Val His Trp Val Arg Gln Ala Pro Gly Lys Gly Leu Glu Trp Val
        35                  40                  45

Gly Val Ile Trp Gly Asp Gly Arg Thr Asp Tyr Asp Ala Ala Phe Met

```
            50                  55                  60
Ser Arg Val Thr Ile Ser Lys Asp Thr Ser Lys Ser Thr Val Tyr Leu
 65                  70                  75                  80

Gln Met Asn Ser Leu Arg Ala Glu Asp Thr Ala Val Tyr Tyr Cys Met
                 85                  90                  95

Arg Asn Arg His Asp Trp Phe Asp Tyr Trp Gly Gln Gly Thr Thr Val
            100                 105                 110

Thr Val Ser Ser
        115

<210> SEQ ID NO 15
<211> LENGTH: 116
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa is Glu or Gln
<220> FEATURE:
<221> NAME/KEY: MISC_FEATURE
<222> LOCATION: (9)..(9)
<223> OTHER INFORMATION: Xaa is Ala or Gly
<220> FEATURE:
<221> NAME/KEY: MISC_FEATURE
<222> LOCATION: (10)..(10)
<223> OTHER INFORMATION: Xaa is Gly or Glu
<220> FEATURE:
<221> NAME/KEY: MISC_FEATURE
<222> LOCATION: (11)..(11)
<223> OTHER INFORMATION: Xaa is Leu or Val
<220> FEATURE:
<221> NAME/KEY: MISC_FEATURE
<222> LOCATION: (12)..(12)
<223> OTHER INFORMATION: Xaa is Val, Lys or Glu
<220> FEATURE:
<221> NAME/KEY: MISC_FEATURE
<222> LOCATION: (16)..(16)
<223> OTHER INFORMATION: Xaa is Gly or Glu
<220> FEATURE:
<221> NAME/KEY: MISC_FEATURE
<222> LOCATION: (17)..(17)
<223> OTHER INFORMATION: Xaa is Thr or Ser
<220> FEATURE:
<221> NAME/KEY: MISC_FEATURE
<222> LOCATION: (21)..(21)
<223> OTHER INFORMATION: Xaa is Thr or Ser
<220> FEATURE:
<221> NAME/KEY: MISC_FEATURE
<222> LOCATION: (23)..(23)
<223> OTHER INFORMATION: Xaa is Thr or Lys
<220> FEATURE:
<221> NAME/KEY: MISC_FEATURE
<222> LOCATION: (27)..(27)
<223> OTHER INFORMATION: Xaa is Phe or Tyr
<220> FEATURE:
<221> NAME/KEY: MISC_FEATURE
<222> LOCATION: (28)..(28)
<223> OTHER INFORMATION: Xaa is Ser or Thr
<220> FEATURE:
<221> NAME/KEY: MISC_FEATURE
<222> LOCATION: (30)..(30)
<223> OTHER INFORMATION: Xaa is Thr, Asn or Ser
<220> FEATURE:
<221> NAME/KEY: MISC_FEATURE
<222> LOCATION: (48)..(48)
<223> OTHER INFORMATION: Xaa is Val or Met
<220> FEATURE:
<221> NAME/KEY: MISC_FEATURE
<222> LOCATION: (54)..(54)
<223> OTHER INFORMATION: Xaa is Gly or Asp
<220> FEATURE:
<221> NAME/KEY: MISC_FEATURE
```

```
<222> LOCATION: (61)..(61)
<223> OTHER INFORMATION: Xaa is Ala or Ser
<220> FEATURE:
<221> NAME/KEY: MISC_FEATURE
<222> LOCATION: (62)..(62)
<223> OTHER INFORMATION: Xaa is Ala or Ser
<220> FEATURE:
<221> NAME/KEY: MISC_FEATURE
<222> LOCATION: (71)..(71)
<223> OTHER INFORMATION: Xaa is Lys or Arg
<220> FEATURE:
<221> NAME/KEY: MISC_FEATURE
<222> LOCATION: (73)..(73)
<223> OTHER INFORMATION: Xaa is Asn or Thr
<220> FEATURE:
<221> NAME/KEY: MISC_FEATURE
<222> LOCATION: (76)..(76)
<223> OTHER INFORMATION: Xaa is Ser or Asn
<220> FEATURE:
<221> NAME/KEY: MISC_FEATURE
<222> LOCATION: (78)..(78)
<223> OTHER INFORMATION: Xaa is Val or Ala
<220> FEATURE:
<221> NAME/KEY: MISC_FEATURE
<222> LOCATION: (82)..(82)
<223> OTHER INFORMATION: Xaa is Met or Leu
<220> FEATURE:
<221> NAME/KEY: MISC_FEATURE
<222> LOCATION: (96)..(96)
<223> OTHER INFORMATION: Xaa is Val, Met or Thr
<220> FEATURE:
<221> NAME/KEY: misc_feature
<222> LOCATION: (98)..(98)
<223> OTHER INFORMATION: Xaa can be any naturally occurring amino acid

<400> SEQUENCE: 15

Glu Val Gln Leu Val Xaa Ser Gly Xaa Xaa Xaa Xaa Gln Pro Gly Xaa
1               5                   10                  15

Xaa Ala Arg Leu Xaa Cys Xaa Ala Ser Gly Xaa Xaa Leu Xaa Thr Tyr
            20                  25                  30

Gly Val His Trp Val Arg Gln Ala Pro Gly Lys Gly Leu Glu Trp Xaa
        35                  40                  45

Gly Val Ile Trp Gly Xaa Gly Arg Thr Asp Tyr Asp Xaa Xaa Phe Met
    50                  55                  60

Ser Arg Val Thr Ile Ser Xaa Asp Xaa Ser Lys Xaa Thr Xaa Tyr Leu
65                  70                  75                  80

Gln Xaa Asn Ser Leu Arg Ala Glu Asp Thr Ala Val Tyr Tyr Cys Xaa
            85                  90                  95

Arg Xaa Arg His Asp Trp Phe Asp Tyr Trp Gly Gln Gly Thr Thr Val
        100                 105                 110

Thr Val Ser Ser
        115

<210> SEQ ID NO 16
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (3)..(3)
<223> OTHER INFORMATION: Xaa is Leu or Glu
<220> FEATURE:
<221> NAME/KEY: MISC_FEATURE
<222> LOCATION: (4)..(4)
```

```
<223> OTHER INFORMATION: Xaa is Met or Leu
<220> FEATURE:
<221> NAME/KEY: MISC_FEATURE
<222> LOCATION: (13)..(13)
<223> OTHER INFORMATION: Xaa is Ala or Val
<220> FEATURE:
<221> NAME/KEY: MISC_FEATURE
<222> LOCATION: (14)..(14)
<223> OTHER INFORMATION: Xaa is Ser or Thr
<220> FEATURE:
<221> NAME/KEY: MISC_FEATURE
<222> LOCATION: (15)..(15)
<223> OTHER INFORMATION: Xaa is Leu, Pro or Ala
<220> FEATURE:
<221> NAME/KEY: MISC_FEATURE
<222> LOCATION: (17)..(17)
<223> OTHER INFORMATION: Xaa is Asp or Glu
<220> FEATURE:
<221> NAME/KEY: MISC_FEATURE
<222> LOCATION: (19)..(19)
<223> OTHER INFORMATION: Xaa is Val or Ala
<220> FEATURE:
<221> NAME/KEY: MISC_FEATURE
<222> LOCATION: (22)..(22)
<223> OTHER INFORMATION: Xaa is Thr or Ser
<220> FEATURE:
<221> NAME/KEY: MISC_FEATURE
<222> LOCATION: (24)..(24)
<223> OTHER INFORMATION: Xaa is Ser or Arg
<220> FEATURE:
<221> NAME/KEY: MISC_FEATURE
<222> LOCATION: (28)..(28)
<223> OTHER INFORMATION: Xaa is Gly or Asp
<220> FEATURE:
<221> NAME/KEY: MISC_FEATURE
<222> LOCATION: (32)..(32)
<223> OTHER INFORMATION: Xaa is Ser or Asn
<220> FEATURE:
<221> NAME/KEY: MISC_FEATURE
<222> LOCATION: (55)..(55)
<223> OTHER INFORMATION: Xaa is His or Gln
<220> FEATURE:
<221> NAME/KEY: MISC_FEATURE
<222> LOCATION: (56)..(56)
<223> OTHER INFORMATION: Xaa is Ser or Thr
<220> FEATURE:
<221> NAME/KEY: MISC_FEATURE
<222> LOCATION: (60)..(60)
<223> OTHER INFORMATION: Xaa is Ser, Asp or Ala
<220> FEATURE:
<221> NAME/KEY: MISC_FEATURE
<222> LOCATION: (79)..(79)
<223> OTHER INFORMATION: Xaa is Glu or Gln
<220> FEATURE:
<221> NAME/KEY: MISC_FEATURE
<222> LOCATION: (80)..(80)
<223> OTHER INFORMATION: Xaa is Pro or Ala
<220> FEATURE:
<221> NAME/KEY: MISC_FEATURE
<222> LOCATION: (83)..(83)
<223> OTHER INFORMATION: Xaa is Phe or Val
<220> FEATURE:
<221> NAME/KEY: MISC_FEATURE
<222> LOCATION: (85)..(85)
<223> OTHER INFORMATION: Xaa is Thr, Ala or Ile
<220> FEATURE:
<221> NAME/KEY: MISC_FEATURE
<222> LOCATION: (92)..(92)
<223> OTHER INFORMATION: Xaa is Ile or Asn
<220> FEATURE:
<221> NAME/KEY: MISC_FEATURE
<222> LOCATION: (96)..(96)
<223> OTHER INFORMATION: Xaa is Phe or Leu

<400> SEQUENCE: 16

Xaa Ile Xaa Xaa Thr Gln Ser Pro Ser Ser Leu Ser Xaa Xaa Xaa Gly
1               5                   10                  15
```

Xaa Arg Xaa Thr Ile Xaa Cys Xaa Ala Ser Gln Xaa Ile Arg Asn Xaa
            20                  25                  30

Leu Asn Trp Tyr Gln Gln Lys Pro Gly Gln Ala Pro Arg Leu Leu Ile
        35                  40                  45

Tyr Tyr Ser Ser Asn Leu Xaa Xaa Gly Val Pro Xaa Arg Phe Ser Gly
    50                  55                  60

Ser Gly Ser Gly Thr Asp Phe Thr Leu Thr Ile Ser Arg Leu Xaa Xaa
65                  70                  75                  80

Glu Asp Xaa Ala Xaa Tyr Tyr Cys Gln Gln Ser Xaa Lys Leu Pro Xaa
            85                  90                  95

Thr Phe Gly Ser Gly Thr Lys Val Glu Ile Lys
            100                 105

<210> SEQ ID NO 17
<211> LENGTH: 465
<212> TYPE: PRT
<213> ORGANISM: Artificial Sequence
<220> FEATURE:
<223> OTHER INFORMATION: Synthetic pepitde

<400> SEQUENCE: 17

Met Glu Trp Ser Trp Val Phe Leu Phe Phe Leu Ser Val Thr Thr Gly
1               5                   10                  15

Val His Ser Glu Val Gln Leu Val Glu Ser Gly Ala Gly Val Lys Gln
            20                  25                  30

Pro Gly Gly Thr Leu Arg Leu Thr Cys Thr Ala Ser Gly Phe Ser Leu
        35                  40                  45

Thr Thr Tyr Gly Val His Trp Val Arg Gln Ala Pro Gly Lys Gly Leu
    50                  55                  60

Glu Trp Val Gly Val Ile Trp Gly Asp Gly Arg Thr Asp Tyr Asp Ala
65                  70                  75                  80

Ala Phe Met Ser Arg Val Thr Ile Ser Lys Asp Thr Ser Lys Ser Thr
            85                  90                  95

Val Tyr Leu Gln Met Asn Ser Leu Arg Ala Glu Asp Thr Ala Val Tyr
            100                 105                 110

Tyr Cys Met Arg Asn Arg His Asp Trp Phe Asp Tyr Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

```
Arg Thr Pro Glu Val Thr Cys Val Val Asp Val Ser His Glu Asp
            275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
            450                 455                 460

Lys
465

<210> SEQ ID NO 18
<211> LENGTH: 234
<212> TYPE: PRT
<213> ORGANISM: Artificial Sequence
<220> FEATURE:
<223> OTHER INFORMATION: Synthetic peptide

<400> SEQUENCE: 18

Met Ser Val Pro Thr Gln Val Leu Gly Leu Leu Leu Leu Trp Leu Thr
1               5                   10                  15

Asp Ala Arg Cys Asp Ile Leu Leu Thr Gln Ser Pro Ser Ser Leu Ser
            20                  25                  30

Ala Thr Pro Gly Glu Arg Ala Thr Ile Thr Cys Arg Ala Ser Gln Gly
        35                  40                  45

Ile Arg Asn Asn Leu Asn Trp Tyr Gln Gln Lys Pro Gly Gln Ala Pro
50                  55                  60

Arg Leu Leu Ile Tyr Tyr Ser Ser Asn Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Arg Leu Gln Pro Glu Asp Val Ala Ala Tyr Tyr Cys Gln Gln Ser Ile
            100                 105                 110

Lys Leu Pro Phe Thr Phe Gly Ser Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160
```

-continued

```
Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 19
<211> LENGTH: 13
<212> TYPE: PRT
<213> ORGANISM: Artificial Sequence
<220> FEATURE:
<223> OTHER INFORMATION: Synthetic peptide

<400> SEQUENCE: 19

Tyr Ser Leu Arg Trp Ile Ser Asp His Glu Tyr Leu Tyr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic peptide

<400> SEQUENCE: 20

Leu Glu Tyr Asn Tyr Val Lys Gln Trp Arg His Ser Tyr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic peptide

<400> SEQUENCE: 21

Thr Trp Ser Pro Val Gly His Lys Leu Ala Tyr Val Trp
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic peptide

<400> SEQUENCE: 22

Leu Trp Trp Ser Pro Asn Gly Thr Phe Leu Ala Tyr Ala
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic peptide

<400> SEQUENCE: 23

Arg Ile Ser Leu Gln Trp Leu Arg Arg Ile Gln Asn Tyr
1               5                   10
```

```
<210> SEQ ID NO 24
<211> LENGTH: 13
<212> TYPE: PRT
<213> ORGANISM: Artificial Sequence
<220> FEATURE:
<223> OTHER INFORMATION: Synthetic peptide

<400> SEQUENCE: 24

Tyr Val Lys Gln Trp Arg His Ser Tyr Thr Ala Ser Tyr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic peptide

<400> SEQUENCE: 25

Glu Glu Glu Val Phe Ser Ala Tyr Ser Ala Leu Trp Trp
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic peptide

<400> SEQUENCE: 26

Asp Tyr Ser Ile Ser Pro Asp Gly Gln Phe Ile Leu Leu
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic peptide

<400> SEQUENCE: 27

Ser Ile Ser Pro Asp Gly Gln Phe Ile Leu Leu Glu Tyr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic peptide

<400> SEQUENCE: 28

Ile Tyr Val Lys Ile Glu Pro Asn Leu Pro Ser Tyr Arg
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Synthetic peptide

<400> SEQUENCE: 29

Gly Gly Gly Gly Ser Gly Gly Gly Ser Gly Gly Gly Gly Ser
1               5                   10                  15
```

<210> SEQ ID NO 30
<211> LENGTH: 10
<212> TYPE: PRT
<213> ORGANISM: Artificial Sequence
<220> FEATURE:
<223> OTHER INFORMATION: Synthetic peptide

<400> SEQUENCE: 30

Phe Ser Leu Thr Thr Tyr Gly Val His Trp
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Synthetic peptide

<400> SEQUENCE: 31

Ile Trp Gly Gly Gly Arg Thr Asp Tyr Asp Ala Ala Phe Ile Ser Arg
1               5                   10                  15

<210> SEQ ID NO 32
<211> LENGTH: 8
<212> TYPE: PRT
<213> ORGANISM: Artificial Sequence
<220> FEATURE:
<223> OTHER INFORMATION: Synthetic peptide

<400> SEQUENCE: 32

Arg His Asp Trp Phe Asp Tyr Trp
1               5

<210> SEQ ID NO 33
<211> LENGTH: 11
<212> TYPE: PRT
<213> ORGANISM: Artificial Sequence
<220> FEATURE:
<223> OTHER INFORMATION: Synthetic peptide

<400> SEQUENCE: 33

Ala Ser Gln Gly Ile Arg Asn Ser Leu Asn Trp
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide

<400> SEQUENCE: 34

Ser Ser Asn Leu His Ser Gly
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide

<400> SEQUENCE: 35

Gln Ser Ile Lys Leu Pro Phe Thr Phe
1               5

```
<210> SEQ ID NO 36
<211> LENGTH: 10
<212> TYPE: PRT
<213> ORGANISM: Artificial Sequence
<220> FEATURE:
<223> OTHER INFORMATION: Synthetic peptide

<400> SEQUENCE: 36

Phe Ser Leu Thr Thr Tyr Gly Val His Trp
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Synthetic peptide

<400> SEQUENCE: 37

Ile Trp Gly Asp Gly Arg Thr Asp Tyr Asp Ala Ala Phe Met Ser Arg
1               5                   10                  15

<210> SEQ ID NO 38
<211> LENGTH: 8
<212> TYPE: PRT
<213> ORGANISM: Artificial Sequence
<220> FEATURE:
<223> OTHER INFORMATION: Synthetic peptide

<400> SEQUENCE: 38

Arg His Asp Trp Phe Asp Tyr Trp
1               5

<210> SEQ ID NO 39
<211> LENGTH: 11
<212> TYPE: PRT
<213> ORGANISM: Artificial Sequence
<220> FEATURE:
<223> OTHER INFORMATION: Synthetic peptide

<400> SEQUENCE: 39

Ala Ser Gln Gly Ile Arg Asn Asn Leu Asn Trp
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

Ser Ser Asn Leu Gln Ser Gly
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Gln Ser Ile Lys Leu Pro Phe Thr Phe
1               5
```